US 7,758,863 B2

(12) United States Patent
Bogoch et al.

(10) Patent No.: US 7,758,863 B2
(45) Date of Patent: **\*Jul. 20, 2010**

(54) REPLIKIN PEPTIDES IN RAPID REPLICATION OF GLIOMA CELLS AND IN INFLUENZA EPIDEMICS

(76) Inventors: Samuel Bogoch, 46 E. 91st St., New York, NY (US) 10128; Elenore S. Bogoch, 46 E. 91st St., New York, NY (US) 10128

( * ) Notice: Subject to any disclaimer, the term of this patent is extended or adjusted under 35 U.S.C. 154(b) by 0 days.

This patent is subject to a terminal disclaimer.

(21) Appl. No.: 12/412,888

(22) Filed: Mar. 27, 2009

(65) Prior Publication Data

US 2009/0191189 A1 Jul. 30, 2009

Related U.S. Application Data

(60) Division of application No. 11/590,852, filed on Nov. 1, 2006, which is a continuation of application No. 10/105,232, filed on Mar. 26, 2002, now Pat. No. 7,189,800, which is a continuation-in-part of application No. 09/984,057, filed on Oct. 26, 2001, now Pat. No. 7,420,028.

(60) Provisional application No. 60/278,761, filed on Mar. 27, 2001, provisional application No. 60/303,396, filed on Jul. 9, 2001.

(51) Int. Cl.
*A61K 39/145* (2006.01)
*C07K 4/00* (2006.01)
*C07K 14/00* (2006.01)

(52) U.S. Cl. .................. 424/185.1; 424/209.1; 530/300
(58) Field of Classification Search ........................ None
See application file for complete search history.

(56) References Cited

U.S. PATENT DOCUMENTS

| 5,104,854 | A | 4/1992 | Schlesinger et al. |
| 5,231,167 | A | 7/1993 | Zanetti et al. |
| 5,280,113 | A | 1/1994 | Rademacher et al. |
| 5,679,352 | A | 10/1997 | Chong et al. |
| 5,866,690 | A | 2/1999 | Bogoch |
| 6,023,659 | A | 2/2000 | Seilhamer |
| 6,070,126 | A | 5/2000 | Kokolus |
| 6,242,578 | B1 | 6/2001 | Bogoch |
| 6,256,647 | B1 | 7/2001 | Toh |
| 6,470,277 | B1 | 10/2002 | Chin |
| 6,484,166 | B1 | 11/2002 | Maynard |
| 6,638,505 | B2 | 10/2003 | Bogoch |
| 7,189,800 | B2 * | 3/2007 | Bogoch et al. ............. 530/300 |
| 2005/0271676 | A1 | 12/2005 | Sette et al. |

FOREIGN PATENT DOCUMENTS

| EP | 0 108 564 A1 | 4/1984 |
| IT | 98MI0874 | 10/1999 |
| JP | 3-503166 T | 7/1991 |
| JP | 10-212300 A | 8/1998 |
| JP | 2000-253876 A | 9/2000 |
| WO | 8907112 A1 | 10/1989 |
| WO | WO 9632106 | 10/1996 |
| WO | WO 00/18351 | 4/2000 |
| WO | WO 0104135 A2 | 1/2001 |

OTHER PUBLICATIONS

Kazazic et al., "Mutational analysis of the role of charged residues in target-cell binding, potency and specificity of the pediocin-like bacteriocin sakacin P," Microbiology, (2002) 148: 2019-27.

Keppeler et al., "Elongation of thr N-acyl side chain of sialic acid in MDCK II cells inhibits influenza A virus infection," abstract, Biochemical and Biophysical Research Communications, Dec. 18, 1998, vol. 253, No. 2. Database Medline on STN, National Library of Medicine, (Bethesda, MD, USA), No. 99097253.

Kornblith P. L. et al., "Growth-inhibitory effect of diphenylhydantoin on murine astrocytomas," Neurosurgery, vol. 5, No. 2, pp. 259-263 (Aug. 1979), Medline, XP002199627.

Margalit et al., "Prediction of Immunodominant Helper T Cell Antigenic Sites From the Primary Sequence," Jour. of Immunology, vol. 138, 2213-2229, Apr. 1, 1987.

Orlando, C. et al. "A monoclonal antibody directed against the catalytic site of *Bacillus anthracis* adenylyl cyclase identifies a novel mammalian brain catalytic subunit," Biochemistry, 1992, pp. 3215-3222, vol. 31, American Chemical Society, XP002371438, ISSN: 0006-2960.

Pannifer, Crystal structure of the anthrax lethal factor, Nature, vol. 414, pp. 229-233 (Nov. 2001).

Patil et al., "Identification of a Talin-binding Site in the Integrin β3 Subunit Distinct from the NPLY Regulatory Motif of a Post-ligand Binding Functions," The Journal of Biological Chemistry, vol. 274, No. 1, Oct. 1, 1999, p. 28575-28583.

Rodman, Toby C. et al., "Human Immunodeficiency Virus (HIV) Tat-reactive Antibodies Present in Normal HIV-negative Sera and Depleted in HIV-positive Sera. Identification of the Epitope," vol. 175, pp. 1247-1253, (May 1992).

Seal et al., "Elevation of Serum Protein-Bound Carbohydrates and Haptoglobin in Schizophrenia," Clinical Chemistry; Oct. 1966, vol. 12, No. 10, pp. 709-716.

(Continued)

*Primary Examiner*—Mary E Mosher
*Assistant Examiner*—Myron G Hill
(74) *Attorney, Agent, or Firm*—Kenyon & Kenyon LLP

(57) ABSTRACT

Peptides of influenza virus hemagglutinin protein and *Plasmodium falciparum* malaria antigen, antibodies specific for the peptides, influenza vaccines, malaria vaccines and methods of stimulating the immune response of a subject to produce antibodies to influenza virus or malaria are disclosed. Also disclosed are methods for formulating vaccines for influenza virus.

16 Claims, 9 Drawing Sheets

OTHER PUBLICATIONS

Schenk, S. et al., "Four recombinant isoforms of Cor a 1, the major allergen of hazel pollen, show different reactivities with allergen-specific T-lymphocyte clones," European Journal of Biochemistry, 1994, pp. 717-722, vol. 224, XP002371408, ISSN: 0014-2956.

Sharma et al., "Synthesis and Characterization of a Peptide Identified as a Functional element in αA-crystallin," The Journal of Biological Chemistry, vol. 275, No. 6, Feb. 11, 2000, p. 3767-3771.

Shi, Immunogenicity and in vitro protective efficacy of a recombinant multistage *Plasmodium falciparum* candidate vaccine, PNAS vol. 96, No. 4, pp. 1615-1620 (Feb 1999).

Tanaka, T. et al., "Efficient Generation of Antibodies to Oncoproteins by using Synthetic Peptide Antigens." Proceedings of the National Academy of Sciences of USA, National Academy of Science, Washington, D.C., US, v. 82, No. 10, p. 3400-3404, tables 1, Peptide 21, XP000113798, ISSN: 0027-8424, May 1, 1985.

Weber, E. et al., "Fine Mapping of a Peptide Sequence Containing an Antigenic Site Conserved Among Arenaviruses," Virology, vol. 164, p. 30-38 (1988).

Yasuko, A-O, et al., "Intranasal administration of adjuvant-combined recombinant influenza virus HA vaccine protects mice from the lethal H5N1 virus infection." Microbes and Infection, vol. 8, Issues 12-13, pp. 2706-2714, Oct. 2006.

Zhao, Neutralizing monoclonal antibody against Anthrax lethal factor inhibits intoxication in a mouse model, Human Antibodies, vol. 12, pp. 129-135 (2003).

PCT International Search Report, PCT/US2002/09240, Jan. 14, 2004, USPTO, International Searching Authority, Washington DC.

PCT International Preliminary Examination Report, PCT/US2002/09240, Feb. 5, 2004, USPTO, International Preliminary Examination Authority, Alexandria, VA, USA.

PCT International Search Report, PCT/US2002/21494, May 30, 2003, USPTO, International Searching Authority, Washington DC.

PCT International Preliminary Examination Report, PCT/US2002/21494, Nov. 26, 2004, USPTO, International Searching Authority, Alexandria, VA, USA.

PCT International Search Report, PCT/US2003/08990, Dec. 7, 2005, International Searching Authority, USPTO, Alexandria, VA, USA.

PCT Written Opinion of the International Searching Authority, PCT/US2004/017936, Apr. 7, 2005, EPO, International Searching Authority, Munich, DE.

PCT International Search Report, PCT/US2004/017936, Apr. 28, 2005, EPO, International Searching Authority, Rijswijk, NL.

PCT International Preliminary Report on Patentability, PCT/US2004/017936, Apr. 13, 2007, USPTO, International Preliminary Examining Authority, Alexandria, VA, USA.

PCT International Search Report, PCT/US2005/014443, Oct. 21, 2005, EPO, International Searching Authority, Rijswijk, NL.

PCT Written Opinion of the International Searching Authority, PCT/US2005/014443, Apr. 12, 2006, EPO, International Searching Authority, Munich, DE.

PCT International Preliminary Report on Patentability, PCT/US2005/014443, Nov. 1, 2006, WIPO, International Bureau of WIPO, Geneva, Switzerland.

PCT International Search Report, PCT/US2006/05343, Sep. 25, 2007, USPTO, International Searching Authority, Alexandria, VA, USA.

PCT International Preliminary Report on Patentability, PCT/US2006/05343, Jul. 22, 2008, USPTO, International Preliminary Examining Authority, Alexandria, VA, USA.

PCT International Search Report, PCT/US2007/069978, Jun. 3, 2008, EPO, International Searching Authority, Rijswijk, NL.

PCT International Search Report and Written Opinion, PCT/US2007/82436, Jan. 9, 2009, USPTO, International Searching Authority, Alexandria, VA, USA.

PCT International Search Report and Written Opinion, PCT/US2008/00645, Feb. 2, 2009, USPTO, International Searching Authority, Alexandria, VA, USA.

PCT International Search Report and Written Opinion, PCT/US2008/061336, Feb. 2, 2009, EPO, International Searching Authority, Rijswijk, NL.

EP Supplementary Search 99944002, Apr. 20, 2004, EPO, Munich, DE.

EP Supplementary Search 02736514.7, Mar. 9, 2006.

EP Supplementary Search 02752202.8, Mar. 10, 2006.

EP Supplementary Search 03721445.9, Dec. 12, 2006, EPO, International Searching Authority, Munich, DE.

EP Office Action 04785929.3, Sep. 1, 2008, EPO, Netherlands.

NZ Office Action 553983, Jul. 16, 2008, IPO, New Zealand.

NCBI accession # gi 75059 Jul. 16, 1999.

NCBI Listing JQ0032, May 11, 2000.

NCBI Entrez Protein AAK38298, Apr. 19, 2001, see sequence of HA (http:www.ncbi.nlm.nih.gov/entrez/viewer.fcgi?db=protein &id=13676825), Apr. 19, 2001.

NCBI Accession No. NP 740460 (2000).

NCBI Blast Searching, Gene Gateway—Exploring Genes and Genetic Disorders, "Sequence similarity searching using NCBI Blast" (http:www.ORNL.gov/sci/techresources/Himan_Genome/chromosome/blast.shtml) (screenshot Apr. 27, 2005 by USPTO in U.S. Appl. No. 11/116,203).

NCBI Query Tutorial "Introduction" (http://www.ncbi.nim.nih.gov/Education/BLASTinfo/query_tutorial.html) (screenshot Apr. 27, 2005 by USPTO in U.S. Appl. No. 11/116,203).

NCBI Query Tutorial "Introduction to a BLAST Query" (http://www.ncbi.nim.nih.gov/Education/BLASTinfo/tut1.html) (screenshot Apr. 27, 2005 by USPTO in U.S. Appl. No. 11/116,203).

NCBI Query Tutorial "Setting up a BLAST Search" (http://www.ncbi.nim.nih.gov/Education/BLASTinfo/Blast_setup.html) (screenshot Apr. 27, 2005 by USPTO in U.S. Appl. No. 11/116,203).

PepBank entry 42800, corresponding to UniProt database entry P15516, Apr. 1, 1990, available at http://pepbank.mgh.harvard.edu, accessed Oct. 6, 2008.

3MOTIF—Search Instructions, 3motif in three Dimensions, article titles "Submitting a protein sequence": http://brutlag.stanford.edu/3motif/search_instr.html) (screenshot Apr. 27, 2005 by USPTO in U.S. Appl. No. 11/116,203).

Abrams M. B. et al., "Early Detection and Monitoring of cancer with the Anti-Malignin Antibody Test," Cancer detection and Prevention, XX, XX, vol. 18, No. 1, 1994, pp. 65-78, XP000673180, ISSN:0361-090X.

Atassi, M. Z. et al., "A novel approach for localization of the continuous protein antigenic sites by comprehensive synthetic surface scanning: Antibody and T cell activity to several influenza hemagglutinin synthetic sites," Immunological Communications, 1984, pp. 539-551, vol. 13, No. 6, Marcel Dekker, Inc., XP009062995, ISSN: 0090-0877.

Ben-Yedidia, T. et al., "Intranasal administration of peptide vaccine protects human/mouse radiation chimera from influenza infection," International Immunology, 1999, pp. 1043-1051, XP000914818, ISSN: 0953-8178.

Bogoch et al.: In vitro production of the general transformation antibody related to survival in human cancer patients; antimalignin antibody; Abstract, Cancer Detection and Prevention, 1988, vol. 12, Nos. 1-6, pp. 313-320. (Database Medline on STN National Library of Medicine (Bethesda, MD, USA) No. 89028479.

Bogoch et al. "In vitro production of the general transformation antibody related to survival in human cancer patients: antimalignin antibody," Cancer Detection and Prevention, Sep. 28, 1988, vol. 12, Nos. 1-6, pp. 313-320.

Bogoch, S. et al., "A Checklist for Suitability of Biomarkers as Surrogate Endpoints in Chemoprevention of Breast Cancer," Journal of Cellular Biochemistry, Supplement, Boston, US, vol. 19, pp. 173-185, XP009046492, ISSN: 0733-1959, 1994.

Bogoch et al., "Aglyco Pathology of Viral Receptors in Dementias," Annals of the New York Academy of Sciences, New York Academy of Sciences, New York Academy of Sciences, New York, NY, US, vol. 757, 1995, pp. 413-417, XP008003395, ISSN:0077-8923.

Bogoch et al., "Rapid replication and Replikintm structures: basis of the AMASRTest and CAVAXR," Cancer Detection and Prevention Online, Feb. 9, 2002, XP002350483.

Brown, L. R. et al., "Recognition of the influenza hemagglutinin by Class II MHC-restricted T lymphocytes and antibodies," Journal of Immunology, Oct. 14-15, 1991, pp. 2677-2684, vol. 147, No. 8, American Association of Immunologists, USA, XP002371257, ISSN: 0022-1767.

Brumeanu, T.M. et al., "Immunogenicity of a Contiguous T-B Synthetic Epitope of the A/PR/8/34 Influenza Virus," Journal of Virology, Jul. 1997, vol. 71, No. 7, pp. 5473-5480.

Bucher, D. et al., "M protein (M1) of influenza virus antigenic analysis and intracellular localization with monoclonal antibodies", J Virol. Sep. 1989; 63(9): pp. 3622-3633.

Carr C. M. et al., "A spring-loaded mechanism for the conformational change of influenza hemagglutinin," Cell, May 21, 1993, pp. 823-832, vol. 73, Cell Press, XP002059698, ISSN: 0092-8674.

Chambers, T.M. et al., "Antigenic and molecular characterization of subtype H13 hemagglutinin of influenza virus," Database NCBI on STN, Accession No. HMIVT2, Virology, pp. 180-188, abstract, 1989, 172(1).

Gao, Identification and characterization of T helper epitopes in the nucleoprotein of influenza A virus, J. Immunol.1989, vol. 143, pp. 3007-3014.

Gelder, C.M. et al., "Human CD4+ T-cell repertoire of response to influnza A virus hemagglutinin after recent natural infection," Journal of Virology, Dec. 1995, vol. 69, No. 12, pp. 7497-7506A.

PCT International Preliminary Report on Patentability, PCT/US2007/069978, May 1, 2009, USPTO, International Preliminary Examining Authority, Alexandria, VA, USA.

EP Office Action 04785929.3, Feb. 2, 2009, EPO, Netherlands.

NZ Office Action 560415, Mar. 6, 2009, IPO, New Zealand.

UnitProt/Swiss-Prot database entry O89746 1 Influenza A virus (strain A/Chicken/Hong Kong/220/1997 H5N1 genotype Gs/Gd) Nov. 1, 1998.

Japan Patent Office, Office Action in related Japanese Application No. 2009-024307, dated Sep. 8, 2009, Japan.

United States Patent and Trademark Office, US Office Action in related U.S. Appl. No. 11/615,578, dated Oct. 21, 2009, US.

NCBI Swiss-Prot Locus P33795, accessed Jul. 20, 2009.

Betakova et al., "The Vaccinia Virus A14.5L Gene Encodes a Hydrophobic 53-Amino-Acid Virion Membrane Protein That Enhances Virulence in Mice and Is Conserved among Vertebrate Poxviruses," Journal of Virology, vol. 74., No. 9, May 2000, p. 4085-4092.

Massung et al., "Potential virulence determinants in terminal regions of variola spallpox virus genome," Nature, vol. 366, Dec. 23/30, 1993, p. 748-751.

* cited by examiner

SPECIFICITY OF BINDING AND CYTOTOXICITY OF ANTIMALIGNIN ANTIBODY TO LEUKEMIC, BRAIN GLIOMA, AND SMALL CELL LUNG CARCINOMA CELLS

RELATION OF REPLIKIN CONCENTRATION TO PANDEMICS (P) AND EPIDEMICS (E) IN FOUR MAJOR STRAINS OF INFLUENZA VIRUS, 1902-2001

FIG.7

SEQUENCE LISTING

<160> NUMBER OF SEQ ID NOS: 535

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      glioma replikin

<400> SEQUENCE: 1

Lys Ala Gly Val Ala Phe Leu His Lys Lys
 1               5                  10

<210> SEQ ID NO 2
<211> LENGTH: 13
<212> TYPE: PRT
<213> ORGANISM: Saccharomyces cerevisiae

<400> SEQUENCE: 2

His Ser Ile Lys Arg Glu Leu Gly Ile Ile Phe Asp Lys

```
                1               5                10

<210> SEQ ID NO 3
<211> LENGTH: 10
<212> TYPE: PRT
<213> ORGANISM: Gemini vinis virus

<400> SEQUENCE: 3

His Lys Gln Lys Ile Val Ala Pro Val Lys
1               5                10

<210> SEQ ID NO 4
<211> LENGTH: 16
<212> TYPE: PRT
<213> ORGANISM: Unknown Organism
<220> FEATURE:
<223> OTHER INFORMATION: Description of Unknown Organism: Virus recognin

<400> SEQUENCE: 4

Tyr Lys Ala Gly Val Ala Phe Leu His Lys Lys Asn Asp Ile Asp Glu
1               5                10                  15

<210> SEQ ID NO 5
<211> LENGTH: 10
<212> TYPE: PRT
<213> ORGANISM: Human immunodeficiency virus type 1

<400> SEQUENCE: 5

Lys Cys Phe Asn Cys Gly Lys Glu Gly His
1               5                10

<210> SEQ ID NO 6
<211> LENGTH: 11
<212> TYPE: PRT
<213> ORGANISM: Human immunodeficiency virus type 1

<400> SEQUENCE: 6

Lys Val Tyr Leu Ala Trp Val Pro Ala His Lys
1               5                10

<210> SEQ ID NO 7
<211> LENGTH: 10
<212> TYPE: PRT
<213> ORGANISM: Human immunodeficiency virus type 2

<400> SEQUENCE: 7

Lys Cys Trp Asn Cys Gly Lys Glu Gly His
1               5                10

<210> SEQ ID NO 8
<211> LENGTH: 11
<212> TYPE: PRT
<213> ORGANISM: Maize streak virus

<400> SEQUENCE: 8

Lys Tyr Ile Val Cys Ala Arg Glu Ala His Lys
1               5                10

<210> SEQ ID NO 9
<211> LENGTH: 17
<212> TYPE: PRT
<213> ORGANISM: Maize streak virus

<400> SEQUENCE: 9

Lys Glu Lys Lys Pro Ser Lys Asp Glu Ile Met Arg Asp Ile Ile Ser
```

-continued

```
                1               5                  10                 15

His

<210> SEQ ID NO 10
<211> LENGTH: 9
<212> TYPE: PRT
<213> ORGANISM: Staphylococcus aureus

<400> SEQUENCE: 10

Lys Lys Glu Lys Thr Thr His Asn Lys
1               5

<210> SEQ ID NO 11
<211> LENGTH: 10
<212> TYPE: PRT
<213> ORGANISM: Bovine herpesvirus 4

<400> SEQUENCE: 11

His Lys Ile Asn Ile Thr Asn Gly Gln Lys
1               5                  10

<210> SEQ ID NO 12
<211> LENGTH: 10
<212> TYPE: PRT
<213> ORGANISM: Meleagrid herpesvirus 1

<400> SEQUENCE: 12

His Lys Asp Leu Tyr Arg Leu Leu Met Lys
1               5                  10

<210> SEQ ID NO 13
<211> LENGTH: 15
<212> TYPE: PRT
<213> ORGANISM: Unknown Organsim
<220> FEATURE:
<223> OTHER INFORMATION: Description of Unknown Organism: Virus recognin

<400> SEQUENCE: 13

Lys Phe Arg Ile Asn Ala Lys Asn Tyr Phe Leu Thr Tyr Pro His
1               5                  10                 15

<210> SEQ ID NO 14
<211> LENGTH: 19
<212> TYPE: PRT
<213> ORGANISM: Unknown Organism
<220> FEATURE:
<223> OTHER INFORMATION: Description of Unknown Organism: Virus recognin

<400> SEQUENCE: 14

Lys Asn Leu Glu Thr Pro Val Asn Lys Leu Phe Ile Arg Ile Cys Arg
1               5                  10                 15

Glu Phe His

<210> SEQ ID NO 15
<211> LENGTH: 14
<212> TYPE: PRT
<213> ORGANISM: Unknown Organism
<220> FEATURE:
<223> OTHER INFORMATION: Description of Unknown Organism: Virus recognin

<400> SEQUENCE: 15

His Pro Asn Ile Gln Ala Ala Lys Ser Ser Thr Asp Val Lys
1               5                  10
```

-continued

<210> SEQ ID NO 16
<211> LENGTH: 19
<212> TYPE: PRT
<213> ORGANISM: Unknown Organism
<220> FEATURE:
<223> OTHER INFORMATION: Description of Unknown Organism: Virus recognin

<400> SEQUENCE: 16

Lys Ser Ser Thr Asp Val Lys Ala Tyr Met Asp Lys Asp Gly Asp Val
 1               5                  10                  15

Leu Asp His

<210> SEQ ID NO 17
<211> LENGTH: 21
<212> TYPE: PRT
<213> ORGANISM: Unknown Organism
<220> FEATURE:
<223> OTHER INFORMATION: Description of Unknown Organism: Virus recognin

<400> SEQUENCE: 17

Lys Ala Ser Ala Leu Asn Ile Leu Arg Glu Lys Ala Pro Lys Asp Phe
 1               5                  10                  15

Val Leu Gln Phe His
            20

<210> SEQ ID NO 18
<211> LENGTH: 13
<212> TYPE: PRT
<213> ORGANISM: Hepatitis C virus

<400> SEQUENCE: 18

His Tyr Pro Pro Lys Pro Gly Cys Ile Val Pro Ala Lys
 1               5                  10

<210> SEQ ID NO 19
<211> LENGTH: 4
<212> TYPE: PRT
<213> ORGANISM: Homo sapiens

<400> SEQUENCE: 19

Tyr Lys Ala Gly
 1

<210> SEQ ID NO 20
<211> LENGTH: 6
<212> TYPE: PRT
<213> ORGANISM: Homo sapiens

<400> SEQUENCE: 20

Tyr Lys Ala Gly Val Ala
 1               5

<210> SEQ ID NO 21
<211> LENGTH: 7
<212> TYPE: PRT
<213> ORGANISM: Homo sapiens

<400> SEQUENCE: 21

Tyr Lys Ala Gly Val Ala Phe
 1               5

<210> SEQ ID NO 22
<211> LENGTH: 7
<212> TYPE: PRT
<213> ORGANISM: Homo sapiens

```
<400> SEQUENCE: 22

Tyr Lys Ala Gly Val Ala Phe
 1               5

<210> SEQ ID NO 23
<211> LENGTH: 9
<212> TYPE: PRT
<213> ORGANISM: Homo sapiens

<400> SEQUENCE: 23

Ala Gly Val Ala Phe His Lys Lys Asn
 1               5

<210> SEQ ID NO 24
<211> LENGTH: 4
<212> TYPE: PRT
<213> ORGANISM: Homo sapiens

<400> SEQUENCE: 24

Gly Val Ala Phe
 1

<210> SEQ ID NO 25
<211> LENGTH: 3
<212> TYPE: PRT
<213> ORGANISM: Homo sapiens

<400> SEQUENCE: 25

Val Ala Phe
 1

<210> SEQ ID NO 26
<211> LENGTH: 7
<212> TYPE: PRT
<213> ORGANISM: Homo sapiens

<400> SEQUENCE: 26

Val Ala Phe Leu His Lys Lys
 1               5

<210> SEQ ID NO 27
<211> LENGTH: 7
<212> TYPE: PRT
<213> ORGANISM: Homo sapiens

<400> SEQUENCE: 27

Val Ala Phe Leu His Lys Lys
 1               5

<210> SEQ ID NO 28
<211> LENGTH: 9
<212> TYPE: PRT
<213> ORGANISM: Homo sapiens

<400> SEQUENCE: 28

Val Ala Phe Leu His Lys Lys Asn Asp
 1               5

<210> SEQ ID NO 29
<211> LENGTH: 8
<212> TYPE: PRT
<213> ORGANISM: Homo sapiens

<400> SEQUENCE: 29
```

```
Val Ala Phe His Lys Lys Asn Asp
 1               5

<210> SEQ ID NO 30
<211> LENGTH: 4
<212> TYPE: PRT
<213> ORGANISM: Homo sapiens

<400> SEQUENCE: 30

Ala Phe Leu His
 1

<210> SEQ ID NO 31
<211> LENGTH: 8
<212> TYPE: PRT
<213> ORGANISM: Homo sapiens

<400> SEQUENCE: 31

His Lys Lys Asn Asp Ile Asp Glu
 1               5

<210> SEQ ID NO 32
<211> LENGTH: 6
<212> TYPE: PRT
<213> ORGANISM: Homo sapiens

<400> SEQUENCE: 32

Lys Lys Asn Asp Ile Asp
 1               5

<210> SEQ ID NO 33
<211> LENGTH: 6
<212> TYPE: PRT
<213> ORGANISM: Homo sapiens

<400> SEQUENCE: 33

Lys Asn Asp Ile Asp Glu
 1               5

<210> SEQ ID NO 34
<211> LENGTH: 8
<212> TYPE: PRT
<213> ORGANISM: Caldophera prolifera

<400> SEQUENCE: 34

Lys Ala Ser Lys Phe Thr Lys His
 1               5

<210> SEQ ID NO 35
<211> LENGTH: 12
<212> TYPE: PRT
<213> ORGANISM: Isolepis prolifera

<400> SEQUENCE: 35

Lys Ala Gln Ala Glu Thr Gly Glu Ile Lys Gly His
 1               5                  10

<210> SEQ ID NO 36
<211> LENGTH: 10
<212> TYPE: PRT
<213> ORGANISM: Schizosaccharomyces pombe

<400> SEQUENCE: 36

Lys Ser Phe Lys Tyr Pro Lys Lys His Lys
```

```
<210> SEQ ID NO 37
<211> LENGTH: 10
<212> TYPE: PRT
<213> ORGANISM: Oryza sativa

<400> SEQUENCE: 37

Lys Lys Ala Tyr Gly Asn Glu Leu His Lys
 1               5                  10

<210> SEQ ID NO 38
<211> LENGTH: 9
<212> TYPE: PRT
<213> ORGANISM: Penicillium marneffei

<400> SEQUENCE: 38

Lys Val Asp Ile Val Thr His Gln Lys
 1               5

<210> SEQ ID NO 39
<211> LENGTH: 12
<212> TYPE: PRT
<213> ORGANISM: Diseula dcstructiva

<400> SEQUENCE: 39

Lys Leu Glu Glu Asp Ala Ala Tyr His Arg Lys Lys
 1               5                  10

<210> SEQ ID NO 40
<211> LENGTH: 17
<212> TYPE: PRT
<213> ORGANISM: Ophiostoma novo-ulmi

<400> SEQUENCE: 40

Lys Val Ile Leu Pro Leu Arg Gly Asn Ile Lys Gly Ile Phe Phe Lys
 1               5                  10                  15

His

<210> SEQ ID NO 41
<211> LENGTH: 11
<212> TYPE: PRT
<213> ORGANISM: Entamoeba invadens

<400> SEQUENCE: 41

Lys Leu Ile Leu Lys Gly Asp Leu Asn Lys His
 1               5                  10

<210> SEQ ID NO 42
<211> LENGTH: 8
<212> TYPE: PRT
<213> ORGANISM: Helicobacter pylori

<400> SEQUENCE: 42

Lys Ser Val His Ala Phe Leu Lys
 1               5

<210> SEQ ID NO 43
<211> LENGTH: 9
<212> TYPE: PRT
<213> ORGANISM: Mycoplasma pulmonis

<400> SEQUENCE: 43

Lys Val His Phe Phe Gln Leu Lys Lys
```

```
<210> SEQ ID NO 44
<211> LENGTH: 9
<212> TYPE: PRT
<213> ORGANISM: Arabidopsis thaliana

<400> SEQUENCE: 44

Lys Asp His Asp Phe Asp Gly Asp Lys
1               5

<210> SEQ ID NO 45
<211> LENGTH: 11
<212> TYPE: PRT
<213> ORGANISM: Arabidopsis thaliana

<400> SEQUENCE: 45

Lys Met Lys Gly Leu Lys Gln Lys Lys Ala His
1               5                   10

<210> SEQ ID NO 46
<211> LENGTH: 12
<212> TYPE: PRT
<213> ORGANISM: Arabidopsis thaliana

<400> SEQUENCE: 46

Lys Glu Leu Ser Ser Thr Thr Gln Glu Lys Ser His
1               5                   10

<210> SEQ ID NO 47
<211> LENGTH: 9
<212> TYPE: PRT
<213> ORGANISM: Feline immunodeficiency virus

<400> SEQUENCE: 47

His Leu Lys Asp Tyr Lys Leu Val Lys
1               5

<210> SEQ ID NO 48
<211> LENGTH: 7
<212> TYPE: PRT
<213> ORGANISM: Rous sarcoma virus

<400> SEQUENCE: 48

Lys Lys Leu Arg His Glu Lys
1               5

<210> SEQ ID NO 49
<211> LENGTH: 7
<212> TYPE: PRT
<213> ORGANISM: Avian sarcoma virus

<400> SEQUENCE: 49

Lys Lys Leu Arg His Asp Lys
1               5

<210> SEQ ID NO 50
<211> LENGTH: 7
<212> TYPE: PRT
<213> ORGANISM: Homo sapiens

<400> SEQUENCE: 50

Lys Lys Leu Arg His Asp Lys
1               5
```

<210> SEQ ID NO 51
<211> LENGTH: 7
<212> TYPE: PRT
<213> ORGANISM: Avian sarcoma virus

<400> SEQUENCE: 51

Lys Lys Leu Arg His Glu Lys
1               5

<210> SEQ ID NO 52
<211> LENGTH: 7
<212> TYPE: PRT
<213> ORGANISM: Homo sapiens

<400> SEQUENCE: 52

Lys Lys Leu Arg His Glu Lys
1               5

<210> SEQ ID NO 53
<211> LENGTH: 8
<212> TYPE: PRT
<213> ORGANISM: Homo sapiens

<400> SEQUENCE: 53

Lys Gln Ala His Glu Leu Ala Lys
1               5

<210> SEQ ID NO 54
<211> LENGTH: 8
<212> TYPE: PRT
<213> ORGANISM: Polyama virus

<400> SEQUENCE: 54

Lys Thr His Arg Phe Ser Lys His
1               5

<210> SEQ ID NO 55
<211> LENGTH: 8
<212> TYPE: PRT
<213> ORGANISM: Sindbis virus

<400> SEQUENCE: 55

Lys Asn Leu His Glu Lys Ile Lys
1               5

<210> SEQ ID NO 56
<211> LENGTH: 9
<212> TYPE: PRT
<213> ORGANISM: Human papilloamavirus type 71

<400> SEQUENCE: 56

Lys His Arg Pro Leu Leu Gln Leu Lys
1               5

<210> SEQ ID NO 57
<211> LENGTH: 7
<212> TYPE: PRT
<213> ORGANISM: Avian encephalomyelitis virus

<400> SEQUENCE: 57

Lys Ser Pro Asn His Val Lys
1               5

<210> SEQ ID NO 58

```
<211> LENGTH: 8
<212> TYPE: PRT
<213> ORGANISM: Feline sarcoma virus

<400> SEQUENCE: 58

Lys Asn Ile His Leu Glu Lys Lys
 1               5

<210> SEQ ID NO 59
<211> LENGTH: 8
<212> TYPE: PRT
<213> ORGANISM: Homo sapiens

<400> SEQUENCE: 59

Lys Asn Ile His Leu Glu Lys Lys
 1               5

<210> SEQ ID NO 60
<211> LENGTH: 10
<212> TYPE: PRT
<213> ORGANISM: Polyoma virus

<400> SEQUENCE: 60

Lys Pro His Leu Ala Gln Ser Leu Glu Lys
 1               5                  10

<210> SEQ ID NO 61
<211> LENGTH: 9
<212> TYPE: PRT
<213> ORGANISM: Polyoma virus

<400> SEQUENCE: 61

Lys Gln His Arg Glu Leu Lys Asp Lys
 1               5

<210> SEQ ID NO 62
<211> LENGTH: 9
<212> TYPE: PRT
<213> ORGANISM: Polyoma virus

<400> SEQUENCE: 62

Lys Gln His Arg Glu Leu Lys Asp Lys
 1               5

<210> SEQ ID NO 63
<211> LENGTH: 12
<212> TYPE: PRT
<213> ORGANISM: Murine leukemia virus

<400> SEQUENCE: 63

Lys Val Pro Val Leu Ile Ser Pro Thr Leu Lys His
 1               5                  10

<210> SEQ ID NO 64
<211> LENGTH: 13
<212> TYPE: PRT
<213> ORGANISM: Human T-cell lymphotropic virus type 2

<400> SEQUENCE: 64

Lys Ser Leu Leu Leu Glu Val Asp Lys Asp Ile Ser His
 1               5                  10

<210> SEQ ID NO 65
<211> LENGTH: 13
<212> TYPE: PRT
```

-continued

<213> ORGANISM: Homo sapiens

<400> SEQUENCE: 65

Lys Ala Gly Ile Thr Ile Met Val Lys Arg Glu Tyr His
1               5                   10

<210> SEQ ID NO 66
<211> LENGTH: 8
<212> TYPE: PRT
<213> ORGANISM: Homo sapiens

<400> SEQUENCE: 66

Lys Ser Gly Lys His Leu Gly Lys
1               5

<210> SEQ ID NO 67
<211> LENGTH: 9
<212> TYPE: PRT
<213> ORGANISM: Homo sapiens

<400> SEQUENCE: 67

Lys Arg Arg Glu Gln Leu Lys His Lys
1               5

<210> SEQ ID NO 68
<211> LENGTH: 10
<212> TYPE: PRT
<213> ORGANISM: Homo sapiens

<400> SEQUENCE: 68

Lys Ser Phe Glu Val Ile Lys Val Ile His
1               5                   10

<210> SEQ ID NO 69
<211> LENGTH: 8
<212> TYPE: PRT
<213> ORGANISM: Homo sapiens

<400> SEQUENCE: 69

Lys Lys Lys His Thr Val Lys Lys
1               5

<210> SEQ ID NO 70
<211> LENGTH: 9
<212> TYPE: PRT
<213> ORGANISM: Homo sapiens

<400> SEQUENCE: 70

Lys Ala Gln Lys Asp His Leu Ser Lys
1               5

<210> SEQ ID NO 71
<211> LENGTH: 10
<212> TYPE: PRT
<213> ORGANISM: Homo sapiens

<400> SEQUENCE: 71

His Leu Lys Arg Val Lys Asp Leu Lys Lys
1               5                   10

<210> SEQ ID NO 72
<211> LENGTH: 11
<212> TYPE: PRT
<213> ORGANISM: Homo sapiens

```
<400> SEQUENCE: 72

Lys Tyr Gly Ser Pro Lys His Arg Leu Ile Lys
1               5                   10

<210> SEQ ID NO 73
<211> LENGTH: 13
<212> TYPE: PRT
<213> ORGANISM: Papilloma virus type 11

<400> SEQUENCE: 73

Lys Leu Lys His Ile Leu Gly Lys Ala Arg Phe Ile Lys
1               5                   10

<210> SEQ ID NO 74
<211> LENGTH: 12
<212> TYPE: PRT
<213> ORGANISM: Homo sapiens

<400> SEQUENCE: 74

Lys Gly Asp His Val Lys His Tyr Lys Ile Arg Lys
1               5                   10

<210> SEQ ID NO 75
<211> LENGTH: 13
<212> TYPE: PRT
<213> ORGANISM: Homo sapiens

<400> SEQUENCE: 75

Lys Glu Lys Leu Arg Asp Val Met Val Asp Arg His Lys
1               5                   10

<210> SEQ ID NO 76
<211> LENGTH: 15
<212> TYPE: PRT
<213> ORGANISM: Homo sapiens

<400> SEQUENCE: 76

Lys Leu Gln Ala Arg Gln Gln Leu Leu Lys Lys Ile Glu His
1               5                   10                  15

<210> SEQ ID NO 77
<211> LENGTH: 14
<212> TYPE: PRT
<213> ORGANISM: Homo sapiens

<400> SEQUENCE: 77

Lys Lys Gly Asn Arg Val Ser Pro Thr Met Lys Val Thr His
1               5                   10

<210> SEQ ID NO 78
<211> LENGTH: 9
<212> TYPE: PRT
<213> ORGANISM: Homo sapiens

<400> SEQUENCE: 78

Lys Glu Ile Pro Leu His Phe Arg Lys
1               5

<210> SEQ ID NO 79
<211> LENGTH: 8
<212> TYPE: PRT
<213> ORGANISM: Homo sapiens

<400> SEQUENCE: 79
```

```
Lys Lys Lys Pro His Ile Lys Lys
 1               5

<210> SEQ ID NO 80
<211> LENGTH: 9
<212> TYPE: PRT
<213> ORGANISM: Homo sapiens

<400> SEQUENCE: 80

Lys Thr Arg His Asp Pro Leu Ala Lys
 1               5

<210> SEQ ID NO 81
<211> LENGTH: 10
<212> TYPE: PRT
<213> ORGANISM: Homo sapiens

<400> SEQUENCE: 81

Lys His His Pro Lys Asp Asn Leu Ile Lys
 1               5                  10

<210> SEQ ID NO 82
<211> LENGTH: 10
<212> TYPE: PRT
<213> ORGANISM: Homo sapiens

<400> SEQUENCE: 82

Lys His Lys Arg Lys Lys Phe Arg Gln Lys
 1               5                  10

<210> SEQ ID NO 83
<211> LENGTH: 10
<212> TYPE: PRT
<213> ORGANISM: Homo sapiens

<400> SEQUENCE: 83

Lys Ala Gly Val Ala Phe Leu His Lys Lys
 1               5                  10

<210> SEQ ID NO 84
<211> LENGTH: 10
<212> TYPE: PRT
<213> ORGANISM: Homo sapiens

<400> SEQUENCE: 84

Lys His Lys Arg Lys Lys Phe Arg Gln Lys
 1               5                  10

<210> SEQ ID NO 85
<211> LENGTH: 10
<212> TYPE: PRT
<213> ORGANISM: Homo sapiens

<400> SEQUENCE: 85

Lys Lys Lys Ser Lys Lys His Lys Asp Lys
 1               5                  10

<210> SEQ ID NO 86
<211> LENGTH: 11
<212> TYPE: PRT
<213> ORGANISM: Homo sapiens

<400> SEQUENCE: 86

His Lys Ser Glu Lys Pro Ala Leu Pro Arg Lys
 1               5                  10
```

<210> SEQ ID NO 87
<211> LENGTH: 14
<212> TYPE: PRT
<213> ORGANISM: Homo sapiens

<400> SEQUENCE: 87

Lys Lys Lys Lys Pro Ser Arg Leu Lys Gly Asp Asn Glu Lys
1               5                   10

<210> SEQ ID NO 88
<211> LENGTH: 16
<212> TYPE: PRT
<213> ORGANISM: Homo sapiens

<400> SEQUENCE: 88

Lys Thr Lys Lys Gly Asn Arg Val Ser Pro Thr Met Lys Val Thr His
1               5                   10                  15

<210> SEQ ID NO 89
<211> LENGTH: 18
<212> TYPE: PRT
<213> ORGANISM: Homo sapiens

<400> SEQUENCE: 89

Lys His Lys Glu Lys Met Ser Lys Asp Gly Lys Lys Lys Lys Lys
1               5                   10                  15

Ser Lys

<210> SEQ ID NO 90
<211> LENGTH: 9
<212> TYPE: PRT
<213> ORGANISM: Legionella sp.

<400> SEQUENCE: 90

Lys Ile His Leu Ile Ser Val Lys Lys
1               5

<210> SEQ ID NO 91
<211> LENGTH: 10
<212> TYPE: PRT
<213> ORGANISM: Bacillus anthracis

<400> SEQUENCE: 91

His Val Lys Lys Glu Lys Glu Lys Asn Lys
1 5 10

<210> SEQ ID NO 92
<211> LENGTH: 9
<212> TYPE: PRT
<213> ORGANISM: Bacillus anthracis

<400> SEQUENCE: 92

Lys His Ile Val Lys Ile Glu Val Lys
1 5

<210> SEQ ID NO 93
<211> LENGTH: 16
<212> TYPE: PRT
<213> ORGANISM: Bacillus anthracis

<400> SEQUENCE: 93

Lys Lys Lys Lys Ile Lys Asp Ile Tyr Gly Lys Asp Ala Leu Leu His
1 5 10 15

<210> SEQ ID NO 94
<211> LENGTH: 8
<212> TYPE: PRT
<213> ORGANISM: Bacillus anthracis

<400> SEQUENCE: 94

Lys Trp Glu Lys Ile Lys Gln His
1               5

<210> SEQ ID NO 95
<211> LENGTH: 18
<212> TYPE: PRT
<213> ORGANISM: Bacillus anthracis

<400> SEQUENCE: 95

Lys Lys Leu Gln Ile Pro Pro Pro Ile Glu Pro Lys Lys Asp Asp Ile
1               5                   10                  15

Ile His

<210> SEQ ID NO 96
<211> LENGTH: 31
<212> TYPE: PRT
<213> ORGANISM: Bacillus anthracis

<400> SEQUENCE: 96

His Asn Arg Tyr Ala Ser Asn Ile Val Glu Ser Ala Tyr Leu Leu Ile
1               5                   10                  15

Leu Asn Glu Trp Lys Asn Asn Ile Gln Ser Asp Leu Ile Lys Lys
            20                  25                  30

<210> SEQ ID NO 97
<211> LENGTH: 24
<212> TYPE: PRT
<213> ORGANISM: Bacillus anthracis

<400> SEQUENCE: 97

His Ala Val Asp Asp Tyr Ala Gly Tyr Leu Leu Asp Lys Asn Gln Ser
1               5                   10                  15

Asp Leu Val Thr Asn Ser Lys Lys
            20

<210> SEQ ID NO 98
<211> LENGTH: 13
<212> TYPE: PRT
<213> ORGANISM: Bacillus anthracis

<400> SEQUENCE: 98

His Ala Glu Arg Leu Lys Val Gln Lys Asn Ala Pro Lys
1               5                   10

<210> SEQ ID NO 99
<211> LENGTH: 10
<212> TYPE: PRT
<213> ORGANISM: Variola virus

<400> SEQUENCE: 99

Lys His Tyr Asn Asn Ile Thr Trp Tyr Lys
1               5                   10

<210> SEQ ID NO 100
<211> LENGTH: 12
<212> TYPE: PRT

<213> ORGANISM: Variola virus

<400> SEQUENCE: 100

Lys Tyr Ser Gln Thr Gly Lys Glu Leu Ile Ile His
1               5                   10

<210> SEQ ID NO 101
<211> LENGTH: 17
<212> TYPE: PRT
<213> ORGANISM: Variola virus

<400> SEQUENCE: 101

His Tyr Asp Asp Val Arg Ile Lys Asn Asp Ile Val Val Ser Arg Cys
1               5                   10                  15
Lys

<210> SEQ ID NO 102
<211> LENGTH: 11
<212> TYPE: PRT
<213> ORGANISM: Variola virus

<400> SEQUENCE: 102

His Arg Phe Lys Leu Ile Leu Asp Ser Lys Ile
1               5                   10

<210> SEQ ID NO 103
<211> LENGTH: 11
<212> TYPE: PRT
<213> ORGANISM: Variola virus

<400> SEQUENCE: 103

Lys Glu Arg Gly His Asn Tyr Tyr Phe Glu Lys
1               5                   10

<210> SEQ ID NO 104
<211> LENGTH: 8
<212> TYPE: PRT
<213> ORGANISM: Influenza B virus

<400> SEQUENCE: 104

Lys Ser His Phe Ala Asn Leu Lys
1               5

<210> SEQ ID NO 105
<211> LENGTH: 11
<212> TYPE: PRT
<213> ORGANISM: Influenza B virus

<400> SEQUENCE: 105

Lys Ser His Phe Ala Asn Leu Lys Gly Thr Lys
1               5                   10

<210> SEQ ID NO 106
<211> LENGTH: 19
<212> TYPE: PRT
<213> ORGANISM: Influenza B virus

<400> SEQUENCE: 106

Lys Ser His Phe Ala Asn Leu Lys Gly Thr Lys Thr Arg Gly Lys Leu
1               5                   10                  15
Cys Pro Lys

<210> SEQ ID NO 107

```
<211> LENGTH: 9
<212> TYPE: PRT
<213> ORGANISM: Influenza B virus

<400> SEQUENCE: 107

His Glu Lys Tyr Gly Gly Leu Asn Lys
 1               5

<210> SEQ ID NO 108
<211> LENGTH: 11
<212> TYPE: PRT
<213> ORGANISM: Influenza B virus

<400> SEQUENCE: 108

His Glu Lys Tyr Gly Gly Leu Asn Lys Ser Lys
 1               5                  10

<210> SEQ ID NO 109
<211> LENGTH: 20
<212> TYPE: PRT
<213> ORGANISM: Influenza B virus

<400> SEQUENCE: 109

His Glu Lys Tyr Gly Gly Leu Asn Lys Ser Lys Pro Tyr Tyr Thr Gly
 1               5                  10                  15

Glu His Ala Lys
         20

<210> SEQ ID NO 110
<211> LENGTH: 13
<212> TYPE: PRT
<213> ORGANISM: Influenza B virus

<400> SEQUENCE: 110

His Ala Lys Ala Ile Gly Asn Cys Pro Ile Trp Val Lys
 1               5                  10

<210> SEQ ID NO 111
<211> LENGTH: 23
<212> TYPE: PRT
<213> ORGANISM: Influenza B virus

<400> SEQUENCE: 111

His Ala Lys Ala Ile Gly Asn Cys Pro Ile Trp Val Lys Thr Pro Leu
 1               5                  10                  15

Lys Leu Ala Asn Gly Thr Lys
         20

<210> SEQ ID NO 112
<211> LENGTH: 29
<212> TYPE: PRT
<213> ORGANISM: Influenza B virus

<400> SEQUENCE: 112

His Ala Lys Ala Ile Gly Asn Cys Pro Ile Trp Val Lys Thr Pro Leu
 1               5                  10                  15

Lys Leu Ala Asn Gly Thr Lys Tyr Arg Pro Pro Ala Lys
         20                  25

<210> SEQ ID NO 113
<211> LENGTH: 32
<212> TYPE: PRT
<213> ORGANISM: Influenza B virus
```

```
<400> SEQUENCE: 113

His Ala Lys Ala Ile Gly Asn Cys Pro Ile Trp Val Lys Thr Pro Leu
1               5                   10                  15

Lys Leu Ala Asn Gly Thr Lys Tyr Arg Pro Pro Ala Lys Leu Leu Lys
            20                  25                  30

<210> SEQ ID NO 114
<211> LENGTH: 13
<212> TYPE: PRT
<213> ORGANISM: Influenza B virus

<400> SEQUENCE: 114

His Phe Ala Asn Leu Lys Gly Thr Lys Thr Arg Gly Lys
1               5                   10

<210> SEQ ID NO 115
<211> LENGTH: 17
<212> TYPE: PRT
<213> ORGANISM: Influenza B virus

<400> SEQUENCE: 115

His Phe Ala Asn Leu Lys Gly Thr Lys Thr Arg Gly Lys Leu Cys Pro
1               5                   10                  15

Lys

<210> SEQ ID NO 116
<211> LENGTH: 16
<212> TYPE: PRT
<213> ORGANISM: Influenza B virus

<400> SEQUENCE: 116

His Ser Asp Asn Glu Ile Gln Met Val Lys Leu Tyr Gly Asp Ser Lys
1               5                   10                  15

<210> SEQ ID NO 117
<211> LENGTH: 21
<212> TYPE: PRT
<213> ORGANISM: Influenza B virus

<400> SEQUENCE: 117

His Ser Asp Asn Glu Ile Gln Asp Lys Met Val Lys Leu Tyr Gly Asp
1               5                   10                  15

Ser Lys Pro Gln Lys
            20

<210> SEQ ID NO 118
<211> LENGTH: 19
<212> TYPE: PRT
<213> ORGANISM: Influenza B virus

<400> SEQUENCE: 118

His Ser Asp Asn Glu Ile Gln Met Val Lys Leu Tyr Gly Asp Ser Lys
1               5                   10                  15

Pro Gln Lys

<210> SEQ ID NO 119
<211> LENGTH: 9
<212> TYPE: PRT
<213> ORGANISM: Influenza B virus
<220> FEATURE:
<221> NAME/KEY: MOD_RES
<222> LOCATION: (2)
<223> OTHER INFORMATION: ala or val
```

```
<400> SEQUENCE: 119

Lys Xaa Ser Ile Leu His Glu Val Lys
1               5

<210> SEQ ID NO 120
<211> LENGTH: 15
<212> TYPE: PRT
<213> ORGANISM: Influenza B virus

<400> SEQUENCE: 120

Lys Cys Thr Gly Thr Ile Pro Ser Ala Lys Ala Ser Ile Leu His
1               5                   10                  15

<210> SEQ ID NO 121
<211> LENGTH: 18
<212> TYPE: PRT
<213> ORGANISM: Influenza B virus

<400> SEQUENCE: 121

Lys Cys Thr Gly Thr Ile Pro Ser Ala Lys Ala Ser Ile Leu His Glu
1               5                   10                  15

Val Lys

<210> SEQ ID NO 122
<211> LENGTH: 16
<212> TYPE: PRT
<213> ORGANISM: Influenza B virus

<400> SEQUENCE: 122

Lys Tyr Gly Gly Leu Asn Lys Ser Lys Pro Tyr Tyr Thr Gly Glu His
1               5                   10                  15

<210> SEQ ID NO 123
<211> LENGTH: 26
<212> TYPE: PRT
<213> ORGANISM: Influenza B virus

<400> SEQUENCE: 123

Lys Val Trp Cys Ala Ser Gly Arg Ser Lys Val Ile Lys Gly Ser Leu
1               5                   10                  15

Pro Leu Ile Gly Glu Ala Asp Cys Leu His
            20                  25

<210> SEQ ID NO 124
<211> LENGTH: 10
<212> TYPE: PRT
<213> ORGANISM: Influenza B virus

<400> SEQUENCE: 124

Lys Pro Tyr Tyr Thr Gly Glu His Ala Lys
1               5                   10

<210> SEQ ID NO 125
<211> LENGTH: 18
<212> TYPE: PRT
<213> ORGANISM: Influenza B virus

<400> SEQUENCE: 125

Lys Cys Met Gly Thr Ile Pro Ser Ala Lys Ala Ser Ile Leu His Glu
1               5                   10                  15

Val Lys
```

```
<210> SEQ ID NO 126
<211> LENGTH: 15
<212> TYPE: PRT
<213> ORGANISM: Influenza B virus

<400> SEQUENCE: 126

His Asn Val Ile Asn Ala Glu Lys Ala Pro Gly Gly Pro Tyr Lys
1               5                   10                  15

<210> SEQ ID NO 127
<211> LENGTH: 16
<212> TYPE: PRT
<213> ORGANISM: Influenza B virus

<400> SEQUENCE: 127

His Ser Asp Asn Glu Thr Gln Met Ala Lys Leu Tyr Gly Asp Ser Lys
1               5                   10                  15

<210> SEQ ID NO 128
<211> LENGTH: 18
<212> TYPE: PRT
<213> ORGANISM: Influenza B virus

<400> SEQUENCE: 128

His Gly Val Ala Val Ala Ala Asp Leu Lys Ser Thr Gln Glu Ala Ile
1               5                   10                  15

Asn Lys

<210> SEQ ID NO 129
<211> LENGTH: 29
<212> TYPE: PRT
<213> ORGANISM: Influenza B virus

<400> SEQUENCE: 129

His Gly Val Ala Val Ala Ala Asp Leu Lys Ser Thr Gln Glu Ala Ile
1               5                   10                  15

Asn Lys Asp Thr Ile Ser Thr Gln Glu Ala Ile Asn Lys
            20                  25

<210> SEQ ID NO 130
<211> LENGTH: 21
<212> TYPE: PRT
<213> ORGANISM: Influenza B virus

<400> SEQUENCE: 130

Lys Leu Tyr Gly Asp Ser Lys Pro Gln Lys Phe Thr Ser Ser Ala Asn
1               5                   10                  15

Gly Val Thr Thr His
            20

<210> SEQ ID NO 131
<211> LENGTH: 19
<212> TYPE: PRT
<213> ORGANISM: Influenza B virus

<400> SEQUENCE: 131

His Ser Asp Asn Glu Thr Gln Met Ala Lys Leu Tyr Gly Asp Ser Lys
1               5                   10                  15

Pro Gln Lys

<210> SEQ ID NO 132
<211> LENGTH: 13
```

```
<212> TYPE: PRT
<213> ORGANISM: Influenza B virus

<400> SEQUENCE: 132

His Phe Ala Asn Leu Lys Gly Thr Gln Thr Arg Gly Lys
1               5                   10

<210> SEQ ID NO 133
<211> LENGTH: 12
<212> TYPE: PRT
<213> ORGANISM: Influenza B virus

<400> SEQUENCE: 133

Lys Pro Arg Ser Ala Leu Lys Cys Lys Gly Phe His
1               5                   10

<210> SEQ ID NO 134
<211> LENGTH: 22
<212> TYPE: PRT
<213> ORGANISM: Influenza B virus
<220> FEATURE:
<221> NAME/KEY: MOD_RES
<222> LOCATION: (15)
<223> OTHER INFORMATION: gly or ala

<400> SEQUENCE: 134

Lys Ser Lys Pro Tyr Tyr Thr Gly Glu His Ala Lys Ala Ile Xaa Asn
1               5                   10                  15
Cys Pro Ile Trp Val Lys
            20

<210> SEQ ID NO 135
<211> LENGTH: 16
<212> TYPE: PRT
<213> ORGANISM: Influenza virus
<220> FEATURE:
<221> NAME/KEY: MOD_RES
<222> LOCATION: (3)
<223> OTHER INFORMATION: val or ile
<220> FEATURE:
<221> NAME/KEY: MOD_RES
<222> LOCATION: (13)
<223> OTHER INFORMATION: arg or lys
<220> FEATURE:
<221> NAME/KEY: MOD_RES
<222> LOCATION: (14)
<223> OTHER INFORMATION: ser or thr
<220> FEATURE:
<221> NAME/KEY: MOD_RES
<222> LOCATION: (15)
<223> OTHER INFORMATION: thr or ala

<400> SEQUENCE: 135

His Pro Xaa Thr Ile Gly Glu Cys Pro Lys Tyr Val Xaa Xaa Xaa Lys
1               5                   10                  15

<210> SEQ ID NO 136
<211> LENGTH: 21
<212> TYPE: PRT
<213> ORGANISM: Influenza virus
<220> FEATURE:
<221> NAME/KEY: MOD_RES
<222> LOCATION: (10)
<223> OTHER INFORMATION: glu or gly
<220> FEATURE:
<221> NAME/KEY: MOD_RES
<222> LOCATION: (13)
<223> OTHER INFORMATION: lys or arg
<220> FEATURE:
<221> NAME/KEY: MOD_RES
```

```
<222> LOCATION: (14)
<223> OTHER INFORMATION: asn or ser
<220> FEATURE:
<221> NAME/KEY: MOD_RES
<222> LOCATION: (17)
<223> OTHER INFORMATION: lys or arg

<400> SEQUENCE: 136

His Asp Ser Asn Val Lys Asn Leu Tyr Xaa Lys Val Xaa Xaa Gln Leu
 1               5                  10                  15

Xaa Asn Asn Ala Lys
             20

<210> SEQ ID NO 137
<211> LENGTH: 17
<212> TYPE: PRT
<213> ORGANISM: Influenza virus
<220> FEATURE:
<221> NAME/KEY: MOD_RES
<222> LOCATION: (10)
<223> OTHER INFORMATION: glu or gly
<220> FEATURE:
<221> NAME/KEY: MOD_RES
<222> LOCATION: (13)
<223> OTHER INFORMATION: lys or arg
<220> FEATURE:
<221> NAME/KEY: MOD_RES
<222> LOCATION: (14)
<223> OTHER INFORMATION: asn or ser

<400> SEQUENCE: 137

His Asp Ser Asn Val Lys Asn Leu Tyr Xaa Lys Val Xaa Xaa Gln Leu
 1               5                  10                  15

Lys

<210> SEQ ID NO 138
<211> LENGTH: 36
<212> TYPE: PRT
<213> ORGANISM: Influenza virus
<220> FEATURE:
<221> NAME/KEY: MOD_RES
<222> LOCATION: (4)..(5)
<223> OTHER INFORMATION: asn or asp
<220> FEATURE:
<221> NAME/KEY: MOD_RES
<222> LOCATION: (6)
<223> OTHER INFORMATION: ala, thr or glu
<220> FEATURE:
<221> NAME/KEY: MOD_RES
<222> LOCATION: (12)
<223> OTHER INFORMATION: arg or lys
<220> FEATURE:
<221> NAME/KEY: MOD_RES
<222> LOCATION: (31)
<223> OTHER INFORMATION: glu or lys

<400> SEQUENCE: 138

His Lys Cys Xaa Xaa Xaa Cys Met Glu Ser Val Xaa Asn Gly Thr Tyr
 1               5                  10                  15

Asp Tyr Pro Lys Tyr Ser Glu Glu Ser Lys Leu Asn Arg Glu Xaa Ile
             20                  25                  30

Asp Gly Val Lys
         35

<210> SEQ ID NO 139
<211> LENGTH: 26
<212> TYPE: PRT
<213> ORGANISM: Influenza virus
<220> FEATURE:
```

```
<221> NAME/KEY: MOD_RES
<222> LOCATION: (4)..(5)
<223> OTHER INFORMATION: asn or asp
<220> FEATURE:
<221> NAME/KEY: MOD_RES
<222> LOCATION: (6)
<223> OTHER INFORMATION: ala, thr or glu
<220> FEATURE:
<221> NAME/KEY: MOD_RES
<222> LOCATION: (12)
<223> OTHER INFORMATION: arg or lys

<400> SEQUENCE: 139

His Lys Cys Xaa Xaa Xaa Cys Met Glu Ser Val Xaa Asn Gly Thr Tyr
 1               5                  10                  15

Asp Tyr Pro Lys Tyr Ser Glu Glu Ser Lys
            20                  25

<210> SEQ ID NO 140
<211> LENGTH: 50
<212> TYPE: PRT
<213> ORGANISM: Influenza virus
<220> FEATURE:
<221> NAME/KEY: MOD_RES
<222> LOCATION: (4)
<223> OTHER INFORMATION: glu or gly
<220> FEATURE:
<221> NAME/KEY: MOD_RES
<222> LOCATION: (21)
<223> OTHER INFORMATION: asp or asn

<400> SEQUENCE: 140

His Gln Asn Xaa Gln Gly Ser Gly Tyr Ala Ala Asp Gln Lys Ser Thr
 1               5                  10                  15

Gln Asn Ala Ile Xaa Gly Ile Thr Asn Lys Val Asn Ser Val Ile Glu
            20                  25                  30

Lys Met Asn Thr Gln Phe Thr Ala Val Gly Lys Glu Phe Asn Lys Leu
        35                  40                  45

Glu Lys
    50

<210> SEQ ID NO 141
<211> LENGTH: 33
<212> TYPE: PRT
<213> ORGANISM: Influenza virus
<220> FEATURE:
<221> NAME/KEY: MOD_RES
<222> LOCATION: (4)
<223> OTHER INFORMATION: glu or gly
<220> FEATURE:
<221> NAME/KEY: MOD_RES
<222> LOCATION: (21)
<223> OTHER INFORMATION: asp or asn

<400> SEQUENCE: 141

His Gln Asn Xaa Gln Gly Ser Gly Tyr Ala Ala Asp Gln Lys Ser Thr
 1               5                  10                  15

Gln Asn Ala Ile Xaa Gly Ile Thr Asn Lys Val Asn Ser Val Ile Glu
            20                  25                  30

Lys

<210> SEQ ID NO 142
<211> LENGTH: 26
<212> TYPE: PRT
<213> ORGANISM: Influenza virus
<220> FEATURE:
<221> NAME/KEY: MOD_RES
```

```
<222> LOCATION: (4)
<223> OTHER INFORMATION: glu or gly
<220> FEATURE:
<221> NAME/KEY: MOD_RES
<222> LOCATION: (21)
<223> OTHER INFORMATION: asp or asn

<400> SEQUENCE: 142

His Gln Asn Xaa Gln Gly Ser Gly Tyr Ala Ala Asp Gln Lys Ser Thr
 1               5                  10                  15

Gln Asn Ala Ile Xaa Gly Ile Thr Asn Lys
            20                  25

<210> SEQ ID NO 143
<211> LENGTH: 14
<212> TYPE: PRT
<213> ORGANISM: Influenza virus

<400> SEQUENCE: 143

Lys Phe Glu Ile Phe Pro Lys Thr Ser Ser Trp Pro Asn His
 1               5                  10

<210> SEQ ID NO 144
<211> LENGTH: 27
<212> TYPE: PRT
<213> ORGANISM: Influenza virus
<220> FEATURE:
<221> NAME/KEY: MOD_RES
<222> LOCATION: (3)
<223> OTHER INFORMATION: asn, ser or thr
<220> FEATURE:
<221> NAME/KEY: MOD_RES
<222> LOCATION: (9)
<223> OTHER INFORMATION: asn or ser
<220> FEATURE:
<221> NAME/KEY: MOD_RES
<222> LOCATION: (13)
<223> OTHER INFORMATION: val or thr

<400> SEQUENCE: 144

Lys Gly Xaa Ser Tyr Pro Lys Leu Xaa Lys Ser Tyr Xaa Asn Asn Lys
 1               5                  10                  15

Gly Lys Glu Val Leu Val Leu Trp Gly Val His
            20                  25

<210> SEQ ID NO 145
<211> LENGTH: 18
<212> TYPE: PRT
<213> ORGANISM: Influenza virus
<220> FEATURE:
<221> NAME/KEY: MOD_RES
<222> LOCATION: (4)
<223> OTHER INFORMATION: val or thr

<400> SEQUENCE: 145

Lys Ser Tyr Xaa Asn Asn Lys Gly Lys Glu Val Leu Val Leu Trp Gly
 1               5                  10                  15

Val His

<210> SEQ ID NO 146
<211> LENGTH: 36
<212> TYPE: PRT
<213> ORGANISM: Influenza virus

<400> SEQUENCE: 146

His Lys Cys Asn Asn Glu Cys Met Glu Ser Val Lys Asn Gly Thr Tyr
 1               5                  10                  15
```

```
Asp Tyr Pro Lys Tyr Ser Glu Glu Ser Lys Leu Asn Arg Glu Lys Ile
            20                  25                  30

Asp Gly Val Lys
        35

<210> SEQ ID NO 147
<211> LENGTH: 26
<212> TYPE: PRT
<213> ORGANISM: Influenza virus

<400> SEQUENCE: 147

His Lys Cys Asn Asn Glu Cys Met Glu Ser Val Lys Asn Gly Thr Tyr
1               5                   10                  15

Asp Tyr Pro Lys Tyr Ser Glu Glu Ser Lys
            20                  25

<210> SEQ ID NO 148
<211> LENGTH: 20
<212> TYPE: PRT
<213> ORGANISM: Influenza virus

<400> SEQUENCE: 148

His Lys Cys Asn Asn Glu Cys Met Glu Ser Val Lys Asn Gly Thr Tyr
1               5                   10                  15

Asp Tyr Pro Lys
            20

<210> SEQ ID NO 149
<211> LENGTH: 12
<212> TYPE: PRT
<213> ORGANISM: Influenza virus

<400> SEQUENCE: 149

His Lys Cys Asn Asn Glu Cys Met Glu Ser Val Lys
1               5                   10

<210> SEQ ID NO 150
<211> LENGTH: 34
<212> TYPE: PRT
<213> ORGANISM: Influenza virus
<220> FEATURE:
<221> NAME/KEY: MOD_RES
<222> LOCATION: (9)
<223> OTHER INFORMATION: lys or arg
<220> FEATURE:
<221> NAME/KEY: MOD_RES
<222> LOCATION: (16)
<223> OTHER INFORMATION: glu or gly

<400> SEQUENCE: 150

His Asn Gly Lys Ser Ser Phe Tyr Xaa Asn Leu Leu Trp Leu Thr Xaa
1               5                   10                  15

Lys Asn Gly Leu Tyr Pro Asn Leu Ser Lys Ser Tyr Val Asn Asn Lys
            20                  25                  30

Glu Lys

<210> SEQ ID NO 151
<211> LENGTH: 32
<212> TYPE: PRT
<213> ORGANISM: Influenza virus
<220> FEATURE:
<221> NAME/KEY: MOD_RES
<222> LOCATION: (9)
<223> OTHER INFORMATION: lys or arg
```

```
<220> FEATURE:
<221> NAME/KEY: MOD_RES
<222> LOCATION: (16)
<223> OTHER INFORMATION: glu or gly

<400> SEQUENCE: 151

His Asn Gly Lys Ser Ser Phe Tyr Xaa Asn Leu Leu Trp Leu Thr Xaa
 1               5                  10                  15
Lys Asn Gly Leu Tyr Pro Asn Leu Ser Lys Ser Tyr Val Asn Asn Lys
            20                  25                  30

<210> SEQ ID NO 152
<211> LENGTH: 26
<212> TYPE: PRT
<213> ORGANISM: Influenza virus
<220> FEATURE:
<221> NAME/KEY: MOD_RES
<222> LOCATION: (9)
<223> OTHER INFORMATION: lys or arg
<220> FEATURE:
<221> NAME/KEY: MOD_RES
<222> LOCATION: (16)
<223> OTHER INFORMATION: glu or gly

<400> SEQUENCE: 152

His Asn Gly Lys Ser Ser Phe Tyr Xaa Asn Leu Leu Trp Leu Thr Xaa
 1               5                  10                  15
Lys Asn Gly Leu Tyr Pro Asn Leu Ser Lys
            20                  25

<210> SEQ ID NO 153
<211> LENGTH: 17
<212> TYPE: PRT
<213> ORGANISM: Influenza virus
<220> FEATURE:
<221> NAME/KEY: MOD_RES
<222> LOCATION: (9)
<223> OTHER INFORMATION: lys or arg
<220> FEATURE:
<221> NAME/KEY: MOD_RES
<222> LOCATION: (16)
<223> OTHER INFORMATION: glu or gly

<400> SEQUENCE: 153

His Asn Gly Lys Ser Ser Phe Tyr Xaa Asn Leu Leu Trp Leu Thr Xaa
 1               5                  10                  15
Lys

<210> SEQ ID NO 154
<211> LENGTH: 40
<212> TYPE: PRT
<213> ORGANISM: Influenza virus

<400> SEQUENCE: 154

Lys Ser Ser Phe Tyr Lys Asn Leu Leu Trp Leu Thr Glu Lys Asn Gly
 1               5                  10                  15
Leu Tyr Pro Asn Leu Ser Lys Ser Tyr Val Asn Asn Lys Glu Lys Glu
            20                  25                  30
Val Leu Val Leu Trp Gly Val His
            35                  40

<210> SEQ ID NO 155
<211> LENGTH: 35
<212> TYPE: PRT
<213> ORGANISM: Influenza virus
```

```
<400> SEQUENCE: 155

Lys Asn Leu Leu Trp Leu Thr Glu Lys Asn Gly Leu Tyr Pro Asn Leu
1               5                   10                  15

Ser Lys Ser Tyr Val Asn Asn Lys Glu Lys Glu Val Leu Val Leu Trp
            20                  25                  30

Gly Val His
        35

<210> SEQ ID NO 156
<211> LENGTH: 27
<212> TYPE: PRT
<213> ORGANISM: Influenza virus

<400> SEQUENCE: 156

Lys Asn Gly Leu Tyr Pro Asn Leu Ser Lys Ser Tyr Val Asn Asn Lys
1               5                   10                  15

Glu Lys Glu Val Leu Val Leu Trp Gly Val His
            20                  25

<210> SEQ ID NO 157
<211> LENGTH: 18
<212> TYPE: PRT
<213> ORGANISM: Influenza virus
<220> FEATURE:
<221> NAME/KEY: MOD_RES
<222> LOCATION: (4)
<223> OTHER INFORMATION: val or ala
<220> FEATURE:
<221> NAME/KEY: MOD_RES
<222> LOCATION: (12)
<223> OTHER INFORMATION: lys or not present
<220> FEATURE:
<221> NAME/KEY: MOD_RES
<222> LOCATION: (13)
<223> OTHER INFORMATION: val or not present

<400> SEQUENCE: 157

Lys Ser Tyr Xaa Asn Asn Lys Glu Lys Glu Val Xaa Xaa Leu Trp Gly
1               5                   10                  15

Val His

<210> SEQ ID NO 158
<211> LENGTH: 12
<212> TYPE: PRT
<213> ORGANISM: Influenza virus

<400> SEQUENCE: 158

Lys Glu Ser Ser Trp Pro Asn His Thr Val Thr Lys
1               5                   10

<210> SEQ ID NO 159
<211> LENGTH: 44
<212> TYPE: PRT
<213> ORGANISM: Influenza virus
<220> FEATURE:
<221> NAME/KEY: MOD_RES
<222> LOCATION: (4)
<223> OTHER INFORMATION: thr or asn

<400> SEQUENCE: 159

His Glu Thr Xaa Lys Gly Val Thr Ala Ala Cys Pro Tyr Ala Gly Ala
1               5                   10                  15

Ser Ser Phe Tyr Arg Asn Leu Leu Trp Leu Val Lys Lys Glu Asn Ser
            20                  25                  30
```

Tyr Pro Lys Leu Ser Lys Ser Tyr Val Asn Asn Lys
        35                  40

<210> SEQ ID NO 160
<211> LENGTH: 38
<212> T

```
<220> FEATURE:
<221> NAME/KEY: MOD_RES
<222> LOCATION: (2)
<223> OTHER INFORMATION: lys or asn
<220> FEATURE:
<221> NAME/KEY: MOD_RES
<222> LOCATION: (3)
<223> OTHER INFORMATION: gly or gln
<220> FEATURE:
<221> NAME/KEY: MOD_RES
<222> LOCATION: (9)
<223> OTHER INFORMATION: arg or lys
<220> FEATURE:
<221> NAME/KEY: MOD_RES
<222> LOCATION: (20)
<223> OTHER INFORMATION: lys or ser
<220> FEATURE:
<221> NAME/KEY: MOD_RES
<222> LOCATION: (23)
<223> OTHER INFORMATION: asn or thr

<400> SEQUENCE: 165

His Xaa Xaa Lys Ser Ser Phe Tyr Xaa Asn Leu Leu Trp Leu Thr Glu
 1               5                  10                  15

Lys Asn Gly Xaa Tyr Pro Xaa Leu Ser Lys Ser Tyr Ala Asn Asn Lys
            20                  25                  30

Glu Lys

<210> SEQ ID NO 166
<211> LENGTH: 17
<212> TYPE: PRT
<213> ORGANISM: Influenza virus
<220> FEATURE:
<221> NAME/KEY: MOD_RES
<222> LOCATION: (2)
<223> OTHER INFORMATION: lys or asn
<220> FEATURE:
<221> NAME/KEY: MOD_RES
<222> LOCATION: (3)
<223> OTHER INFORMATION: gly or gln
<220> FEATURE:
<221> NAME/KEY: MOD_RES
<222> LOCATION: (9)
<223> OTHER INFORMATION: arg or lys

<400> SEQUENCE: 166

His Xaa Xaa Lys Ser Ser Phe Tyr Xaa Asn Leu Leu Trp Leu Thr Glu
 1               5                  10                  15

Lys

<210> SEQ ID NO 167
<211> LENGTH: 9
<212> TYPE: PRT
<213> ORGANISM: Influenza virus

<400> SEQUENCE: 167

His Ala Lys Lys Ser Ser Phe Tyr Lys
 1               5

<210> SEQ ID NO 168
<211> LENGTH: 11
<212> TYPE: PRT
<213> ORGANISM: Influenza virus

<400> SEQUENCE: 168

His Asn Gly Lys Leu Cys Arg Leu Lys Gly Lys
 1               5                  10
```

```
<210> SEQ ID NO 169
<211> LENGTH: 9
<212> TYPE: PRT
<213> ORGANISM: Influenza virus
<220> FEATURE:
<221> NAME/KEY: MOD_RES
<222> LOCATION: (7)
<223> OTHER INFORMATION: gln or gly

<400> SEQUENCE: 169

His Tyr Lys Leu Asn Asn Xaa Lys Lys
 1               5

<210> SEQ ID NO 170
<211> LENGTH: 25
<212> TYPE: PRT
<213> ORGANISM: Influenza virus

<400> SEQUENCE: 170

His Asp Ile Tyr Arg Asp Glu Ala Ile Asn Asn Arg Phe Gln Ile Gln
 1               5                  10                  15

Gly Val Lys Leu Thr Gln Gly Tyr Lys
            20                  25

<210> SEQ ID NO 171
<211> LENGTH: 11
<212> TYPE: PRT
<213> ORGANISM: Influenza virus

<400> SEQUENCE: 171

Lys Gly Asn Gly Cys Phe Glu Ile Phe His Lys
 1               5                  10

<210> SEQ ID NO 172
<211> LENGTH: 18
<212> TYPE: PRT
<213> ORGANISM: Influenza virus

<400> SEQUENCE: 172

Lys Leu Asn Arg Leu Ile Glu Lys Thr Asn Asp Lys Tyr His Gln Ile
 1               5                  10                  15

Glu Lys

<210> SEQ ID NO 173
<211> LENGTH: 14
<212> TYPE: PRT
<213> ORGANISM: Influenza virus

<400> SEQUENCE: 173

Lys Leu Asn Arg Leu Ile Glu Lys Thr Asn Asp Lys Tyr His
 1               5                  10

<210> SEQ ID NO 174
<211> LENGTH: 13
<212> TYPE: PRT
<213> ORGANISM: Influenza virus

<400> SEQUENCE: 174

Lys Cys His Thr Asp Lys Gly Ser Leu Ser Thr Thr Lys
 1               5                  10

<210> SEQ ID NO 175
<211> LENGTH: 16
<212> TYPE: PRT
<213> ORGANISM: Influenza virus
```

```
<400> SEQUENCE: 175

Lys Ile Asn Asn Gly Asp Tyr Ala Lys Leu Tyr Ile Trp Gly Val His
1               5                   10                  15

<210> SEQ ID NO 176
<211> LENGTH: 17
<212> TYPE: PRT
<213> ORGANISM: Influenza virus

<400> SEQUENCE: 176

His Asn Gly Lys Leu Cys Arg Lys Gly Ile Ala Pro Leu Gln Leu Gly
1               5                   10                  15

Lys

<210> SEQ ID NO 177
<211> LENGTH: 38
<212> TYPE: PRT
<213> ORGANISM: Influenza virus

<400> SEQUENCE: 177

His Glu Thr Asn Arg Gln Val Thr Ala Ala Cys Pro Tyr Ala Gly Ala
1               5                   10                  15

Asn Ser Phe Phe Arg Asn Leu Ile Trp Leu Val Lys Lys Glu Ser Ser
                20                  25                  30

Tyr Pro Lys Leu Ser Lys
        35

<210> SEQ ID NO 178
<211> LENGTH: 35
<212> TYPE: PRT
<213> ORGANISM: Influenza virus

<400> SEQUENCE: 178

His Glu Thr Asn Arg Gln Val Thr Ala Ala Cys Pro Tyr Ala Gly Ala
1               5                   10                  15

Asn Ser Phe Phe Arg Asn Leu Ile Trp Leu Val Lys Lys Glu Ser Ser
                20                  25                  30

Tyr Pro Lys
        35

<210> SEQ ID NO 179
<211> LENGTH: 31
<212> TYPE: PRT
<213> ORGANISM: Influenza virus

<400> SEQUENCE: 179

His Pro Pro Thr Ser Thr Asp Gln Gln Ser Leu Tyr Gln Asn Ala Asp
1               5                   10                  15

Ala Tyr Ile Phe Val Gly Ser Ser Lys Tyr Asn Arg Lys Phe Lys
                20                  25                  30

<210> SEQ ID NO 180
<211> LENGTH: 35
<212> TYPE: PRT
<213> ORGANISM: Influenza virus

<400> SEQUENCE: 180

His Pro Pro Thr Ser Thr Asp Gln Gln Ser Leu Tyr Gln Asn Ala Asp
1               5                   10                  15

Ala Tyr Ile Phe Val Gly Ser Ser Lys Tyr Asn Arg Lys Phe Lys Pro
```

```
                    20                  25                  30

Glu Ile Ala
        35

<210> SEQ ID NO 181
<211> LENGTH: 25
<212> TYPE: PRT
<213> ORGANISM: Influenza virus

<400> SEQUENCE: 181

His Asp Ile Tyr Arg Asp Glu Ala Ile Asn Asn Arg Phe Gln Ile Gln
1               5                   10                  15

Gly Val Lys Ile Thr Gln Gly Tyr Lys
            20                  25

<210> SEQ ID NO 182
<211> LENGTH: 43
<212> TYPE: PRT
<213> ORGANISM: Influenza virus

<400> SEQUENCE: 182

His Gln Asn Glu Gln Gly Ser Gly Tyr Ala Ala Asp Gln Lys Ser Thr
1               5                   10                  15

Gln Asn Ala Ile Asp Gly Ile Thr Asn Lys Val Asn Ser Val Ile Glu
            20                  25                  30

Lys Met Asn Thr Gln Phe Thr Ala Val Gly Lys
        35                  40

<210> SEQ ID NO 183
<211> LENGTH: 33
<212> TYPE: PRT
<213> ORGANISM: Influenza virus

<400> SEQUENCE: 183

His Gln Asn Glu Gln Gly Ser Gly Tyr Ala Ala Asp Gln Lys Ser Thr
1               5                   10                  15

Gln Asn Ala Ile Asp Gly Ile Thr Asn Lys Val Asn Ser Val Ile Glu
            20                  25                  30

Lys

<210> SEQ ID NO 184
<211> LENGTH: 50
<212> TYPE: PRT
<213> ORGANISM: Influenza virus

<400> SEQUENCE: 184

His Gln Asn Glu Gln Gly Ser Gly Tyr Ala Ala Asp Gln Lys Ser Thr
1               5                   10                  15

Gln Asn Ala Ile Asn Gly Ile Thr Asn Lys Val Asn Ser Val Ile Glu
            20                  25                  30

Lys Met Asn Thr Gln Phe Thr Ala Val Gly Lys Glu Phe Asn Lys Leu
        35                  40                  45

Glu Lys
    50

<210> SEQ ID NO 185
<211> LENGTH: 18
<212> TYPE: PRT
<213> ORGANISM: Influenza virus

<400> SEQUENCE: 185
```

```
His Asn Gly Lys Leu Cys Arg Leu Lys Gly Ile Ala Pro Leu Gln Leu
 1               5                  10                  15

Gly Lys

<210> SEQ ID NO 186
<211> LENGTH: 12
<212> TYPE: PRT
<213> ORGANISM: Influenza virus

<400> SEQUENCE: 186

His Lys Cys Asn Asn Glu Cys Met Glu Ser Val Lys
 1               5                  10

<210> SEQ ID NO 187
<211> LENGTH: 14
<212> TYPE: PRT
<213> ORGANISM: Influenza virus

<400> SEQUENCE: 187

Lys Phe Glu Ile Phe Pro Lys Ala Ser Ser Trp Pro Asn His
 1               5                  10

<210> SEQ ID NO 188
<211> LENGTH: 21
<212> TYPE: PRT
<213> ORGANISM: Influenza virus

<400> SEQUENCE: 188

His Asp Ser Asn Val Lys Asn Leu Tyr Glu Lys Val Arg Ser Gln Leu
 1               5                  10                  15

Arg Asn Asn Ala Lys
             20

<210> SEQ ID NO 189
<211> LENGTH: 22
<212> TYPE: PRT
<213> ORGANISM: Influenza virus

<400> SEQUENCE: 189

Lys Val Asn Ser Val Ile Lys Lys Met Asn Thr Gln Phe Ala Ala Val
 1               5                  10                  15

Gly Lys Glu Phe Asn His
             20

<210> SEQ ID NO 190
<211> LENGTH: 8
<212> TYPE: PRT
<213> ORGANISM: Influenza virus

<400> SEQUENCE: 190

Lys His Asn Gly Lys Leu Cys Lys
 1               5

<210> SEQ ID NO 191
<211> LENGTH: 28
<212> TYPE: PRT
<213> ORGANISM: Influenza virus

<400> SEQUENCE: 191

Lys Lys Gly Thr Ser Tyr Pro Lys Leu Ser Lys Ser Tyr Thr His Asn
 1               5                  10                  15

Lys Gly Lys Glu Val Leu Val Leu Trp Gly Val His
```

20                  25

<210> SEQ ID NO 192
<211> LENGTH: 27
<212> TYPE: PRT
<213> ORGANISM: Influenza virus

<400> SEQUENCE: 192

Lys Gly Thr Ser Tyr Pro Lys Leu Ser Lys Ser Tyr Thr His Asn Lys
1               5                   10                  15

Gly Lys Glu Val Leu Val Leu Trp Gly Val His
            20                  25

<210> SEQ ID NO 193
<211> LENGTH: 21
<212> TYPE: PRT
<213> ORGANISM: Influenza virus

<400> SEQUENCE: 193

Lys Leu Ser Lys Ser Tyr Thr His Asn Lys Gly Lys Glu Val Leu Val
1               5                   10                  15

Leu Trp Gly Val His
            20

<210> SEQ ID NO 194
<211> LENGTH: 18
<212> TYPE: PRT
<213> ORGANISM: Influenza virus

<400> SEQUENCE: 194

Lys Ser Tyr Thr His Asn Lys Gly Lys Glu Val Leu Val Leu Trp Gly
1               5                   10                  15

Val His

<210> SEQ ID NO 195
<211> LENGTH: 10
<212> TYPE: PRT
<213> ORGANISM: Influenza virus

<400> SEQUENCE: 195

Lys Gly Val Thr Ala Ser Cys Ser His Lys
1               5                   10

<210> SEQ ID NO 196
<211> LENGTH: 34
<212> TYPE: PRT
<213> ORGANISM: Influenza virus

<400> SEQUENCE: 196

Lys Gly Val Thr Ala Ser Cys Ser His Lys Gly Arg Ser Ser Phe Tyr
1               5                   10                  15

Arg Asn Leu Leu Trp Leu Thr Glu Lys Asn Gly Leu Tyr Pro Asn Leu
            20                  25                  30

Ser Lys

<210> SEQ ID NO 197
<211> LENGTH: 27
<212> TYPE: PRT
<213> ORGANISM: Influenza virus

<400> SEQUENCE: 197

Lys Gly Asn Ser Tyr Pro Lys Leu Ser Lys Ser Tyr Val Asn Asn Lys

```
                1               5                  10                  15

Glu Lys Glu Val Leu Val Leu Trp Gly Ile His
            20                  25

<210> SEQ ID NO 198
<211> LENGTH: 8
<212> TYPE: PRT
<213> ORGANISM: Influenza virus

<400> SEQUENCE: 198

Lys Glu Phe Asn His Leu Glu Lys
1               5

<210> SEQ ID NO 199
<211> LENGTH: 39
<212> TYPE: PRT
<213> ORGANISM: Influenza virus

<400> SEQUENCE: 199

His Pro Pro Thr Ser Thr Asp Gln Gln Ser Leu Tyr Gln Asn Ala Asp
1               5                   10                  15

Ala Tyr Val Phe Val Gly Ser Ser Lys Tyr Asn Lys Lys Phe Lys Pro
            20                  25                  30

Glu Ile Ala Thr Arg Pro Lys
        35

<210> SEQ ID NO 200
<211> LENGTH: 31
<212> TYPE: PRT
<213> ORGANISM: Influenza virus

<400> SEQUENCE: 200

His Pro Pro Thr Ser Thr Asp Gln Gln Ser Leu Tyr Gln Asn Ala Asp
1               5                   10                  15

Ala Tyr Val Phe Val Gly Ser Ser Lys Tyr Asn Lys Lys Phe Lys
            20                  25                  30

<210> SEQ ID NO 201
<211> LENGTH: 31
<212> TYPE: PRT
<213> ORGANISM: Influenza virus

<400> SEQUENCE: 201

His Glu Gly Lys Ser Ser Phe Tyr Arg Asn Leu Leu Trp Leu Thr Glu
1               5                   10                  15

Lys Glu Gly Ser Tyr Pro Lys Leu Lys Asn Ser Tyr Val Asn Lys
            20                  25                  30

<210> SEQ ID NO 202
<211> LENGTH: 23
<212> TYPE: PRT
<213> ORGANISM: Influenza virus

<400> SEQUENCE: 202

His Glu Gly Lys Ser Ser Phe Tyr Arg Asn Leu Leu Trp Leu Thr Glu
1               5                   10                  15

Lys Glu Gly Ser Tyr Pro Lys
            20

<210> SEQ ID NO 203
<211> LENGTH: 26
<212> TYPE: PRT
```

<213> ORGANISM: Influenza virus

<400> SEQUENCE: 203

His Lys Cys Asp Asn Glu Cys Met Glu Ser Val Arg Asn Gly Thr Tyr
1               5                   10                  15

Asp Tyr Pro Lys Tyr Ser Glu Glu Ser Lys
            20                  25

<210> SEQ ID NO 204
<211> LENGTH: 12
<212> TYPE: PRT
<213> ORGANISM: Influenza virus

<400> SEQUENCE: 204

Lys Glu Ser Ser Trp Pro Asn His Thr Val Thr Lys
1               5                   10

<210> SEQ ID NO 205
<211> LENGTH: 35
<212> TYPE: PRT
<213> ORGANISM: Influenza virus

<400> SEQUENCE: 205

Lys Asn Leu Leu Trp Leu Thr Glu Lys Asn Gly Leu Tyr Pro Asn Leu
1               5                   10                  15

Ser Lys Ser Tyr Val Asn Asn Lys Glu Lys Glu Ile Leu Val Leu Trp
            20                  25                  30

Gly Val His
        35

<210> SEQ ID NO 206
<211> LENGTH: 27
<212> TYPE: PRT
<213> ORGANISM: Influenza virus
<220> FEATURE:
<221> NAME/KEY: MOD_RES
<222> LOCATION: (9)
<223> OTHER INFORMATION: lys or met
<220> FEATURE:
<221> NAME/KEY: MOD_RES
<222> LOCATION: (10)
<223> OTHER INFORMATION: asn or not present
<220> FEATURE:
<221> NAME/KEY: MOD_RES
<222> LOCATION: (16)
<223> OTHER INFORMATION: glu or gly
<220> FEATURE:
<221> NAME/KEY: MOD_RES
<222> LOCATION: (17)
<223> OTHER INFORMATION: not present or lys

<400> SEQUENCE: 206

His Asn Gly Lys Ser Ser Phe Tyr Xaa Xaa Leu Leu Trp Leu Thr Xaa
1               5                   10                  15

Xaa Lys Asn Gly Leu Tyr Pro Asn Leu Ser Lys
            20                  25

<210> SEQ ID NO 207
<211> LENGTH: 17
<212> TYPE: PRT
<213> ORGANISM: Influenza virus

<400> SEQUENCE: 207

His Asn Gly Lys Ser Ser Phe Tyr Lys Asn Leu Leu Trp Leu Thr Glu
1               5                   10                  15

Lys

<210> SEQ ID NO 208
<211> LENGTH: 55
<212> TYPE: PRT
<213> ORGANISM: Influenza virus

<400> SEQUENCE: 208

His Thr Val Thr Lys Gly Val Thr Ala Ser Cys Ser His Asn Gly Lys
1               5                   10                  15

Ser Ser Phe Tyr Lys Asn Leu Leu Trp Leu Thr Glu Lys Asn Gly Leu
            20                  25                  30

Tyr Pro Asn Leu Ser Lys Ser Tyr Val Asn Asn Lys Glu Lys Glu Val
        35                  40                  45

Leu Val Leu Trp Gly Val His
    50                  55

<210> SEQ ID NO 209
<211> LENGTH: 38
<212> TYPE: PRT
<213> ORGANISM: Influenza virus
<220> FEATURE:
<221> NAME/KEY: MOD_RES
<222> LOCATION: (5)
<223> OTHER INFORMATION: lys or gly
<220> FEATURE:
<221> NAME/KEY: MOD_RES
<222> LOCATION: (8)
<223> OTHER INFORMATION: thr or ser
<220> FEATURE:
<221> NAME/KEY: MOD_RES
<222> LOCATION: (21)
<223> OTHER INFORMATION: lys or met
<220> FEATURE:
<221> NAME/KEY: MOD_RES
<222> LOCATION: (22)
<223> OTHER INFORMATION: asn or not present
<220> FEATURE:
<221> NAME/KEY: MOD_RES
<222> LOCATION: (28)
<223> OTHER INFORMATION: glu or gly
<220> FEATURE:
<221> NAME/KEY: MOD_RES
<222> LOCATION: (30)
<223> OTHER INFORMATION: asn, lys or not present

<400> SEQUENCE: 209

His Thr Val Thr Xaa Gly Val Xaa Ala Ser Cys Ser His Asn Gly Lys
1               5                   10                  15

Ser Ser Phe Tyr Xaa Xaa Leu Leu Trp Leu Thr Xaa Lys Xaa Gly Leu
            20                  25                  30

Tyr Pro Asn Leu Ser Lys
        35

<210> SEQ ID NO 210
<211> LENGTH: 29
<212> TYPE: PRT
<213> ORGANISM: Influenza virus

<400> SEQUENCE: 210

His Thr Val Thr Lys Gly Val Thr Ala Ser Cys Ser His Asn Gly Lys
1               5                   10                  15

Ser Ser Phe Tyr Lys Asn Leu Leu Trp Leu Thr Glu Lys
            20                  25

<210> SEQ ID NO 211

```
<211> LENGTH: 48
<212> TYPE: PRT
<213> ORGANISM: Influenza virus

<400> SEQUENCE: 211

Lys Tyr Val Arg Ser Thr Lys Leu Arg Met Val Thr Gly Leu Arg Asn
 1               5                  10                  15

Ile Pro Ser Ile Gln Ser Arg Gly Leu Phe Gly Ala Ile Ala Gly Phe
            20                  25                  30

Ile Glu Gly Gly Trp Thr Gly Met Ile Asp Gly Trp Tyr Gly Tyr His
        35                  40                  45

<210> SEQ ID NO 212
<211> LENGTH: 43
<212> TYPE: PRT
<213> ORGANISM: Influenza virus

<400> SEQUENCE: 212

His Gln Asn Glu Gln Gly Ser Gly Tyr Ala Ala Asp Gln Lys Ser Thr
 1               5                  10                  15

Gln Asn Ala Ile Asn Gly Ile Thr Asn Lys Val Asn Ser Ile Ile Glu
            20                  25                  30

Lys Met Asn Thr Gln Phe Thr Ala Val Gly Lys
        35                  40

<210> SEQ ID NO 213
<211> LENGTH: 33
<212> TYPE: PRT
<213> ORGANISM: Influenza virus

<400> SEQUENCE: 213

His Gln Asn Glu Gln Gly Ser Gly Tyr Ala Ala Asp Gln Lys Ser Thr
 1               5                  10                  15

Gln Asn Ala Ile Asn Gly Ile Thr Asn Lys Val Asn Ser Ile Ile Glu
            20                  25                  30

Lys

<210> SEQ ID NO 214
<211> LENGTH: 26
<212> TYPE: PRT
<213> ORGANISM: Influenza virus

<400> SEQUENCE: 214

His Gln Asn Glu Gln Gly Ser Gly Tyr Ala Ala Asp Gln Lys Ser Thr
 1               5                  10                  15

Gln Asn Ala Ile Asn Gly Ile Thr Asn Lys
            20                  25

<210> SEQ ID NO 215
<211> LENGTH: 23
<212> TYPE: PRT
<213> ORGANISM: Influenza virus

<400> SEQUENCE: 215

His Ser Gly Ala Arg Ser Phe Tyr Arg Asn Leu Leu Trp Ile Val Lys
 1               5                  10                  15

Lys Gly Asn Ser Tyr Pro Lys
            20

<210> SEQ ID NO 216
<211> LENGTH: 26
```

-continued

```
<212> TYPE: PRT
<213> ORGANISM: Influenza virus

<400> SEQUENCE: 216

His Ser Gly Ala Arg Ser Phe Tyr Arg Asn Leu Leu Trp Ile Val Lys
 1               5                  10                  15

Lys Gly Asn Ser Tyr Pro Lys Leu Asn Lys
            20                  25

<210> SEQ ID NO 217
<211> LENGTH: 32
<212> TYPE: PRT
<213> ORGANISM: Influenza virus

<400> SEQUENCE: 217

His Ser Gly Ala Arg Ser Phe Tyr Arg Asn Leu Leu Trp Ile Val Lys
 1               5                  10                  15

Lys Gly Asn Ser Tyr Pro Lys Leu Asn Lys Ser Tyr Thr Asn Asp Lys
            20                  25                  30

<210> SEQ ID NO 218
<211> LENGTH: 34
<212> TYPE: PRT
<213> ORGANISM: Influenza virus

<400> SEQUENCE: 218

His Ser Gly Ala Arg Ser Phe Tyr Arg Asn Leu Leu Trp Ile Val Lys
 1               5                  10                  15

Lys Gly Asn Ser Tyr Pro Lys Leu Asn Lys Ser Tyr Thr Asn Asp Lys
            20                  25                  30

Gly Lys

<210> SEQ ID NO 219
<211> LENGTH: 16
<212> TYPE: PRT
<213> ORGANISM: Influenza virus

<400> SEQUENCE: 219

His Thr Val Ser Lys Gly Val Thr Thr Ser Cys Ser His Asn Gly Lys
 1               5                  10                  15

<210> SEQ ID NO 220
<211> LENGTH: 12
<212> TYPE: PRT
<213> ORGANISM: Influenza virus

<400> SEQUENCE: 220

Lys Ala Thr Ser Trp Pro Asn His Glu Thr Thr Lys
 1               5                  10

<210> SEQ ID NO 221
<211> LENGTH: 12
<212> TYPE: PRT
<213> ORGANISM: Influenza virus

<400> SEQUENCE: 221

Lys Gln Val Thr Thr Ser Cys Ser His Asn Gln Lys
 1               5                  10

<210> SEQ ID NO 222
<211> LENGTH: 27
<212> TYPE: PRT
<213> ORGANISM: Influenza virus
```

-continued

```
<400> SEQUENCE: 222

Lys Gly Asn Ser Tyr Pro Lys Leu Asn Lys Ser Tyr Thr Asn Asp Lys
1               5                   10                  15

Gly Lys Glu Val Leu Val Ile Trp Gly Val His
            20                  25

<210> SEQ ID NO 223
<211> LENGTH: 21
<212> TYPE: PRT
<213> ORGANISM: Influenza virus

<400> SEQUENCE: 223

Lys Leu Asn Lys Ser Tyr Thr Asn Asp Lys Gly Lys Glu Val Leu Val
1               5                   10                  15

Ile Trp Gly Val His
            20

<210> SEQ ID NO 224
<211> LENGTH: 18
<212> TYPE: PRT
<213> ORGANISM: Influenza virus

<400> SEQUENCE: 224

Lys Ser Tyr Thr Asn Asp Lys Gly Lys Glu Val Leu Val Ile Trp Gly
1               5                   10                  15

Val His

<210> SEQ ID NO 225
<211> LENGTH: 35
<212> TYPE: PRT
<213> ORGANISM: Influenza virus
<220> FEATURE:
<221> NAME/KEY: MOD_RES
<222> LOCATION: (16)
<223> OTHER INFORMATION: glu or gln
<220> FEATURE:
<221> NAME/KEY: MOD_RES
<222> LOCATION: (29)
<223> OTHER INFORMATION: val or ala

<400> SEQUENCE: 225

His Asn Gln Lys Ser Ser Phe Tyr Arg Asn Leu Leu Trp Leu Thr Xaa
1               5                   10                  15

Lys Asn Gly Leu Tyr Pro Asn Leu Ser Lys Ser Tyr Xaa Ala Asn Asn
            20                  25                  30

Lys Glu Lys
        35

<210> SEQ ID NO 226
<211> LENGTH: 16
<212> TYPE: PRT
<213> ORGANISM: Influenza virus

<400> SEQUENCE: 226

His Pro Ile Thr Ile Gly Glu Cys Pro Lys Tyr Val Arg Ser Ala Lys
1               5                   10                  15

<210> SEQ ID NO 227
<211> LENGTH: 43
<212> TYPE: PRT
<213> ORGANISM: Influenza virus

<400> SEQUENCE: 227
```

His Gln Asn Glu Gln Gly Ser Gly Tyr Ala Ala Asp Gln Lys Ser Thr
1               5                   10                  15

Gln Asn Ala Ile Asn Gly Ile Thr Asn Lys Val Asn Ser Val Ile Glu
            20                  25                  30

Lys Met Asn Thr Gln Phe Thr Ala Val Gly Lys
            35                  40

<210> SEQ ID NO 228
<211> LENGTH: 33
<212> TYPE: PRT
<213> ORGANISM: Influenza virus

<400> SEQUENCE: 228

His Gln Asn Glu Gln Gly Ser Gly Tyr Ala Ala Asp Gln Lys Ser Thr
1               5                   10                  15

Gln Asn Ala Ile Asn Gly Ile Thr Asn Lys Val Asn Ser Val Ile Glu
            20                  25                  30

Lys

<210> SEQ ID NO 229
<211> LENGTH: 34
<212> TYPE: PRT
<213> ORGANISM: Influenza virus

<400> SEQUENCE: 229

His Asn Gly Lys Ser Ser Phe Tyr Arg Asn Leu Leu Trp Leu Thr Glu
1               5                   10                  15

Lys Asn Gly Leu Tyr Pro Asn Leu Ser Lys Ser Tyr Val Asn Asn Lys
            20                  25                  30

Glu Lys

<210> SEQ ID NO 230
<211> LENGTH: 11
<212> TYPE: PRT
<213> ORGANISM: Influenza virus

<400> SEQUENCE: 230

Lys His Phe Glu Lys Val Lys Ile Leu Pro Lys
1               5                   10

<210> SEQ ID NO 231
<211> LENGTH: 14
<212> TYPE: PRT
<213> ORGANISM: Influenza virus

<400> SEQUENCE: 231

Lys His Leu Leu Ser Ser Val Lys His Phe Glu Lys Val Lys
1               5                   10

<210> SEQ ID NO 232
<211> LENGTH: 13
<212> TYPE: PRT
<213> ORGANISM: Influenza virus
<220> FEATURE:
<221> NAME/KEY: MOD_RES
<222> LOCATION: (3)
<223> OTHER INFORMATION: lys, gln or met
<220> FEATURE:
<221> NAME/KEY: MOD_RES
<222> LOCATION: (4)
<223> OTHER INFORMATION: asp or asn

<400> SEQUENCE: 232

His Ala Xaa Xaa Ile Leu Glu Lys Thr His Asn Gly Lys
1               5                   10

<210> SEQ ID NO 233
<211> LENGTH: 16
<212> TYPE: PRT
<213> ORGANISM: Influenza virus
<220> FEATURE:
<221> NAME/KEY: MOD_RES
<222> LOCATION: (3)
<223> OTHER INFORMATION: lys, gln or met
<220> FEATURE:
<221> NAME/KEY: MOD_RES
<222> LOCATION: (4)
<223> OTHER INFORMATION: asp or asn
<220> FEATURE:
<221> NAME/KEY: MOD_RES
<222> LOCATION: (16)
<223> OTHER INFORMATION: lys or arg

<400> SEQUENCE: 233

His Ala Xaa Xaa Ile Leu Glu Lys Thr His Asn Gly Lys Leu Cys Xaa
1               5                   10                  15

<210> SEQ ID NO 234
<211> LENGTH: 19
<212> TYPE: PRT
<213> ORGANISM: Influenza virus

<400> SEQUENCE: 234

His Asn Val His Pro Leu Thr Ile Gly Glu Cys Pro Lys Tyr Val Lys
1               5                   10                  15

Ser Glu Lys

<210> SEQ ID NO 235
<211> LENGTH: 16
<212> TYPE: PRT
<213> ORGANISM: Influenza virus

<400> SEQUENCE: 235

His Pro Leu Thr Ile Gly Glu Cys Pro Lys Tyr Val Lys Ser Glu Lys
1               5                   10                  15

<210> SEQ ID NO 236
<211> LENGTH: 18
<212> TYPE: PRT
<213> ORGANISM: Influenza virus

<400> SEQUENCE: 236

Lys His Leu Leu Ser Ser Val Lys His Phe Glu Lys Val Lys Ile Leu
1               5                   10                  15

Pro Lys

<210> SEQ ID NO 237
<211> LENGTH: 38
<212> TYPE: PRT
<213> ORGANISM: Influenza virus

<400> SEQUENCE: 237

Lys Arg Gln Ser Ser Gly Ile Met Lys Thr Glu Gly Thr Leu Glu Asn
1               5                   10                  15

Cys Glu Thr Lys Cys Gln Thr Pro Leu Gly Ala Ile Asn Thr Thr Leu
            20                  25                  30

Pro Phe His Asn Val His

```
<210> SEQ ID NO 238
<211> LENGTH: 27
<212> TYPE: PRT
<213> ORGANISM: Influenza virus
<220> FEATURE:
<221> NAME/KEY: MOD_RES
<222> LOCATION: (7)
<223> OTHER INFORMATION: val or ile
<220> FEATURE:
<221> NAME/KEY: MOD_RES
<222> LOCATION: (10)
<223> OTHER INFORMATION: gly or arg
<220> FEATURE:
<221> NAME/KEY: MOD_RES
<222> LOCATION: (26)
<223> OTHER INFORMATION: val or ile

<400> SEQUENCE: 238

Lys Gly Ser Asn Tyr Pro Xaa Ala Lys Xaa Ser Tyr Asn Asn Thr Ser
 1               5                  10                  15

Gly Glu Gln Met Leu Ile Ile Trp Gln Xaa His
            20                  25

<210> SEQ ID NO 239
<211> LENGTH: 36
<212> TYPE: PRT
<213> ORGANISM: Influenza virus

<400> SEQUENCE: 239

His Thr Thr Leu Gly Gln Ser Arg Ala Cys Ala Val Ser Gly Asn Pro
 1               5                  10                  15

Ser Phe Phe Arg Asn Met Val Trp Leu Thr Glu Lys Gly Ser Asn Tyr
            20                  25                  30

Pro Val Ala Lys
        35

<210> SEQ ID NO 240
<211> LENGTH: 7
<212> TYPE: PRT
<213> ORGANISM: Influenza virus

<400> SEQUENCE: 240

Lys His Phe Glu Lys Val Lys
 1               5

<210> SEQ ID NO 241
<211> LENGTH: 38
<212> TYPE: PRT
<213> ORGANISM: Influenza virus

<400> SEQUENCE: 241

Lys Ile Ser Lys Arg Gly Ser Ser Gly Ile Met Lys Thr Glu Gly Thr
 1               5                  10                  15

Leu Glu Asn Cys Glu Thr Lys Cys Gln Thr Pro Leu Gly Ala Ile Asn
            20                  25                  30

Thr Thr Leu Pro Phe His
        35

<210> SEQ ID NO 242
<211> LENGTH: 35
<212> TYPE: PRT
<213> ORGANISM: Influenza virus
```

-continued

<400> SEQUENCE: 242

Lys Arg Gly Ser Ser Gly Ile Met Lys Thr Glu Gly Thr Leu Glu Asn
1               5                   10                  15

Cys Glu Thr Lys Cys Gln Thr Pro Leu Gly Ala Ile Asn Thr Thr Leu
            20                  25                  30

Pro Phe His
        35

<210> SEQ ID NO 243
<211> LENGTH: 27
<212> TYPE: PRT
<213> ORGANISM: Influenza virus

<400> SEQUENCE: 243

Lys Thr Glu Gly Thr Leu Glu Asn Cys Glu Thr Lys Cys Gln Thr Pro
1               5                   10                  15

Leu Gly Ala Ile Asn Thr Thr Leu Pro Phe His
            20                  25

<210> SEQ ID NO 244
<211> LENGTH: 38
<212> TYPE: PRT
<213> ORGANISM: Influenza virus

<400> SEQUENCE: 244

Lys Ile Ser Lys Arg Gly Ser Ser Gly Ile Met Lys Thr Glu Gly Thr
1               5                   10                  15

Leu Glu Asn Cys Glu Thr Lys Cys Gln Thr Pro Leu Gly Ala Ile Asn
            20                  25                  30

Thr Thr Leu Pro Phe His
        35

<210> SEQ ID NO 245
<211> LENGTH: 30
<212> TYPE: PRT
<213> ORGANISM: Influenza virus
<220> FEATURE:
<221> NAME/KEY: MOD_RES
<222> LOCATION: (29)
<223> OTHER INFORMATION: val or ile

<400> SEQUENCE: 245

Lys Thr Glu Gly Thr Leu Glu Asn Cys Glu Thr Lys Cys Gln Thr Pro
1               5                   10                  15

Leu Gly Ala Ile Asn Thr Thr Leu Pro Phe His Asn Xaa His
            20                  25                  30

<210> SEQ ID NO 246
<211> LENGTH: 38
<212> TYPE: PRT
<213> ORGANISM: Influenza virus

<400> SEQUENCE: 246

Lys Ile Ser Lys Arg Gly Ser Ser Gly Ile Met Lys Thr Glu Gly Thr
1               5                   10                  15

Leu Glu Asn Cys Glu Thr Lys Cys Gln Thr Pro Leu Gly Ala Ile Asn
            20                  25                  30

Thr Thr Leu Pro Phe His
        35

<210> SEQ ID NO 247

```
<211> LENGTH: 27
<212> TYPE: PRT
<213> ORGANISM: Influenza virus
<220> FEATURE:
<221> NAME/KEY: MOD_RES
<222> LOCATION: (2)
<223> OTHER INFORMATION: glu or gly

<400> SEQUENCE: 247

Lys Xaa Ser Asn Tyr Pro Val Ala Lys Gly Ser Tyr Asn Asn Thr Ser
  1               5                  10                  15

Gly Glu Gln Met Leu Ile Ile Trp Gly Val His
             20                  25

<210> SEQ ID NO 248
<211> LENGTH: 16
<212> TYPE: PRT
<213> ORGANISM: Influenza virus

<400> SEQUENCE: 248

His Pro Leu Thr Ile Gly Glu Cys Pro Lys Tyr Val Lys Ser Glu Lys
  1               5                  10                  15

<210> SEQ ID NO 249
<211> LENGTH: 16
<212> TYPE: PRT
<213> ORGANISM: Influenza virus

<400> SEQUENCE: 249

Lys Cys Gln Thr Pro Leu Gly Ala Ile Lys Thr Thr Leu Pro Phe His
  1               5                  10                  15

<210> SEQ ID NO 250
<211> LENGTH: 58
<212> TYPE: PRT
<213> ORGANISM: Influenza virus
<220> FEATURE:
<221> NAME/KEY: MOD_RES
<222> LOCATION: (21)
<223> OTHER INFORMATION: phe or ile
<220> FEATURE:
<221> NAME/KEY: MOD_RES
<222> LOCATION: (47)
<223> OTHER INFORMATION: asn or ser

<400> SEQUENCE: 250

His His Ser Asn Asp Gln Gly Ser Gly Tyr Ala Ala Asp Lys Glu Ser
  1               5                  10                  15

Thr Gln Lys Ala Xaa Asp Gly Ile Thr Asn Lys Val Asn Ser Val Ile
             20                  25                  30

Glu Lys Met Asn Thr Gln Phe Glu Ala Val Gly Lys Leu Phe Xaa Asn
         35                  40                  45

Leu Glu Lys Leu Glu Asn Leu Asn Lys Lys
     50                  55

<210> SEQ ID NO 251
<211> LENGTH: 57
<212> TYPE: PRT
<213> ORGANISM: Influenza virus
<220> FEATURE:
<221> NAME/KEY: MOD_RES
<222> LOCATION: (20)
<223> OTHER INFORMATION: phe or ile
<220> FEATURE:
<221> NAME/KEY: MOD_RES
<222> LOCATION: (46)
<223> OTHER INFORMATION: asn or ser
```

<400> SEQUENCE: 251

His Ser Asn Asp Gln Gly Ser Gly Tyr Ala Ala Asp Lys Glu Ser Thr
1               5                   10 15

Gln Lys Ala Xaa Asp Gly Ile Thr Asn Lys Val Asn Ser Val Ile Glu
20 25 30

Lys Met Asn Thr Gln Phe Glu Ala Val Gly Lys Leu Phe Xaa Asn Leu
35 40 45

Glu Lys Leu Glu Asn Leu Asn Lys Lys
50 55

<210> SEQ ID NO 252
<211> LENGTH: 26
<212> TYPE: PRT
<213> ORGANISM: Influenza virus
<220> FEATURE:
<221> NAME/KEY: MOD_RES
<222> LOCATION: (20)
<223> OTHER INFORMATION: phe or ile

<400> SEQUENCE: 252

His Ser Asn Asp Gln Gly Ser Gly Tyr Ala Ala Asp Lys Glu Ser Thr
1 5 10 15

Gln Lys Ala Xaa Asp Gly Ile Thr Asn Lys
20 25

<210> SEQ ID NO 253
<211> LENGTH: 21
<212> TYPE: PRT
<213> ORGANISM: Influenza virus

<400> SEQUENCE: 253

His Asp Ser Asn Val Arg Asn Leu Tyr Asp Lys Val Arg Met Gln Leu
1 5 10 15

Arg Asp Asn Ala Lys
20

<210> SEQ ID NO 254
<211> LENGTH: 30
<212> TYPE: PRT
<213> ORGANISM: Influenza virus

<400> SEQUENCE: 254

His Lys Cys Asp Asp Glu Cys Met Asn Ser Val Lys Asn Gly Thr Tyr
1 5 10 15

Asp Tyr Pro Lys Leu Asn Arg Asn Glu Ile Lys Gly Val Lys
20 25 30

<210> SEQ ID NO 255
<211> LENGTH: 27
<212> TYPE: PRT
<213> ORGANISM: Influenza virus

<400> SEQUENCE: 255

His Lys Cys Asp Asp Glu Cys Met Asn Ser Val Lys Asn Gly Thr Tyr
1 5 10 15

Asp Tyr Pro Lys Leu Asn Arg Asn Glu Ile Lys
20 25

<210> SEQ ID NO 256
<211> LENGTH: 20
<212> TYPE: PRT

```
<213> ORGANISM: Influenza virus

<400> SEQUENCE: 256

His Lys Cys Asp Asp Glu Cys Met Asn Ser Val Lys Asn Gly Th

```
<210> SEQ ID NO 262
<211> LENGTH: 16
<212> TYPE: PRT
<213> ORGANISM: Influenza virus

<400> SEQUENCE: 262

His Ala Lys Asp Ile Leu Glu Lys Thr His Asn Gly Lys Leu Cys Lys
1               5                   10                  15

<210> SEQ ID NO 263
<211> LENGTH: 25
<212> TYPE: PRT
<213> ORGANISM: Influenza virus

<400> SEQUENCE: 263

His Asp Val Tyr Arg Asp Glu Ala Leu Asn Asn Arg Phe Gln Ile Lys
1               5                   10                  15

Gly Val Glu Leu Lys Ser Gly Tyr Lys
            20                  25

<210> SEQ ID NO 264
<211> LENGTH: 19
<212> TYPE: PRT
<213> ORGANISM: Influenza virus

<400> SEQUENCE: 264

His Thr Ile Asp Leu Thr Asp Ser Glu Met Asn Lys Leu Phe Glu Arg
1               5                   10                  15

Thr Arg Lys

<210> SEQ ID NO 265
<211> LENGTH: 7
<212> TYPE: PRT
<213> ORGANISM: Influenza virus

<400> SEQUENCE: 265

Lys Phe His Gln Ile Glu Lys
1               5

<210> SEQ ID NO 266
<211> LENGTH: 11
<212> TYPE: PRT
<213> ORGANISM: Influenza virus
<220> FEATURE:
<221> NAME/KEY: MOD_RES
<222> LOCATION: (8)
<223> OTHER INFORMATION: gly or gln

<400> SEQUENCE: 266

Lys Thr Asn Glu Lys Phe His Xaa Ile Glu Lys
1               5                   10

<210> SEQ ID NO 267
<211> LENGTH: 14
<212> TYPE: PRT
<213> ORGANISM: Influenza virus
<220> FEATURE:
<221> NAME/KEY: MOD_RES
<222> LOCATION: (5)
<223> OTHER INFORMATION: val or leu

<400> SEQUENCE: 267

Lys Leu Asn Arg Xaa Ile Glu Lys Thr Asn Glu Lys Phe His
1               5                   10
```

```
<210> SEQ ID NO 268
<211> LENGTH: 25
<212> TYPE: PRT
<213> ORGANISM: Influenza virus

<400> SEQUENCE: 268

His Gln Ile Glu Lys Glu Phe Ser Glu Val Glu Gly Arg Ile Gln Asp
1               5                   10                  15

Leu Glu Lys Tyr Val Glu Asp Thr Lys
            20                  25

<210> SEQ ID NO 269
<211> LENGTH: 8
<212> TYPE: PRT
<213> ORGANISM: Influenza virus

<400> SEQUENCE: 269

Lys Ile Cys Asn Asn Pro His Lys
1               5

<210> SEQ ID NO 270
<211> LENGTH: 14
<212> TYPE: PRT
<213> ORGANISM: Influenza virus

<400> SEQUENCE: 270

Lys Leu Asn Arg Val Ile Lys Lys Thr Asn Glu Lys Phe His
1               5                   10

<210> SEQ ID NO 271
<211> LENGTH: 24
<212> TYPE: PRT
<213> ORGANISM: Influenza virus
<220> FEATURE:
<221> NAME/KEY: MOD_RES
<222> LOCATION: (3)
<223> OTHER INFORMATION: ile or val
<220> FEATURE:
<221> NAME/KEY: MOD_RES
<222> LOCATION: (17)
<223> OTHER INFORMATION: gly or gln
<220> FEATURE:
<221> NAME/KEY: MOD_RES
<222> LOCATION: (20)
<223> OTHER INFORMATION: arg or lys
<220> FEATURE:
<221> NAME/KEY: MOD_RES
<222> LOCATION: (22)
<223> OTHER INFORMATION: gln or gly

<400> SEQUENCE: 271

His Asp Xaa Tyr Arg Asp Glu Ala Leu Asn Asn Arg Phe Gln Ile Lys
1               5                   10                  15

Xaa Val Glu Xaa Ser Xaa Tyr Lys
            20

<210> SEQ ID NO 272
<211> LENGTH: 25
<212> TYPE: PRT
<213> ORGANISM: Influenza virus

<400> SEQUENCE: 272

His Gln Ile Glu Lys Glu Phe Ser Glu Val Glu Gly Arg Ile Gln Asp
1               5                   10                  15

Leu Glu Lys Tyr Val Glu Asp Thr Lys
```

-continued

```
                    20                  25

<210> SEQ ID NO 273
<211> LENGTH: 25
<212> TYPE: PRT
<213> ORGANISM: Influenza virus

<400> SEQUENCE: 273

Lys Tyr Val Glu Asp Thr Lys Ile Asp Leu Trp Ser Tyr Asn Ala Glu
 1               5                  10                  15

Leu Leu Val Ala Leu Glu Asn Gln His
            20                  25

<210> SEQ ID NO 274
<211> LENGTH: 49
<212> TYPE: PRT
<213> ORGANISM: Influenza virus

<400> SEQUENCE: 274

Lys Tyr Val Lys Gln Asn Ser Leu Lys Leu Ala Thr Gly Met Arg Asn
 1               5                  10                  15

Val Pro Glu Lys Gln Thr Arg Gly Leu Phe Gly Ala Ile Ala Gly Phe
            20                  25                  30

Ile Glu Asn Gly Trp Glu Gly Met Ile Asp Gly Trp Tyr Gly Phe Arg
        35                  40                  45

His

<210> SEQ ID NO 275
<211> LENGTH: 39
<212> TYPE: PRT
<213> ORGANISM: Influenza virus

<400> SEQUENCE: 275

Lys Glu Phe Ser Glu Val Glu Gly Arg Ile Gln Asp Leu Glu Lys Tyr
 1               5                  10                  15

Val Glu Asp Thr Lys Ile Asp Leu Trp Ser Tyr Asn Ala Glu Leu Leu
            20                  25                  30

Val Ala Leu Glu Asn Gln His
        35

<210> SEQ ID NO 276
<211> LENGTH: 33
<212> TYPE: PRT
<213> ORGANISM: Influenza virus
<220> FEATURE:
<221> NAME/KEY: MOD_RES
<222> LOCATION: (4)
<223> OTHER INFORMATION: ser or glu
<220> FEATURE:
<221> NAME/KEY: MOD_RES
<222> LOCATION: (5)
<223> OTHER INFORMATION: glu or gln
<220> FEATURE:
<221> NAME/KEY: MOD_RES
<222> LOCATION: (7)
<223> OTHER INFORMATION: thr or ser
<220> FEATURE:
<221> NAME/KEY: MOD_RES
<222> LOCATION: (9)
<223> OTHER INFORMATION: gln or tyr
<220> FEATURE:
<221> NAME/KEY: MOD_RES
<222> LOCATION: (13)
<223> OTHER INFORMATION: leu or gln
<220> FEATURE:
<221> NAME/KEY: MOD_RES
```

```
<222> LOCATION: (18)
<223> OTHER INFORMATION: ala or asn
<220> FEATURE:
<221> NAME/KEY: MOD_RES
<222> LOCATION: (20)
<223> OTHER INFORMATION: ile or leu
<220> FEATURE:
<221> NAME/KEY: MOD_RES
<222> LOCATION: (22)
<223> OTHER INFORMATION: gln or gly
<220> FEATURE:
<221> NAME/KEY: MOD_RES
<222> LOCATION: (24)
<223> OTHER INFORMATION: asn or thr
<220> FEATURE:
<221> NAME/KEY: MOD_RES
<222> LOCATION: (25)
<223> OTHER INFORMATION: gly or asn
<220> FEATURE:
<221> NAME/KEY: MOD_RES
<222> LOCATION: (27)
<223> OTHER INFORMATION: leu or val
<220> FEATURE:
<221> NAME/KEY: MOD_RES
<222> LOCATION: (29)
<223> OTHER INFORMATION: arg or ser
<220> FEATURE:
<221> NAME/KEY: MOD_RES
<222> LOCATION: (32)
<223> OTHER INFORMATION: glu or cys

<400> SEQUENCE: 276

His Gln Asn Xaa Xaa Gly Xaa Gly Xaa Ala Ala Asp Xaa Lys Ser Thr
 1               5                   10                  15

Gln Xaa Ala Xaa Asp Xaa Ile Xaa Xaa Lys Xaa Asn Xaa Val Ile Xaa
            20                  25                  30

Lys

<210> SEQ ID NO 277
<211> LENGTH: 18
<212> TYPE: PRT
<213> ORGANISM: Influenza virus
<220> FEATURE:
<221> NAME/KEY: MOD_RES
<222> LOCATION: (4)
<223> OTHER INFORMATION: gly or gln
<220> FEATURE:
<221> NAME/KEY: MOD_RES
<222> LOCATION: (6)
<223> OTHER INFORMATION: gln or arg
<220> FEATURE:
<221> NAME/KEY: MOD_RES
<222> LOCATION: (14)
<223> OTHER INFORMATION: val or ile
<220> FEATURE:
<221> NAME/KEY: MOD_RES
<222> LOCATION: (17)
<223> OTHER INFORMATION: ser or thr

<400> SEQUENCE: 277

His Cys Asp Xaa Phe Xaa Asn Glu Lys Trp Asp Leu Phe Xaa Glu Arg
 1               5                   10                  15

Xaa Lys

<210> SEQ ID NO 278
<211> LENGTH: 20
<212> TYPE: PRT
<213> ORGANISM: Influenza virus

<400> SEQUENCE: 278

His Thr Ile Asp Leu Thr Asp Ser Glu Met Asn Lys Lys Leu Phe Glu
```

```
                1               5                  10                 15
Arg Thr Arg Lys
                20

<210> SEQ ID NO 279
<211> LENGTH: 28
<212> TYPE: PRT
<213> ORGANISM: Influenza virus

<400> SEQUENCE: 279

Lys Ser Gly Ser Thr Tyr Pro Val Leu Lys Val Thr Met Pro Asn Asn
  1               5                  10                 15

Asp Asn Phe Asp Lys Leu Tyr Ile Trp Gly Val His
                20                  25

<210> SEQ ID NO 280
<211> LENGTH: 34
<212> TYPE: PRT
<213> ORGANISM: Influenza virus

<400> SEQUENCE: 280

Lys Leu Asn Trp Leu Thr Lys Ser Gly Asn Thr Tyr Pro Val Leu Asn
  1               5                  10                 15

Val Thr Met Pro Asn Asn Asp Asn Phe Asp Lys Leu Val Ile Trp Gly
                20                  25                  30

Val His

<210> SEQ ID NO 281
<211> LENGTH: 19
<212> TYPE: PRT
<213> ORGANISM: Influenza virus

<400> SEQUENCE: 281

His Thr Ile Asp Leu Thr Asp Ser Glu Met Asn Lys Leu Phe Glu Lys
  1               5                  10                 15

Thr Arg Lys

<210> SEQ ID NO 282
<211> LENGTH: 18
<212> TYPE: PRT
<213> ORGANISM: Influenza virus

<400> SEQUENCE: 282

Lys Leu Asn Arg Leu Ile Glu Lys Thr Asn Glu Lys Phe His Gln Thr
  1               5                  10                 15

Glu Lys

<210> SEQ ID NO 283
<211> LENGTH: 47
<212> TYPE: PRT
<213> ORGANISM: Influenza virus

<400> SEQUENCE: 283

His Thr Gly Lys Ser Ser Val Met Arg Ser Asp Ala Pro Ile Asp Phe
  1               5                  10                 15

Cys Asn Ser Glu Cys Ile Thr Pro Asn Gln Ser Ile Pro Asn Asp Lys
                20                  25                  30

Pro Phe Gln Asn Val Asn Lys Ile Thr Tyr Gly Ala Cys Pro Lys
                35                  40                  45
```

```
<210> SEQ ID NO 284
<211> LENGTH: 39
<212> TYPE: PRT
<213> ORGANISM: Influenza virus

<400> SEQUENCE: 284

His Thr Gly Lys Ser Ser Val Met Arg Ser Asp Ala Pro Ile Asp Phe
 1               5                  10                  15

Cys Asn Ser Glu Cys Ile Thr Pro Asn Gln Ser Ile Pro Asn Asp Lys
             20                  25                  30

Pro Phe Gln Asn Val Asn Lys
         35

<210> SEQ ID NO 285
<211> LENGTH: 33
<212> TYPE: PRT
<213> ORGANISM: Influenza virus

<400> SEQUENCE: 285

His Pro Ser Thr Asp Ser Asp Gln Thr Ser Leu Tyr Val Arg Ala Ser
 1               5                  10                  15

Gly Arg Val Thr Val Ser Thr Lys Arg Ser Gln Gln Thr Val Ile Pro
             20                  25                  30

Lys

<210> SEQ ID NO 286
<211> LENGTH: 25
<212> TYPE: PRT
<213> ORGANISM: Influenza virus

<400> SEQUENCE: 286

Lys Tyr Val Glu Asp Thr Lys Ile Asp Leu Trp Ser Tyr Asn Ala Glu
 1               5                  10                  15

Leu Leu Val Ala Leu Glu Asn Gln His
             20                  25

<210> SEQ ID NO 287
<211> LENGTH: 26
<212> TYPE: PRT
<213> ORGANISM: Influenza virus

<400> SEQUENCE: 287

Lys Leu Phe Glu Arg Thr Arg Lys Gln Leu Arg Glu Asn Ala Glu Asp
 1               5                  10                  15

Met Gly Asn Gly Cys Phe Lys Ile Tyr His
             20                  25

<210> SEQ ID NO 288
<211> LENGTH: 16
<212> TYPE: PRT
<213> ORGANISM: Influenza virus

<400> SEQUENCE: 288

Lys Arg Arg Ser Ile Lys Ser Phe Phe Ser Arg Leu Asn Trp Leu His
 1               5                  10                  15

<210> SEQ ID NO 289
<211> LENGTH: 16
<212> TYPE: PRT
<213> ORGANISM: Influenza virus
<220> FEATURE:
<221> NAME/KEY: MOD_RES
<222> LOCATION: (12)
```

<223> OTHER INFORMATION: val or arg

<400> SEQUENCE: 289

His Pro Val Thr Ile Gly Glu Cys Pro Lys Tyr Xaa Lys Ser Thr Lys
1               5                   10                  15

<210> SEQ ID NO 290
<211> LENGTH: 30
<212> TYPE: PRT
<213> ORGANISM: Influenza virus

<400> SEQUENCE: 290

Lys Gly Asn Ser Tyr Pro Lys Leu Ser Lys Ser Tyr Ile
1               5                   10                  15

Ile Asn Lys Lys Lys Glu Val Leu Val Ile Trp Gly Ile His
            20                  25                  30

<210> SEQ ID NO 291
<211> LENGTH: 24
<212> TYPE: PRT
<213> ORGANISM: Influenza virus
<220> FEATURE:
<221> NAME/KEY: MOD_RES
<222> LOCATION: (9)
<223> OTHER INFORMATION: val or tyr

<400> SEQUENCE: 291

Lys Leu Ser Lys Leu Ser Lys Ser Xaa Ile Ile Asn Lys Lys Lys Glu
1               5                   10                  15

Val Leu Val Ile Trp Gly Ile His
            20

<210> SEQ ID NO 292
<211> LENGTH: 21
<212> TYPE: PRT
<213> ORGANISM: Influenza virus
<220> FEATURE:
<221> NAME/KEY: MOD_RES
<222> LOCATION: (6)
<223> OTHER INFORMATION: val or tyr

<400> SEQUENCE: 292

Lys Leu Ser Lys Ser Xaa Ile Ile Asn Lys Lys Lys Glu Val Leu Val
1               5                   10                  15

Ile Trp Gly Ile His
            20

<210> SEQ ID NO 293
<211> LENGTH: 46
<212> TYPE: PRT
<213> ORGANISM: Plasmodium falciparum

<400> SEQUENCE: 293

Lys Glu Glu Glu Glu Lys Glu Lys Glu Lys Glu Lys Glu Lys Glu Glu
1               5                   10                  15

Lys Glu Lys Glu Lys Lys Glu Lys Glu Lys Glu Lys Glu Lys Glu Glu
            20                  25                  30

Glu Lys Glu Lys Glu Lys Glu Lys Glu Glu Glu Lys Lys
        35                  40                  45

<210> SEQ ID NO 294
<211> LENGTH: 48
<212> TYPE: PRT
<213> ORGANISM: Plasmodium falciparum -continued

<400> SEQUENCE: 294

Lys Glu Glu Glu Glu Lys Glu Lys Glu Lys Glu Lys Glu Lys Glu Glu
1               5                   10                  15

Lys Glu Lys Glu Glu Lys Glu Lys Glu Lys Glu Lys Glu Lys Glu Glu
            20                  25                  30

Glu Lys Glu Lys Glu Lys Glu Lys Glu Glu Lys Lys Glu Lys
        35                  40                  45

<210> SEQ ID NO 295
<211> LENGTH: 47
<212> TYPE: PRT
<213> ORGANISM: Plasmodium falciparum

<400> SEQUENCE: 295

Lys Glu Glu Glu Glu Lys Glu Lys Glu Lys Glu Lys Glu Lys Glu Glu
1               5                   10                  15

Lys Glu Lys Glu Glu Lys Glu Lys Glu Lys Glu Lys Glu Lys Glu Glu
            20                  25                  30

Glu Lys Glu Lys Glu Glu Lys Glu Lys Glu Glu Glu Lys Lys
        35                  40                  45

<210> SEQ ID NO 296
<211> LENGTH: 10
<212> TYPE: PRT
<213> ORGANISM: Plasmodium falciparum

<400> SEQUENCE: 296

Lys Glu Glu Glu Glu Lys Glu Lys Glu Lys
1               5                   10

<210> SEQ ID NO 297
<211> LENGTH: 19
<212> TYPE: PRT
<213> ORGANISM: Plasmodium falciparum

<400> SEQUENCE: 297

His Lys Lys Leu Ile Lys Ala Leu Lys Lys Asn Ile Glu Ser Ile Gln
1               5                   10                  15

Asn Lys Lys

<210> SEQ ID NO 298
<211> LENGTH: 19
<212> TYPE: PRT
<213> ORGANISM: Plasmodium falciparum

<400> SEQUENCE: 298

His Lys Lys Leu Ile Lys Ala Leu Lys Lys Asn Ile Glu Ser Ile Gln
1               5                   10                  15

Asn Lys Met

<210> SEQ ID NO 299
<211> LENGTH: 10
<212> TYPE: PRT
<213> ORGANISM: Plasmodium falciparum

<400> SEQUENCE: 299

His Lys Lys Leu Ile Lys Ala Leu Lys Lys
1               5                   10

<210> SEQ ID NO 300

```
<211> LENGTH: 9
<212> TYPE: PRT
<213> ORGANISM: Plasmodium falciparum

<400> SEQUENCE: 300

His Lys Lys Leu Ile Lys Ala Leu Lys
1               5

<210> SEQ ID NO 301
<211> LENGTH: 23
<212> TYPE: PRT
<213> ORGANISM: Plasmodium falciparum

<400> SEQUENCE: 301

Lys Ala Thr Tyr Ser Phe Val Asn Thr Lys Lys Ile Ile Ser Leu
1               5                   10                  15

Lys Ser Gln Gly His Lys Lys
            20

<210> SEQ ID NO 302
<211> LENGTH: 22
<212> TYPE: PRT
<213> ORGANISM: Plasmodium falciparum

<400> SEQUENCE: 302

Lys Ala Thr Tyr Ser Phe Val Asn Thr Lys Lys Lys Ile Ile Ser Leu
1               5                   10                  15

Lys Ser Gln Gly His Lys
            20

<210> SEQ ID NO 303
<211> LENGTH: 21
<212> TYPE: PRT
<213> ORGANISM: Plasmodium falciparum

<400> SEQUENCE: 303

Lys Ala Thr Tyr Ser Phe Val Asn Thr Lys Lys Lys Ile Ile Ser Leu
1               5                   10                  15

Lys Ser Gln Gly His
            20

<210> SEQ ID NO 304
<211> LENGTH: 29
<212> TYPE: PRT
<213> ORGANISM: Plasmodium falciparum

<400> SEQUENCE: 304

His Thr Tyr Val Lys Gly Lys Lys Ala Pro Ser Asp Pro Gln Cys Ala
1               5                   10                  15

Asp Ile Lys Glu Glu Cys Lys Glu Leu Leu Lys Glu Lys
            20                  25

<210> SEQ ID NO 305
<211> LENGTH: 11
<212> TYPE: PRT
<213> ORGANISM: Plasmodium falciparum

<400> SEQUENCE: 305

Lys Ile Ile Ser Leu Lys Ser Gln Gly His Lys
1               5                   10

<210> SEQ ID NO 306
<211> LENGTH: 21
```

```
<212> TYPE: PRT
<213> ORGANISM: Plasmodium falciparum

<400> SEQUENCE: 306

Lys Lys Lys Lys Phe Glu Pro Leu Lys Asn Gly Asn Val Ser Glu Thr
1               5                   10                  15

Ile Lys Leu Ile His
            20

<210> SEQ ID NO 307
<211> LENGTH: 20
<212> TYPE: PRT
<213> ORGANISM: Plasmodium falciparum

<400> SEQUENCE: 307

Lys Lys Lys Phe Glu Pro Leu Lys Asn Gly Asn Val Ser Glu Thr Ile
1               5                   10                  15

Lys Leu Ile His
            20

<210> SEQ ID NO 308
<211> LENGTH: 19
<212> TYPE: PRT
<213> ORGANISM: Plasmodium falciparum

<400> SEQUENCE: 308

Lys Lys Phe Glu Pro Leu Lys Asn Gly Asn Val Ser Glu Thr Ile Lys
1               5                   10                  15

Leu Ile His

<210> SEQ ID NO 309
<211> LENGTH: 13
<212> TYPE: PRT
<213> ORGANISM: Plasmodium falciparum

<400> SEQUENCE: 309

Lys Asn Gly Asn Val Ser Glu Thr Ile Lys Leu Ile His
1               5                   10

<210> SEQ ID NO 310
<211> LENGTH: 11
<212> TYPE: PRT
<213> ORGANISM: Plasmodium falciparum

<400> SEQUENCE: 310

Lys Leu Ile His Leu Gly Asn Lys Asp Lys Lys
1               5                   10

<210> SEQ ID NO 311
<211> LENGTH: 36
<212> TYPE: PRT
<213> ORGANISM: Plasmodium falciparum

<400> SEQUENCE: 311

Lys Val Lys Lys Ile Gly Val Thr Leu Lys Lys Phe Glu Pro Leu Lys
1               5                   10                  15

Asn Gly Asn Val Ser Glu Thr Ile Lys Leu Ile His Leu Gly Asn Lys
            20                  25                  30

Asp Lys Lys His
        35

<210> SEQ ID NO 312
```

```
<211> LENGTH: 59
<212> TYPE: PRT
<213> ORGANISM: Plasmodium falciparum

<400> SEQUENCE: 312

His Leu Ile Tyr Lys Asn Lys Ser Tyr Asn Pro Leu Leu Leu Ser Cys
1               5                   10                  15

Val Lys Lys Met Asn Met Leu Lys Glu Asn Val Asp Tyr Ile Gln Asn
            20                  25                  30

Gln Asn Leu Phe Lys Glu Leu Met Asn Gln Lys Ala Thr Tyr Ser Phe
        35                  40                  45

Val Asn Thr Lys Lys Lys Ile Ile Ser Leu Lys
    50                  55

<210> SEQ ID NO 313
<211> LENGTH: 52
<212> TYPE: PRT
<213> ORGANISM: Plasmodium falciparum

<400> SEQUENCE: 313

His Leu Ile Tyr Lys Asn Lys Ser Tyr Asn Pro Leu Leu Leu Ser Cys
1               5                   10                  15

Val Lys Lys Met Asn Met Leu Lys Glu Asn Val Asp Tyr Ile Gln Asn
            20                  25                  30

Gln Asn Leu Phe Lys Glu Leu Met Asn Gln Lys Ala Thr Tyr Ser Phe
        35                  40                  45

Val Asn Thr Lys
    50

<210> SEQ ID NO 314
<211> LENGTH: 43
<212> TYPE: PRT
<213> ORGANISM: Plasmodium falciparum

<400> SEQUENCE: 314

His Leu Ile Tyr Lys Asn Lys Ser Tyr Asn Pro Leu Leu Leu Ser Cys
1               5                   10                  15

Val Lys Lys Met Asn Met Leu Lys Glu Asn Val Asp Tyr Ile Gln Asn
            20                  25                  30

Gln Asn Leu Phe Lys Glu Leu Met Asn Gln Lys
        35                  40

<210> SEQ ID NO 315
<211> LENGTH: 38
<212> TYPE: PRT
<213> ORGANISM: Plasmodium falciparum

<400> SEQUENCE: 315

His Leu Ile Tyr Lys Asn Lys Ser Tyr Asn Pro Leu Leu Leu Ser Cys
1               5                   10                  15

Val Lys Lys Met Asn Met Leu Lys Glu Asn Val Asp Tyr Ile Gln Lys
            20                  25                  30

Asn Gln Asn Leu Phe Lys
        35

<210> SEQ ID NO 316
<211> LENGTH: 24
<212> TYPE: PRT
<213> ORGANISM: Plasmodium falciparum

<400> SEQUENCE: 316
```

-continued

```
His Leu Ile Tyr Lys Asn Lys Ser Tyr Asn Pro Leu Leu Ser Cys
1               5                   10                  15

Val Lys Lys Met Asn Met Leu Lys
            20

<210> SEQ ID NO 317
<211> LENGTH: 47
<212> TYPE: PRT
<213> ORGANISM: Plasmodium falciparum

<400> SEQUENCE: 317

Lys Ser Ala Asn Asn Ser Ala Asn Asn Gly Lys Lys Asn Asn Ala Glu
1               5                   10                  15

Glu Met Lys Asn Leu Val Asn Phe Leu Gln Ser His Lys Lys Leu Ile
            20                  25                  30

Lys Ala Leu Lys Lys Asn Ile Glu Ser Ile Gln Asn Lys Lys His
        35                  40                  45

<210> SEQ ID NO 318
<211> LENGTH: 37
<212> TYPE: PRT
<213> ORGANISM: Plasmodium falciparum

<400> SEQUENCE: 318

Lys Lys Asn Asn Ala Glu Glu Met Lys Asn Leu Val Asn Phe Leu Gln
1               5                   10                  15

Ser His Lys Lys Leu Ile Lys Ala Leu Lys Lys Asn Ile Glu Ser Ile
            20                  25                  30

Gln Asn Lys Lys His
        35

<210> SEQ ID NO 319
<211> LENGTH: 29
<212> TYPE: PRT
<213> ORGANISM: Plasmodium falciparum

<400> SEQUENCE: 319

Lys Asn Leu Val Asn Phe Leu Gln Ser His Lys Lys Leu Ile Lys Ala
1               5                   10                  15

Leu Lys Lys Asn Ile Glu Ser Ile Gln Asn Lys Lys His
            20                  25

<210> SEQ ID NO 320
<211> LENGTH: 19
<212> TYPE: PRT
<213> ORGANISM: Plasmodium falciparum

<400> SEQUENCE: 320

Lys Lys Leu Ile Lys Ala Leu Lys Lys Asn Ile Glu Ser Ile Gln Asn
1               5                   10                  15

Lys Lys His

<210> SEQ ID NO 321
<211> LENGTH: 18
<212> TYPE: PRT
<213> ORGANISM: Plasmodium falciparum

<400> SEQUENCE: 321

Lys Leu Ile Lys Ala Leu Lys Lys Asn Ile Glu Ser Ile Gln Asn Lys
1               5                   10                  15
```

Lys His

<210> SEQ ID NO 322
<211> LENGTH: 12
<212> TYPE: PRT
<213> ORGANISM: Plasmodium falciparum

<400> SEQUENCE: 322

Lys Lys Asn Ile Glu Ser Ile Gln Asn Lys Lys His
1               5                   10

<210> SEQ ID NO 323
<211> LENGTH: 11
<212> TYPE: PRT
<213> ORGANISM: Plasmodium falciparum

<400> SEQUENCE: 323

Lys Asn Ile Glu Ser Ile Gln Asn Lys Lys His
1               5                   10

<210> SEQ ID NO 324
<211> LENGTH: 17
<212> TYPE: PRT
<213> ORGANISM: Plasmodium falciparum

<400> SEQUENCE: 324

Lys Asn Asn Ala Glu Glu Met Lys Asn Leu Val Asn Phe Leu Gln Ser
1               5                   10                  15

His

<210> SEQ ID NO 325
<211> LENGTH: 23
<212> TYPE: PRT
<213> ORGANISM: Plasmodium falciparum

<400> SEQUENCE: 325

Lys Lys Leu Ile Lys Ala Leu Lys Lys Asn Ile Glu Ser Ile Gln Asn
1               5                   10                  15

Lys Lys Gln Gly His Lys Lys
            20

<210> SEQ ID NO 326
<211> LENGTH: 19
<212> TYPE: PRT
<213> ORGANISM: Plasmodium falciparum

<400> SEQUENCE: 326

Lys Lys Asn Asn Ala Glu Glu Met Lys Asn Leu Val Asn Phe Leu Gln
1               5                   10                  15

Ser His Lys

<210> SEQ ID NO 327
<211> LENGTH: 17
<212> TYPE: PRT
<213> ORGANISM: Plasmodium falciparum

<400> SEQUENCE: 327

Lys Asn Asn Ala Glu Glu Met Lys Asn Leu Val Asn Phe Leu Gln Ser
1               5                   10                  15

His

<210> SEQ ID NO 328

-continued

```
<211> LENGTH: 22
<212> TYPE: PRT
<213> ORGANISM: Plasmodium falciparum

<400> SEQUENCE: 328

Lys Leu Ile Lys Ala Leu Lys Lys Asn Ile Glu Ser Ile Gln Asn Lys
1               5                   10                  15

Lys Gln Gly His Lys Lys
            20

<210> SEQ ID NO 329
<211> LENGTH: 28
<212> TYPE: PRT
<213> ORGANISM: Plasmodium falciparum

<400> SEQUENCE: 329

Lys Val Lys Lys Ile Gly Val Thr Leu Lys Lys Phe Glu Pro Leu Lys
1               5                   10                  15

Asn Gly Asn Val Ser Glu Thr Ile Lys Leu Ile His
            20                  25

<210> SEQ ID NO 330
<211> LENGTH: 13
<212> TYPE: PRT
<213> ORGANISM: Plasmodium falciparum

<400> SEQUENCE: 330

Lys Asn Gly Asn Val Ser Glu Thr Ile Lys Leu Ile His
1               5                   10

<210> SEQ ID NO 331
<211> LENGTH: 11
<212> TYPE: PRT
<213> ORGANISM: Plasmodium falciparum

<400> SEQUENCE: 331

Lys Leu Ile His Leu Gly Asn Lys Asp Lys Lys
1               5                   10

<210> SEQ ID NO 332
<211> LENGTH: 28
<212> TYPE: PRT
<213> ORGANISM: Plasmodium falciparum

<400> SEQUENCE: 332

Lys Ser Ala Asn Ser Ala Asn Asn Gly Lys Lys Asn Asn Ala Glu
1               5                   10                  15

Glu Met Lys Asn Leu Val Asn Phe Leu Gln Ser His
            20                  25

<210> SEQ ID NO 333
<211> LENGTH: 18
<212> TYPE: PRT
<213> ORGANISM: Plasmodium falciparum

<400> SEQUENCE: 333

Lys Lys Asn Asn Ala Glu Glu Met Lys Asn Leu Val Asn Phe Leu Gln
1               5                   10                  15

Ser His

<210> SEQ ID NO 334
<211> LENGTH: 19
<212> TYPE: PRT
```

<213> ORGANISM: Plasmodium falciparum

<400> SEQUENCE: 334

Lys Lys Leu Ile Lys Ala Leu Lys Lys Asn Ile Glu Ser Ile Gln Asn
1               5                   10                  15

Lys Lys His

<210> SEQ ID NO 335
<211> LENGTH: 15
<212> TYPE: PRT
<213> ORGANISM: Plasmodium falciparum

<400> SEQUENCE: 335

Lys Ala Leu Lys Lys Asn Ile Glu Ser Ile Gln Asn Lys Lys His
1               5                   10                  15

<210> SEQ ID NO 336
<211> LENGTH: 12
<212> TYPE: PRT
<213> ORGANISM: Plasmodium falciparum

<400> SEQUENCE: 336

Lys Lys Asn Ile Glu Ser Ile Gln Asn Lys Lys His
1               5                   10

<210> SEQ ID NO 337
<211> LENGTH: 27
<212> TYPE: PRT
<213> ORGANISM: Plasmodium falciparum

<400> SEQUENCE: 337

Lys Glu Leu Met Asn Gln Lys Ala Thr Tyr Ser Phe Val Asn Thr Lys
1               5                   10                  15

Lys Lys Ile Ile Ser Leu Lys Ser Gln Gly His
            20                  25

<210> SEQ ID NO 338
<211> LENGTH: 7
<212> TYPE: PRT
<213> ORGANISM: Plasmodium falciparum

<400> SEQUENCE: 338

Lys Ser Gln Gly His Lys Lys
1               5

<210> SEQ ID NO 339
<211> LENGTH: 12
<212> TYPE: PRT
<213> ORGANISM: Plasmodium falciparum

<400> SEQUENCE: 339

Lys Lys Lys Ile Ile Ser Leu Lys Ser Gln Gly His
1               5                   10

<210> SEQ ID NO 340
<211> LENGTH: 11
<212> TYPE: PRT
<213> ORGANISM: Plasmodium falciparum

<400> SEQUENCE: 340

Lys Lys Ile Ile Ser Leu Lys Ser Gln Gly His
1               5                   10

```
<210> SEQ ID NO 341
<211> LENGTH: 12
<212> TYPE: PRT
<213> ORGANISM: Plasmodium falciparum

<400> SEQUENCE: 341

Lys Lys Asn Ile Glu Ser Ile Gln Asn Lys Lys His
1               5                   10

<210> SEQ ID NO 342
<211> LENGTH: 11
<212> TYPE: PRT
<213> ORGANISM: Plasmodium falciparum

<400> SEQUENCE: 342

Lys Asn Ile Glu Ser Ile Gln Asn Lys Lys His
1               5                   10

<210> SEQ ID NO 343
<211> LENGTH: 29
<212> TYPE: PRT
<213> ORGANISM: Plasmodium falciparum

<400> SEQUENCE: 343

His Thr Tyr Val Lys Gly Lys Lys Ala Pro Ser Asp Pro Gln Cys Ala
1               5                   10                  15

Asp Ile Lys Glu Glu Cys Lys Glu Leu Leu Lys Glu Lys
            20                  25

<210> SEQ ID NO 344
<211> LENGTH: 27
<212> TYPE: PRT
<213> ORGANISM: Plasmodium falciparum

<400> SEQUENCE: 344

His Thr Tyr Val Lys Gly Lys Lys Ala Pro Ser Asp Pro Gln Cys Ala
1               5                   10                  15

Asp Ile Lys Glu Glu Cys Lys Glu Leu Leu Lys
            20                  25

<210> SEQ ID NO 345
<211> LENGTH: 29
<212> TYPE: PRT
<213> ORGANISM: Plasmodium falciparum

<400> SEQUENCE: 345

His Glu Asn Val Leu Ser Ala Ala Leu Glu Asn Thr Gln Ser Glu Glu
1               5                   10                  15

Glu Lys Lys Glu Val Ile Asp Val Ile Glu Glu Val Lys
            20                  25

<210> SEQ ID NO 346
<211> LENGTH: 48
<212> TYPE: PRT
<213> ORGANISM: Plasmodium falciparum

<400> SEQUENCE: 346

Lys Glu Asn Val Val Thr Thr Ile Leu Glu Lys Val Glu Glu Thr Thr
1               5                   10                  15

Ala Glu Ser Val Thr Thr Phe Ser Asn Ile Leu Glu Glu Ile Gln Glu
            20                  25                  30

Asn Thr Ile Thr Asn Asp Thr Ile Glu Glu Lys Leu Glu Glu Leu His
        35                  40                  45
```

<210> SEQ ID NO 347
<211> LENGTH: 14
<212> TYPE: PRT
<213> ORGANISM: Plasmodium falciparum

<400> SEQUENCE: 347

His Tyr Leu Gln Gln Met Lys Glu Lys Phe Ser Lys Glu Lys
1               5                   10

<210> SEQ ID NO 348
<211> LENGTH: 42
<212> TYPE: PRT
<213> ORGANISM: Plasmodium falciparum

<400> SEQUENCE: 348

His Tyr Leu Gln Gln Met Lys Glu Lys Phe Ser Lys Glu Lys Asn Asn
1               5                   10                  15

Asn Val Ile Glu Val Thr Asn Lys Ala Glu Lys Lys Gly Asn Val Gln
            20                  25                  30

Val Thr Asn Lys Thr Glu Lys Thr Thr Lys
        35                  40

<210> SEQ ID NO 349
<211> LENGTH: 48
<212> TYPE: PRT
<213> ORGANISM: Plasmodium falciparum

<400> SEQUENCE: 349

His Tyr Leu Gln Gln Met Lys Glu Lys Phe Ser Lys Glu Lys Asn Asn
1               5                   10                  15

Asn Val Ile Glu Val Thr Asn Lys Ala Glu Lys Lys Gly Asn Val Gln
            20                  25                  30

Val Thr Asn Lys Thr Glu Lys Thr Thr Lys Val Asp Lys Asn Asn Lys
        35                  40                  45

<210> SEQ ID NO 350
<211> LENGTH: 57
<212> TYPE: PRT
<213> ORGANISM: Plasmodium falciparum

<400> SEQUENCE: 350

His Tyr Leu Gln Gln Met Lys Glu Lys Phe Ser Lys Glu Lys Asn Asn
1               5                   10                  15

Asn Val Ile Glu Val Thr Asn Lys Ala Glu Lys Lys Gly Asn Val Gln
            20                  25                  30

Val Thr Asn Lys Thr Glu Lys Thr Thr Lys Val Asp Lys Asn Asn Lys
        35                  40                  45

Val Pro Lys Lys Arg Arg Thr Gln Lys
    50                  55

<210> SEQ ID NO 351
<211> LENGTH: 59
<212> TYPE: PRT
<213> ORGANISM: Plasmodium falciparum

<400> SEQUENCE: 351

His Tyr Leu Gln Gln Met Lys Glu Lys Phe Ser Lys Glu Lys Asn Asn
1               5                   10                  15

Asn Val Ile Glu Val Thr Asn Lys Ala Glu Lys Lys Gly Asn Val Gln
            20                  25                  30

Val Thr Asn Lys Thr Glu Lys Thr Thr Lys Val Asp Lys Asn Asn Lys
            35                  40                  45

Val Pro Lys Lys Arg Arg Thr Gln Lys Ser Lys
 50                  55

<210> SEQ ID NO 352
<211> LENGTH: 52
<212> TYPE: PRT
<213> ORGANISM: Plasmodium falciparum

<400> SEQUENCE: 352

His Val Asp Glu Val Met Lys Tyr Val Gln Lys Ile Asp Lys Glu Val
 1               5                  10                  15

Asp Lys Glu Val Ser Lys Ala Leu Glu Ser Lys Asn Asp Val Thr Asn
            20                  25                  30

Val Leu Lys Gln Asn Gln Asp Phe Phe Ser Lys Val Lys Asn Phe Val
            35                  40                  45

Lys Lys Tyr Lys
 50

<210> SEQ ID NO 353
<211> LENGTH: 50
<212> TYPE: PRT
<213> ORGANISM: Plasmodium falciparum

<400> SEQUENCE: 353

His Val Asp Glu Val Met Lys Tyr Val Gln Lys Ile Asp Lys Glu Val
 1               5                  10                  15

Asp Lys Glu Val Ser Lys Ala Leu Glu Ser Lys Asn Asp Val Thr Asn
            20                  25                  30

Val Leu Lys Gln Asn Gln Asp Phe Phe Ser Lys Val Lys Asn Phe Val
            35                  40                  45

Lys Lys
 50

<210> SEQ ID NO 354
<211> LENGTH: 43
<212> TYPE: PRT
<213> ORGANISM: Plasmodium falciparum

<400> SEQUENCE: 354

His Val Asp Glu Val Met Lys Tyr Val Gln Lys Ile Asp Lys Glu Val
 1               5                  10                  15

Asp Lys Glu Val Ser Lys Ala Leu Glu Ser Lys Asn Asp Val Thr Asn
            20                  25                  30

Val Leu Lys Gln Asn Gln Asp Phe Phe Ser Lys
            35                  40

<210> SEQ ID NO 355
<211> LENGTH: 35
<212> TYPE: PRT
<213> ORGANISM: Plasmodium falciparum

<400> SEQUENCE: 355

His Val Asp Glu Val Met Lys Tyr Val Gln Lys Ile Asp Lys Glu Val
 1               5                  10                  15

Asp Lys Glu Val Ser Lys Ala Leu Glu Ser Lys Asn Asp Val Thr Asn
            20                  25                  30

Val Leu Lys

<210> SEQ ID NO 356
<211> LENGTH: 27
<212> TYPE: PRT
<213> ORGANISM: Plasmodium falciparum

<400> SEQUENCE: 356

His Val Asp Glu Val Met Lys Tyr Val Gln Lys Ile Asp Lys Glu Val
1               5                   10                  15

Asp Lys Glu Val Ser Lys Ala Leu Glu Ser Lys
            20                  25

<210> SEQ ID NO 357
<211> LENGTH: 22
<212> TYPE: PRT
<213> ORGANISM: Plasmodium falciparum

<400> SEQUENCE: 357

His Val Asp Glu Val Met Lys Tyr Val Gln Lys Ile Asp Lys Glu Val
1               5                   10                  15

Asp Lys Glu Val Ser Lys
            20

<210> SEQ ID NO 358
<211> LENGTH: 18
<212> TYPE: PRT
<213> ORGANISM: Plasmodium falciparum

<400> SEQUENCE: 358

His Val Asp Glu Val Met Lys Tyr Val Gln Lys Ile Asp Lys Glu Val
1               5                   10                  15

Asp Lys

<210> SEQ ID NO 359
<211> LENGTH: 14
<212> TYPE: PRT
<213> ORGANISM: Plasmodium falciparum

<400> SEQUENCE: 359

His Val Asp Glu Val Met Lys Tyr Val Gln Lys Ile Asp Lys
1               5                   10

<210> SEQ ID NO 360
<211> LENGTH: 39
<212> TYPE: PRT
<213> ORGANISM: Plasmodium falciparum

<400> SEQUENCE: 360

Lys Asp Glu Val Ile Asp Leu Ile Val Gln Lys Glu Lys Arg Ile Glu
1               5                   10                  15

Lys Val Lys Ala Lys Lys Lys Leu Glu Lys Val Glu Glu Gly
            20                  25                  30

Val Ser Gly Leu Lys Lys His
        35

<210> SEQ ID NO 361
<211> LENGTH: 23
<212> TYPE: PRT
<213> ORGANISM: Plasmodium falciparum

<400> SEQUENCE: 361

```
Lys Val Lys Ala Lys Lys Lys Leu Glu Lys Val Glu Glu Gly
 1               5                  10                  15

Val Ser Gly Leu Lys Lys His
            20
```

<210> SEQ ID NO 362
<211> LENGTH: 21
<212> TYPE: PRT
<213> ORGANISM: Plasmodium falciparum

<400> SEQUENCE: 362

```
Lys Ala Lys Lys Lys Leu Glu Lys Val Glu Glu Gly Val Ser
 1               5                  10                  15

Gly Leu Lys Lys His
            20
```

<210> SEQ ID NO 363
<211> LENGTH: 19
<212> TYPE: PRT
<213> ORGANISM: Plasmodium falciparum

<400> SEQUENCE: 363

```
Lys Lys Lys Lys Leu Glu Lys Lys Val Glu Glu Gly Val Ser Gly Leu
 1               5                  10                  15

Lys Lys His
```

<210> SEQ ID NO 364
<211> LENGTH: 18
<212> TYPE: PRT
<213> ORGANISM: Plasmodium falciparum

<400> SEQUENCE: 364

```
Lys Lys Lys Leu Glu Lys Lys Val Glu Glu Gly Val Ser Gly Leu Lys
 1               5                  10                  15

Lys His
```

<210> SEQ ID NO 365
<211> LENGTH: 17
<212> TYPE: PRT
<213> ORGANISM: Plasmodium falciparum

<400> SEQUENCE: 365

```
Lys Lys Leu Glu Lys Lys Val Glu Glu Gly Val Ser Gly Leu Lys Lys
 1               5                  10                  15

His
```

<210> SEQ ID NO 366
<211> LENGTH: 16
<212> TYPE: PRT
<213> ORGANISM: Plasmodium falciparum

<400> SEQUENCE: 366

```
Lys Leu Glu Lys Lys Val Glu Glu Gly Val Ser Gly Leu Lys Lys His
 1               5                  10                  15
```

<210> SEQ ID NO 367
<211> LENGTH: 13
<212> TYPE: PRT
<213> ORGANISM: Plasmodium falciparum

<400> SEQUENCE: 367

```
Lys Lys Val Glu Glu Gly Val Ser Gly Leu Lys Lys His
```

```
1               5                   10
```

<210> SEQ ID NO 368
<211> LENGTH: 12
<212> TYPE: PRT
<213> ORGANISM: Plasmodium falciparum

<400> SEQUENCE: 368

Lys Val Glu Glu Gly Val Ser Gly Leu Lys Lys His
1               5                   10

<210> SEQ ID NO 369
<211> LENGTH: 59
<212> TYPE: PRT
<213> ORGANISM: Plasmodium falciparum

<400> SEQUENCE: 369

His Val Glu Gln Asn Val Tyr Val Asp Val Asp Val Pro Ala Met Lys
1               5                   10                  15

Asp Gln Phe Leu Gly Ile Leu Asn Glu Ala Gly Gly Leu Lys Glu Met
            20                  25                  30

Phe Phe Asn Leu Glu Asp Val Phe Lys Ser Glu Ser Asp Val Ile Thr
        35                  40                  45

Val Glu Glu Ile Lys Asp Glu Pro Val Gln Lys
    50                  55

<210> SEQ ID NO 370
<211> LENGTH: 53
<212> TYPE: PRT
<213> ORGANISM: Plasmodium falciparum

<400> SEQUENCE: 370

His Ile Lys Gly Leu Glu Glu Asp Asp Leu Glu Glu Val Asp Asp Leu
1               5                   10                  15

Lys Gly Ser Ile Leu Asp Met Leu Lys Gly Asp Met Glu Leu Gly Asp
            20                  25                  30

Met Asp Lys Glu Ser Leu Glu Asp Val Thr Thr Lys Leu Gly Glu Arg
        35                  40                  45

Val Glu Ser Leu Lys
    50

<210> SEQ ID NO 371
<211> LENGTH: 44
<212> TYPE: PRT
<213> ORGANISM: Plasmodium falciparum

<400> SEQUENCE: 371

His Ile Lys Gly Leu Glu Glu Asp Asp Leu Glu Glu Val Asp Asp Leu
1               5                   10                  15

Lys Gly Ser Ile Leu Asp Met Leu Lys Gly Asp Met Glu Leu Gly Asp
            20                  25                  30

Met Asp Lys Glu Ser Leu Glu Asp Val Thr Thr Lys
        35                  40

<210> SEQ ID NO 372
<211> LENGTH: 35
<212> TYPE: PRT
<213> ORGANISM: Plasmodium falciparum

<400> SEQUENCE: 372

His Ile Lys Gly Leu Glu Glu Asp Asp Leu Glu Glu Val Asp Asp Leu

```
                1               5                   10                  15
Lys Gly Ser Ile Leu Asp Met Leu Lys Gly Asp Met Glu Leu Gly Asp
            20                  25                  30

Met Asp Lys
        35

<210> SEQ ID NO 373
<211> LENGTH: 25
<212> TYPE: PRT
<213> ORGANISM: Plasmodium falciparum

<400> SEQUENCE: 373

His Ile Lys Gly Leu Glu Glu Asp Asp Leu Glu Glu Val Asp Asp Leu
1               5                   10                  15

Lys Gly Ser Ile Leu Asp Met Leu Lys
            20                  25

<210> SEQ ID NO 374
<211> LENGTH: 31
<212> TYPE: PRT
<213> ORGANISM: Plasmodium falciparum

<400> SEQUENCE: 374

His Ile Ile Ser Gly Asp Ala Asp Val Leu Ser Ser Ala Leu Gly Met
1               5                   10                  15

Asp Glu Glu Gln Met Lys Thr Arg Lys Lys Ala Gln Arg Pro Lys
            20                  25                  30

<210> SEQ ID NO 375
<211> LENGTH: 23
<212> TYPE: PRT
<213> ORGANISM: Plasmodium falciparum

<400> SEQUENCE: 375

His Asp Ile Thr Thr Thr Leu Asp Glu Val Val Glu Leu Lys Asp Val
1               5                   10                  15

Glu Glu Asp Lys Ile Glu Lys
            20

<210> SEQ ID NO 376
<211> LENGTH: 10
<212> TYPE: PRT
<213> ORGANISM: Plasmodium falciparum

<400> SEQUENCE: 376

Lys Lys Leu Glu Glu Val His Glu Leu Lys
1               5                   10

<210> SEQ ID NO 377
<211> LENGTH: 9
<212> TYPE: PRT
<213> ORGANISM: Plasmodium falciparum

<400> SEQUENCE: 377

Lys Leu Glu Glu Val His Glu Leu Lys
1               5

<210> SEQ ID NO 378
<211> LENGTH: 19
<212> TYPE: PRT
<213> ORGANISM: Plasmodium falciparum

<400> SEQUENCE: 378
```

Lys Thr Ile Glu Thr Asp Ile Leu Glu Glu Lys Lys Glu Ile Glu
1               5                   10                  15

Lys Asp His

<210> SEQ ID NO 379
<211> LENGTH: 11
<212> TYPE: PRT
<213> ORGANISM: Plasmodium falciparum

<400> SEQUENCE: 379

Lys Lys Glu Ile Glu Lys Asp His Phe Glu Lys
1               5                   10

<210> SEQ ID NO 380
<211> LENGTH: 6
<212> TYPE: PRT
<213> ORGANISM: Plasmodium falciparum

<400> SEQUENCE: 380

Lys Asp His Phe Glu Lys
1               5

<210> SEQ ID NO 381
<211> LENGTH: 11
<212> TYPE: PRT
<213> ORGANISM: Plasmodium falciparum

<400> SEQUENCE: 381

Lys Phe Glu Glu Glu Ala Glu Glu Ile Lys His
1               5                   10

<210> SEQ ID NO 382
<211> LENGTH: 47
<212> TYPE: PRT
<213> ORGANISM: Plasmodium falciparum

<400> SEQUENCE: 382

Lys Asp Gly Asp Thr Lys Cys Thr Leu Glu Cys Ala Gln Gly Lys Lys
1               5                   10                  15

Cys Ile Lys His Lys Ser Asp His Asn His Lys Ser Asp His Asn His
                20                  25                  30

Lys Ser Asp Pro Asn His Lys Lys Asn Asn Asn Asn Lys
            35                  40                  45

<210> SEQ ID NO 383
<211> LENGTH: 40
<212> TYPE: PRT
<213> ORGANISM: Plasmodium falciparum

<400> SEQUENCE: 383

Lys Asp Gly Asp Thr Lys Cys Thr Leu Glu Cys Ala Gln Gly Lys Lys
1               5                   10                  15

Cys Ile Lys His Lys Ser Asp His Asn His Lys Ser Asp His Asn His
                20                  25                  30

Lys Ser Asp Pro Asn His Lys Lys
            35                  40

<210> SEQ ID NO 384
<211> LENGTH: 39
<212> TYPE: PRT
<213> ORGANISM: Plasmodium falciparum

```
<400> SEQUENCE: 384

Lys Asp Gly Asp Thr Lys Cys Thr Leu Glu Cys Ala Gln Gly Lys Lys
1               5                   10                  15

Cys Ile Lys His Lys Ser Asp His Asn His Lys Ser Asp His Asn His
            20                  25                  30

Lys Ser Asp Pro Asn His Lys
        35

<210> SEQ ID NO 385
<211> LENGTH: 33
<212> TYPE: PRT
<213> ORGANISM: Plasmodium falciparum

<400> SEQUENCE: 385

Lys Asp Gly Asp Thr Lys Cys Thr Leu Glu Cys Ala Gln Gly Lys Lys
1               5                   10                  15

Cys Ile Lys His Lys Ser Asp His Asn His Lys Ser Asp His Asn His
            20                  25                  30

Lys

<210> SEQ ID NO 386
<211> LENGTH: 27
<212> TYPE: PRT
<213> ORGANISM: Plasmodium falciparum

<400> SEQUENCE: 386

Lys Asp Gly Asp Thr Lys Cys Thr Leu Glu Cys Ala Gln Gly Lys Lys
1               5                   10                  15

Cys Ile Lys His Lys Ser Asp His Asn His Lys
            20                  25

<210> SEQ ID NO 387
<211> LENGTH: 21
<212> TYPE: PRT
<213> ORGANISM: Plasmodium falciparum

<400> SEQUENCE: 387

Lys Asp Gly Asp Thr Lys Cys Thr Leu Glu Cys Ala Gln Gly Lys Lys
1               5                   10                  15

Cys Ile Lys His Lys
            20

<210> SEQ ID NO 388
<211> LENGTH: 16
<212> TYPE: PRT
<213> ORGANISM: Plasmodium falciparum

<400> SEQUENCE: 388

Lys Asp Gly Asp Thr Lys Cys Thr Leu Glu Cys Ala Gln Gly Lys Lys
1               5                   10                  15

<210> SEQ ID NO 389
<211> LENGTH: 15
<212> TYPE: PRT
<213> ORGANISM: Plasmodium falciparum

<400> SEQUENCE: 389

Lys Asp Gly Asp Thr Lys Cys Thr Leu Glu Cys Ala Gln Gly Lys
1               5                   10                  15

<210> SEQ ID NO 390
```

```
<211> LENGTH: 23
<212> TYPE: PRT
<213> ORGANISM: Plasmodium falciparum

<400> SEQUENCE: 390

Lys Cys Ile Gln Ala Glu Cys Asn Tyr Lys Glu Cys Gly Glu Gln Lys
 1               5                  10                  15

Cys Val Trp Asp Gly Ile His
            20

<210> SEQ ID NO 391
<211> LENGTH: 14
<212> TYPE: PRT
<213> ORGANISM: Plasmodium falciparum

<400> SEQUENCE: 391

Lys Glu Cys Gly Glu Gln Lys Cys Val Trp Asp Gly Ile His
 1               5                  10

<210> SEQ ID NO 392
<211> LENGTH: 32
<212> TYPE: PRT
<213> ORGANISM: Plasmodium falciparum

<400> SEQUENCE: 392

His Ile Glu Cys Lys Cys Asn Asn Asp Tyr Val Leu Thr Asn Arg Tyr
 1               5                  10                  15

Glu Cys Glu Pro Lys Asn Lys Cys Thr Ser Leu Glu Asp Thr Asn Lys
            20                  25                  30

<210> SEQ ID NO 393
<211> LENGTH: 39
<212> TYPE: PRT
<213> ORGANISM: Plasmodium falciparum

<400> SEQUENCE: 393

Lys Ser Asp His Asn His Lys Ser Asp His Asn His Lys Ser Asp His
 1               5                  10                  15

Asn His Lys Ser Asp His Asn His Lys Ser Asp Pro Asn His Lys Lys
            20                  25                  30

Lys Asn Asn Asn Asn Asn Lys
        35

<210> SEQ ID NO 394
<211> LENGTH: 33
<212> TYPE: PRT
<213> ORGANISM: Plasmodium falciparum

<400> SEQUENCE: 394

Lys Ser Asp His Asn His Lys Ser Asp His Asn His Lys Ser Asp His
 1               5                  10                  15

Asn His Lys Ser Asp Pro Asn His Lys Lys Lys Asn Asn Asn Asn Asn
            20                  25                  30

Lys

<210> SEQ ID NO 395
<211> LENGTH: 27
<212> TYPE: PRT
<213> ORGANISM: Plasmodium falciparum

<400> SEQUENCE: 395

Lys Ser Asp His Asn His Lys Ser Asp His Asn His Lys Ser Asp Pro
 1               5                  10                  15
```

-continued

```
                 1               5                  10                 15
Asn His Lys Lys Lys Asn Asn Asn Asn Lys
                20                  25

<210> SEQ ID NO 396
<211> LENGTH: 21
<212> TYPE: PRT
<213> ORGANISM: Plasmodium falciparum

<400> SEQUENCE: 396

Lys Ser Asp His Asn His Lys Ser Asp Pro Asn His Lys Lys Asn
1               5                  10                 15

Asn Asn Asn Asn Lys
                20

<210> SEQ ID NO 397
<211> LENGTH: 18
<212> TYPE: PRT
<213> ORGANISM: Plasmodium falciparum

<400> SEQUENCE: 397

Lys Lys Lys Asn Asn Asn Asn Lys Asp Asn Lys Ser Asp Pro Asn
1               5                  10                 15

His Lys

<210> SEQ ID NO 398
<211> LENGTH: 17
<212> TYPE: PRT
<213> ORGANISM: Plasmodium falciparum

<400> SEQUENCE: 398

Lys Lys Asn Asn Asn Asn Lys Asp Asn Lys Ser Asp Pro Asn His
1               5                  10                 15

Lys

<210> SEQ ID NO 399
<211> LENGTH: 16
<212> TYPE: PRT
<213> ORGANISM: Plasmodium falciparum

<400> SEQUENCE: 399

Lys Asn Asn Asn Asn Asn Lys Asp Asn Lys Ser Asp Pro Asn His Lys
1               5                  10                 15

<210> SEQ ID NO 400
<211> LENGTH: 10
<212> TYPE: PRT
<213> ORGANISM: Plasmodium falciparum

<400> SEQUENCE: 400

Lys Asp Asn Lys Ser Asp Pro Asn His Lys
1               5                  10

<210> SEQ ID NO 401
<211> LENGTH: 7
<212> TYPE: PRT
<213> ORGANISM: Plasmodium falciparum

<400> SEQUENCE: 401

Lys Ser Asp Pro Asn His Lys
1               5
```

<210> SEQ ID NO 402
<211> LENGTH: 35
<212> TYPE: PRT
<213> ORGANISM: Plasmodium falciparum

<400> SEQUENCE: 402

His Ser Leu Tyr Ala Leu Gln Gln Asn Glu Glu Tyr Gln Lys Val Lys
1               5                   10                  15

Asn Glu Lys Asp Gln Asn Glu Ile Lys Lys Ile Lys Gln Leu Ile Glu
            20                  25                  30

Lys Asn Lys
        35

<210> SEQ ID NO 403
<211> LENGTH: 28
<212> TYPE: PRT
<213> ORGANISM: Plasmodium falciparum

<400> SEQUENCE: 403

His Ser Leu Tyr Ala Leu Gln Gln Asn Glu Glu Tyr Gln Lys Val Lys
1               5                   10                  15

Asn Glu Lys Asp Gln Asn Glu Ile Lys Lys Ile Lys
            20                  25

<210> SEQ ID NO 404
<211> LENGTH: 26
<212> TYPE: PRT
<213> ORGANISM: Plasmodium falciparum

<400> SEQUENCE: 404

His Ser Leu Tyr Ala Leu Gln Gln Asn Glu Glu Tyr Gln Lys Val Lys
1               5                   10                  15

Asn Glu Lys Asp Gln Asn Glu Ile Lys Lys
            20                  25

<210> SEQ ID NO 405
<211> LENGTH: 25
<212> TYPE: PRT
<213> ORGANISM: Plasmodium falciparum

<400> SEQUENCE: 405

His Ser Leu Tyr Ala Leu Gln Gln Asn Glu Glu Tyr Gln Lys Val Lys
1               5                   10                  15

Asn Glu Lys Asp Gln Asn Glu Ile Lys
            20                  25

<210> SEQ ID NO 406
<211> LENGTH: 11
<212> TYPE: PRT
<213> ORGANISM: Plasmodium falciparum

<400> SEQUENCE: 406

His Lys Leu Glu Asn Leu Glu Glu Met Asp Lys
1               5                   10

<210> SEQ ID NO 407
<211> LENGTH: 11
<212> TYPE: PRT
<213> ORGANISM: Plasmodium falciparum

<400> SEQUENCE: 407

Lys His Phe Asp Asp Asn Thr Asn Glu Gln Lys
1               5                   10

```
<210> SEQ ID NO 408
<211> LENGTH: 8
<212> TYPE: PRT
<213> ORGANISM: Plasmodium falciparum

<400> SEQUENCE: 408

Lys Lys Glu Asp Asp Glu Lys His
 1               5

<210> SEQ ID NO 409
<211> LENGTH: 13
<212> TYPE: PRT
<213> ORGANISM: Plasmodium falciparum

<400> SEQUENCE: 409

Lys Glu Glu Asn Asn Lys Lys Glu Asp Asp Glu Lys His
 1               5                  10

<210> SEQ ID NO 410
<211> LENGTH: 21
<212> TYPE: PRT
<213> ORGANISM: Plasmodium falciparum

<400> SEQUENCE: 410

Lys Thr Ser Ser Gly Ile Leu Asn Lys Glu Glu Asn Asn Lys Lys Glu
 1               5                  10                  15

Asp Asp Glu Lys His
            20

<210> SEQ ID NO 411
<211> LENGTH: 7
<212> TYPE: PRT
<213> ORGANISM: Plasmodium falciparum

<400> SEQUENCE: 411

Lys Asn Ile His Ile Lys Lys
 1               5

<210> SEQ ID NO 412
<211> LENGTH: 13
<212> TYPE: PRT
<213> ORGANISM: Plasmodium falciparum

<400> SEQUENCE: 412

His Ile Lys Lys Lys Glu Gly Ile Asp Ile Gly Tyr Lys
 1               5                  10

<210> SEQ ID NO 413
<211> LENGTH: 21
<212> TYPE: PRT
<213> ORGANISM: Plasmodium falciparum

<400> SEQUENCE: 413

Lys Lys Met Trp Thr Cys Lys Leu Trp Asp Asn Lys Gly Asn Glu Ile
 1               5                  10                  15

Thr Lys Asn Ile His
20

<210> SEQ ID NO 414
<211> LENGTH: 30
<212> TYPE: PRT
<213> ORGANISM: Plasmodium falciparum
```

-continued

```
<400> SEQUENCE: 414

Lys Lys Gly Ile Gln Trp Asn Leu Leu Lys Met Trp Thr Cys Lys
1               5                   10                  15

Leu Trp Asp Asn Lys Gly Asn Glu Ile Thr Lys Asn Ile His
            20                  25                  30

<210> SEQ ID NO 415
<211> LENGTH: 50
<212> TYPE: PRT
<213> ORGANISM: Plasmodium falciparum

<400> SEQUENCE: 415

Lys Glu Lys Lys Asp Ser Asn Glu Asn Arg Lys Lys Lys Gln Lys Glu
1               5                   10                  15

Asp Lys Lys Asn Pro Asn Lys Leu Lys Lys Ile Glu Tyr Thr Asn Lys
            20                  25                  30

Ile Thr His Phe Phe Lys Ala Lys Asn Lys Gln Gln Asn Asn Val
        35                  40                  45

Thr His
    50

<210> SEQ ID NO 416
<211> LENGTH: 48
<212> TYPE: PRT
<213> ORGANISM: Plasmodium falciparum

<400> SEQUENCE: 416

Lys Lys Asp Ser Asn Glu Asn Arg Lys Lys Lys Gln Lys Glu Asp Lys
1               5                   10                  15

Lys Asn Pro Asn Lys Leu Lys Lys Ile Glu Tyr Thr Asn Lys Ile Thr
            20                  25                  30

His Phe Phe Lys Ala Lys Asn Asn Lys Gln Gln Asn Asn Val Thr His
        35                  40                  45

<210> SEQ ID NO 417
<211> LENGTH: 47
<212> TYPE: PRT
<213> ORGANISM: Plasmodium falciparum

<400> SEQUENCE: 417

Lys Asp Ser Asn Glu Asn Arg Lys Lys Lys Gln Lys Glu Asp Lys Lys
1               5                   10                  15

Asn Pro Asn Lys Leu Lys Lys Ile Glu Tyr Thr Asn Lys Ile Thr His
            20                  25                  30

Phe Phe Lys Ala Lys Asn Asn Lys Gln Gln Asn Asn Val Thr His
        35                  40                  45

<210> SEQ ID NO 418
<211> LENGTH: 39
<212> TYPE: PRT
<213> ORGANISM: Plasmodium falciparum

<400> SEQUENCE: 418

Lys Lys Gln Lys Glu Asp Lys Lys Asn Pro Asn Lys Leu Lys Lys Ile
1               5                   10                  15

Glu Tyr Thr Asn Lys Ile Thr His Phe Phe Lys Ala Lys Asn Asn Lys
            20                  25                  30

Gln Gln Asn Asn Val Thr His
        35
```

<210> SEQ ID NO 419
<211> LENGTH: 38
<212> TYPE: PRT
<213> ORGANISM: Plasmodium falciparum

<400> SEQUENCE: 419

Lys Gln Lys Glu Asp Lys Lys Asn Pro Asn Lys Leu Lys Lys Ile Glu
1               5                   10                  15

Tyr Thr Asn Lys Ile Thr His Phe Phe Lys Ala Lys Asn Asn Lys Gln
            20                  25                  30

Gln Asn Asn Val Thr His
        35

<210> SEQ ID NO 420
<211> LENGTH: 36
<212> TYPE: PRT
<213> ORGANISM: Plasmodium falciparum

<400> SEQUENCE: 420

Lys Glu Asp Lys Lys Asn Pro Asn Lys Leu Lys Lys Ile Glu Tyr Thr
1               5                   10                  15

Asn Lys Ile Thr His Phe Phe Lys Ala Lys Asn Asn Lys Gln Gln Asn
            20                  25                  30

Asn Val Thr His
        35

<210> SEQ ID NO 421
<211> LENGTH: 32
<212> TYPE: PRT
<213> ORGANISM: Plasmodium falciparum

<400> SEQUENCE: 421

Lys Asn Pro Asn Lys Leu Lys Lys Ile Glu Tyr Thr Asn Lys Ile Thr
1               5                   10                  15

His Phe Phe Lys Ala Lys Asn Asn Lys Gln Gln Asn Asn Val Thr His
            20                  25                  30

<210> SEQ ID NO 422
<211> LENGTH: 26
<212> TYPE: PRT
<213> ORGANISM: Plasmodium falciparum

<400> SEQUENCE: 422

Lys Lys Ile Glu Tyr Thr Asn Lys Ile Thr His Phe Phe Lys Ala Lys
1               5                   10                  15

Asn Asn Lys Gln Gln Asn Asn Val Thr His
            20                  25

<210> SEQ ID NO 423
<211> LENGTH: 25
<212> TYPE: PRT
<213> ORGANISM: Plasmodium falciparum

<400> SEQUENCE: 423

Lys Ile Glu Tyr Thr Asn Lys Ile Thr His Phe Phe Lys Ala Lys Asn
1               5                   10                  15

Asn Lys Gln Gln Asn Asn Val Thr His
            20                  25

<210> SEQ ID NO 424
<211> LENGTH: 19

<212> TYPE: PRT
<213> ORGANISM: Plasmodium falciparum

<400> SEQUENCE: 424

Lys Ile Thr His Phe Phe Lys Ala Lys Asn Asn Lys Gln Gln Asn Asn
1               5                   10                  15

Val Thr His

<210> SEQ ID NO 425
<211> LENGTH: 48
<212> TYPE: PRT
<213> ORGANISM: Plasmodium falciparum

<400> SEQUENCE: 425

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys Asp Ile Lys
            20                  25                  30

Asn Asp Asn Asn Glu Asp Ile Lys Asn Asp Asn Ser Lys Asp Ile Lys
        35                  40                  45

<210> SEQ ID NO 426
<211> LENGTH: 45
<212> TYPE: PRT
<213> ORGANISM: Plasmodium falciparum

<400> SEQUENCE: 426

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys Asp Ile Lys
            20                  25                  30

Asn Asp Asn Asn Glu Asp Ile Lys Asn Asp Asn Ser Lys
        35                  40                  45

<210> SEQ ID NO 427
<211> LENGTH: 40
<212> TYPE: PRT
<213> ORGANISM: Plasmodium falciparum

<400> SEQUENCE: 427

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys Asp Ile Lys
            20                  25                  30

Asn Asp Asn Asn Glu Asp Ile Lys
        35                  40

<210> SEQ ID NO 428
<211> LENGTH: 32
<212> TYPE: PRT
<213> ORGANISM: Plasmodium falciparum

<400> SEQUENCE: 428

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys Asp Ile Lys
            20                  25                  30

<210> SEQ ID NO 429
<211> LENGTH: 29
<212> TYPE: PRT

-continued

<213> ORGANISM: Plasmodium falciparum

<400> SEQUENCE: 429

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys
            20                  25

<210> SEQ ID NO 430
<211> LENGTH: 24
<212> TYPE: PRT
<213> ORGANISM: Plasmodium falciparum

<400> SEQUENCE: 430

His Lys Asn Asn Glu Asp Ile Lys Asn Asp Asn Ser Lys Asp Ile Lys
1               5                   10                  15

Asn Asp Asn Ser Lys Asp Ile Lys
            20

<210> SEQ ID NO 431
<211> LENGTH: 21
<212> TYPE: PRT
<213> ORGANISM: Plasmodium falciparum

<400> SEQUENCE: 431

His Lys Asn Asn Glu Asp Ile Lys Asn Asp Asn Ser Lys Asp Ile Lys
1               5                   10                  15

Asn Asp Asn Ser Lys
            20

<210> SEQ ID NO 432
<211> LENGTH: 16
<212> TYPE: PRT
<213> ORGANISM: Plasmodium falciparum

<400> SEQUENCE: 432

His Lys Asn Asn Glu Asp Ile Lys Asn Asp Asn Ser Lys Asp Ile Lys
1               5                   10                  15

<210> SEQ ID NO 433
<211> LENGTH: 8
<212> TYPE: PRT
<213> ORGANISM: Plasmodium falciparum

<400> SEQUENCE: 433

His Lys Asn Asn Glu Asp Ile Lys
1               5

<210> SEQ ID NO 434
<211> LENGTH: 31
<212> TYPE: PRT
<213> ORGANISM: Plasmodium falciparum

<400> SEQUENCE: 434

Lys Lys Tyr Asp Asp Leu Gln Asn Lys Tyr Asn Ile Leu Asn Lys Leu
1               5                   10                  15

Lys Asn Ser Leu Glu Glu Lys Asn Glu Glu Leu Lys Lys Tyr His
            20                  25                  30

<210> SEQ ID NO 435
<211> LENGTH: 30
<212> TYPE: PRT
<213> ORGANISM: Plasmodium falciparum -continued

```
<400> SEQUENCE: 435

Lys Tyr Asp Asp Leu Gln Asn Lys Tyr Asn Ile Leu Asn Lys Leu Lys
1               5                   10                  15

Asn Ser Leu Glu Glu Lys Asn Glu Glu Leu Lys Lys Tyr His
            20                  25                  30

<210> SEQ ID NO 436
<211> LENGTH: 23
<212> TYPE: PRT
<213> ORGANISM: Plasmodium falciparum

<400> SEQUENCE: 436

Lys Tyr Asn Ile Leu Asn Lys Leu Lys Asn Ser Leu Glu Glu Lys Asn
1               5                   10                  15

Glu Glu Leu Lys Lys Tyr His
            20

<210> SEQ ID NO 437
<211> LENGTH: 17
<212> TYPE: PRT
<213> ORGANISM: Plasmodium falciparum

<400> SEQUENCE: 437

Lys Leu Lys Asn Ser Leu Glu Glu Lys Asn Glu Glu Leu Lys Lys Tyr
1               5                   10                  15

His

<210> SEQ ID NO 438
<211> LENGTH: 15
<212> TYPE: PRT
<213> ORGANISM: Plasmodium falciparum

<400> SEQUENCE: 438

Lys Asn Ser Leu Glu Glu Lys Asn Glu Glu Leu Lys Lys Tyr His
1               5                   10                  15

<210> SEQ ID NO 439
<211> LENGTH: 9
<212> TYPE: PRT
<213> ORGANISM: Plasmodium falciparum

<400> SEQUENCE: 439

Lys Asn Glu Glu Leu Lys Lys Tyr His
1               5

<210> SEQ ID NO 440
<211> LENGTH: 35
<212> TYPE: PRT
<213> ORGANISM: Plasmodium falciparum

<400> SEQUENCE: 440

His Met Gly Asn Asn Gln Asp Ile Asn Glu Asn Val Tyr Asn Ile Lys
1               5                   10                  15

Pro Gln Glu Phe Lys Glu Glu Glu Glu Asp Ile Ser Met Val Asn
            20                  25                  30

Thr Lys Lys
        35

<210> SEQ ID NO 441
<211> LENGTH: 17
<212> TYPE: PRT
```

<213> ORGANISM: Plasmodium falciparum

<400> SEQUENCE: 441

Lys Asn Ser Asn Glu Leu Lys Arg Ile Asn Asp Asn Phe Phe Lys Leu
1               5                   10                  15

His

<210> SEQ ID NO 442
<211> LENGTH: 55
<212> TYPE: PRT
<213> ORGANISM: Plasmodium falciparum

<400> SEQUENCE: 442

Lys Pro Cys Leu Tyr Lys Lys Cys Lys Ile Ser Gln Cys Leu Tyr Lys
1               5                   10                  15

Lys Cys Lys Ile Ser Gln Val Trp Trp Cys Met Pro Val Lys Asp Thr
            20                  25                  30

Phe Asn Thr Tyr Glu Arg Asn Asn Val Leu Asn Ser Lys Ile Glu Asn
        35                  40                  45

Asn Ile Glu Lys Ile Pro His
    50                  55

<210> SEQ ID NO 443
<211> LENGTH: 40
<212> TYPE: PRT
<213> ORGANISM: Plasmodium falciparum

<400> SEQUENCE: 443

His Ile Asn Asn Glu Tyr Thr Asn Lys Asn Pro Lys Asn Cys Leu Leu
1               5                   10                  15

Tyr Lys Asn Glu Glu Arg Asn Tyr Asn Asp Asn Ile Lys Asp Tyr
            20                  25                  30

Ile Asn Ser Met Asn Phe Lys Lys
        35                  40

<210> SEQ ID NO 444
<211> LENGTH: 39
<212> TYPE: PRT
<213> ORGANISM: Plasmodium falciparum

<400> SEQUENCE: 444

His Ile Asn Asn Glu Tyr Thr Asn Lys Asn Pro Lys Asn Cys Leu Leu
1               5                   10                  15

Tyr Lys Asn Glu Glu Arg Asn Tyr Asn Asp Asn Ile Lys Asp Tyr
            20                  25                  30

Ile Asn Ser Met Asn Phe Lys
        35

<210> SEQ ID NO 445
<211> LENGTH: 18
<212> TYPE: PRT
<213> ORGANISM: Plasmodium falciparum

<400> SEQUENCE: 445

His Ile Asn Asn Glu Tyr Thr Asn Lys Asn Pro Lys Asn Cys Leu Leu
1               5                   10                  15

Tyr Lys

<210> SEQ ID NO 446
<211> LENGTH: 23

<212> TYPE: PRT
<213> ORGANISM: Plasmodium falciparum

<400> SEQUENCE: 446

Lys Asn Lys Thr Asn Gln Ser Lys Gly Val Lys Gly Glu Tyr Glu Lys
1               5                   10                  15

Lys Lys Glu Thr Asn Gly His
            20

<210> SEQ ID NO 447
<211> LENGTH: 21
<212> TYPE: PRT
<213> ORGANISM: Plasmodium falciparum

<400> SEQUENCE: 447

Lys Thr Asn Gln Ser Lys Gly Val Lys Gly Glu Tyr Glu Lys Lys Lys
1               5                   10                  15

Glu Thr Asn Gly His
            20

<210> SEQ ID NO 448
<211> LENGTH: 16
<212> TYPE: PRT
<213> ORGANISM: Plasmodium falciparum

<400> SEQUENCE: 448

Lys Gly Val Lys Gly Glu Tyr Glu Lys Lys Lys Glu Thr Asn Gly His
1               5                   10                  15

<210> SEQ ID NO 449
<211> LENGTH: 13
<212> TYPE: PRT
<213> ORGANISM: Plasmodium falciparum

<400> SEQUENCE: 449

Lys Gly Glu Tyr Glu Lys Lys Lys Glu Thr Asn Gly His
1               5                   10

<210> SEQ ID NO 450
<211> LENGTH: 28
<212> TYPE: PRT
<213> ORGANISM: Plasmodium falciparum

<400> SEQUENCE: 450

Lys Ser Gly Met Tyr Thr Asn Glu Gly Asn Lys Ser Cys Glu Cys Ser
1               5                   10                  15

Tyr Lys Lys Lys Ser Ser Ser Ser Asn Lys Val His
            20                  25

<210> SEQ ID NO 451
<211> LENGTH: 18
<212> TYPE: PRT
<213> ORGANISM: Plasmodium falciparum

<400> SEQUENCE: 451

Lys Ser Cys Glu Cys Ser Tyr Lys Lys Lys Ser Ser Ser Ser Asn Lys
1               5                   10                  15

Val His

<210> SEQ ID NO 452
<211> LENGTH: 11
<212> TYPE: PRT
<213> ORGANISM: Plasmodium falciparum

<400> SEQUENCE: 452

Lys Lys Lys Ser Ser Ser Asn Lys Val His
1               5                   10

<210> SEQ ID NO 453
<211> LENGTH: 10
<212> TYPE: PRT
<213> ORGANISM: Plasmodium falciparum

<400> SEQUENCE: 453

Lys Lys Ser Ser Ser Ser Asn Lys Val His
1               5                   10

<210> SEQ ID NO 454
<211> LENGTH: 9
<212> TYPE: PRT
<213> ORGANISM: Plasmodium falciparum

<400> SEQUENCE: 454

Lys Ser Ser Ser Ser Asn Lys Val His
1               5

<210> SEQ ID NO 455
<211> LENGTH: 30
<212> TYPE: PRT
<213> ORGANISM: Plasmodium falciparum

<400> SEQUENCE: 455

His Ile Met Leu Lys Ser Gly Met Tyr Thr Asn Glu Gly Asn Lys Ser
1               5                   10                  15

Cys Glu Cys Ser Tyr Lys Lys Ser Ser Ser Ser Asn Lys
            20                  25                  30

<210> SEQ ID NO 456
<211> LENGTH: 24
<212> TYPE: PRT
<213> ORGANISM: Plasmodium falciparum

<400> SEQUENCE: 456

His Ile Met Leu Lys Ser Gly Met Tyr Thr Asn Glu Gly Asn Lys Ser
1               5                   10                  15

Cys Glu Cys Ser Tyr Lys Lys Lys
            20

<210> SEQ ID NO 457
<211> LENGTH: 23
<212> TYPE: PRT
<213> ORGANISM: Plasmodium falciparum

<400> SEQUENCE: 457

His Ile Met Leu Lys Ser Gly Met Tyr Thr Asn Glu Gly Asn Lys Ser
1               5                   10                  15

Cys Glu Cys Ser Tyr Lys Lys
            20

<210> SEQ ID NO 458
<211> LENGTH: 22
<212> TYPE: PRT
<213> ORGANISM: Plasmodium falciparum

<400> SEQUENCE: 458

His Ile Met Leu Lys Ser Gly Met Tyr Thr Asn Glu Gly Asn Lys Ser

```
                1               5                  10                 15
Cys Glu Cys Ser Tyr Lys
                20

<210> SEQ ID NO 459
<211> LENGTH: 50
<212> TYPE: PRT
<213> ORGANISM: Plasmodium falciparum

<400> SEQUENCE: 459

Lys Pro Leu Ala Lys Leu Arg Lys Arg Glu Lys Thr Gln Ile Asn Lys
1               5                   10                  15

Thr Lys Tyr Glu Arg Gly Asp Val Ile Ile Asp Asn Thr Glu Ile Gln
                20                  25                  30

Lys Ile Ile Ile Arg Asp Tyr His Glu Thr Leu Asn Val His Lys Leu
            35                  40                  45

Asp His
    50

<210> SEQ ID NO 460
<211> LENGTH: 43
<212> TYPE: PRT
<213> ORGANISM: Plasmodium falciparum

<400> SEQUENCE: 460

Lys Arg Glu Lys Thr Gln Ile Asn Lys Thr Lys Tyr Glu Arg Gly Asp
1               5                   10                  15

Val Ile Ile Asp Asn Thr Glu Ile Gln Lys Ile Ile Ile Arg Asp Tyr
                20                  25                  30

His Glu Thr Leu Asn Val His Lys Leu Asp His
            35                  40

<210> SEQ ID NO 461
<211> LENGTH: 40
<212> TYPE: PRT
<213> ORGANISM: Plasmodium falciparum

<400> SEQUENCE: 461

Lys Thr Gln Ile Asn Lys Thr Lys Tyr Glu Arg Gly Asp Val Ile Ile
1               5                   10                  15

Asp Asn Thr Glu Ile Gln Lys Ile Ile Ile Arg Asp Tyr His Glu Thr
                20                  25                  30

Leu Asn Val His Lys Leu Asp His
            35                  40

<210> SEQ ID NO 462
<211> LENGTH: 46
<212> TYPE: PRT
<213> ORGANISM: Plasmodium falciparum

<400> SEQUENCE: 462

Lys Pro Leu Ala Lys Leu Arg Lys Arg Glu Lys Thr Gln Ile Asn Lys
1               5                   10                  15

Thr Lys Tyr Glu Arg Gly Asp Val Ile Ile Asp Asn Thr Glu Ile Gln
                20                  25                  30

Lys Ile Ile Ile Arg Asp Tyr His Glu Thr Leu Asn Val His
            35                  40                  45

<210> SEQ ID NO 463
<211> LENGTH: 40
```

```
<212> TYPE: PRT
<213> ORGANISM: Plasmodium falciparum

<400> SEQUENCE: 463

Lys Pro Leu Ala Lys Leu Arg Lys Arg Glu Lys Thr Gln Ile Asn Lys
 1               5                  10                  15

Thr Lys Tyr Glu Arg Gly Asp Val Ile Ile Asp Asn Thr Glu Ile Gln
            20                  25                  30

Lys Ile Ile Ile Arg Asp Tyr His
        35                  40

<210> SEQ ID NO 464
<211> LENGTH: 36
<212> TYPE: PRT
<213> ORGANISM: Plasmodium falciparum

<400> SEQUENCE: 464

Lys Leu Arg Lys Arg Glu Lys Thr Gln Ile Asn Lys Thr Lys Tyr Glu
 1               5                  10                  15

Arg Gly Asp Val Ile Ile Asp Asn Thr Glu Ile Gln Lys Ile Ile Ile
            20                  25                  30

Arg Asp Tyr His
        35

<210> SEQ ID NO 465
<211> LENGTH: 33
<212> TYPE: PRT
<213> ORGANISM: Plasmodium falciparum

<400> SEQUENCE: 465

Lys Arg Glu Lys Thr Gln Ile Asn Lys Thr Lys Tyr Glu Arg Gly Asp
 1               5                  10                  15

Val Ile Ile Asp Asn Thr Glu Ile Gln Lys Ile Ile Ile Arg Asp Tyr
            20                  25                  30

His

<210> SEQ ID NO 466
<211> LENGTH: 30
<212> TYPE: PRT
<213> ORGANISM: Plasmodium falciparum

<400> SEQUENCE: 466

Lys Thr Gln Ile Asn Lys Thr Lys Tyr Glu Arg Gly Asp Val Ile Ile
 1               5                  10                  15

Asp Asn Thr Glu Ile Gln Lys Ile Ile Ile Arg Asp Tyr His
            20                  25                  30

<210> SEQ ID NO 467
<211> LENGTH: 41
<212> TYPE: PRT
<213> ORGANISM: Plasmodium falciparum

<400> SEQUENCE: 467

Lys Lys Asp Lys Glu Lys Lys Asp Ser Asn Glu Asn Arg Lys Lys
 1               5                  10                  15

Lys Gln Lys Glu Asp Lys Lys Asn Pro Asn Asp Asn Lys Leu Lys Lys
            20                  25                  30

Ile Glu Tyr Thr Asn Lys Ile Thr His
        35                  40
```

<210> SEQ ID NO 468
<211> LENGTH: 40
<212> TYPE: PRT
<213> ORGANISM: Plasmodium falciparum

<400> SEQUENCE: 468

Lys Asp Lys Glu Lys Lys Lys Asp Ser Asn Glu Asn Arg Lys Lys Lys
1               5                   10                  15

Gln Lys Glu Asp Lys Lys Asn Pro Asn Asp Asn Lys Leu Lys Lys Ile
            20                  25                  30

Glu Tyr Thr Asn Lys Ile Thr His
        35                  40

<210> SEQ ID NO 469
<211> LENGTH: 38
<212> TYPE: PRT
<213> ORGANISM: Plasmodium falciparum

<400> SEQUENCE: 469

Lys Glu Lys Lys Lys Asp Ser Asn Glu Asn Arg Lys Lys Lys Gln Lys
1               5                   10                  15

Glu Asp Lys Lys Asn Pro Asn Asp Asn Lys Leu Lys Lys Ile Glu Tyr
            20                  25                  30

Thr Asn Lys Ile Thr His
            35

<210> SEQ ID NO 470
<211> LENGTH: 36
<212> TYPE: PRT
<213> ORGANISM: Plasmodium falciparum

<400> SEQUENCE: 470

Lys Lys Lys Asp Ser Asn Glu Asn Arg Lys Lys Lys Gln Lys Glu Asp
1               5                   10                  15

Lys Lys Asn Pro Asn Asp Asn Lys Leu Lys Lys Ile Glu Tyr Thr Asn
            20                  25                  30

Lys Ile Thr His
        35

<210> SEQ ID NO 471
<211> LENGTH: 35
<212> TYPE: PRT
<213> ORGANISM: Plasmodium falciparum

<400> SEQUENCE: 471

Lys Lys Asp Ser Asn Glu Asn Arg Lys Lys Lys Gln Lys Glu Asp Lys
1               5                   10                  15

Lys Asn Pro Asn Asp Asn Lys Leu Lys Lys Ile Glu Tyr Thr Asn Lys
            20                  25                  30

Ile Thr His
        35

<210> SEQ ID NO 472
<211> LENGTH: 34
<212> TYPE: PRT
<213> ORGANISM: Plasmodium falciparum

<400> SEQUENCE: 472

Lys Asp Ser Asn Glu Asn Arg Lys Lys Lys Gln Lys Glu Asp Lys Lys
1               5                   10                  15

Asn Pro Asn Asp Asn Lys Leu Lys Lys Ile Glu Tyr Thr Asn Lys Ile

Thr His

<210> SEQ ID NO 473
<211> LENGTH: 27
<212> TYPE: PRT
<213> ORGANISM: Plasmodium falciparum

<400> SEQUENCE: 473

Lys Lys Lys Gln Lys Glu Asp Lys Lys Asn Pro Asn Asp Asn Lys Leu
1               5                   10                  15

Lys Lys Ile Glu Tyr Thr Asn Lys Ile Thr His
            20                  25

<210> SEQ ID NO 474
<211> LENGTH: 26
<212> TYPE: PRT
<213> ORGANISM: Plasmodium falciparum

<400> SEQUENCE: 474

Lys Lys Gln Lys Glu Asp Lys Lys Asn Pro Asn Asp Asn Lys Leu Lys
1               5                   10                  15

Lys Ile Glu Tyr Thr Asn Lys Ile Thr His
            20                  25

<210> SEQ ID NO 475
<211> LENGTH: 25
<212> TYPE: PRT
<213> ORGANISM: Plasmodium falciparum

<400> SEQUENCE: 475

Lys Gln Lys Glu Asp Lys Lys Asn Pro Asn Asp Asn Lys Leu Lys Lys
1               5                   10                  15

Ile Glu Tyr Thr Asn Lys Ile Thr His
            20                  25

<210> SEQ ID NO 476
<211> LENGTH: 23
<212> TYPE: PRT
<213> ORGANISM: Plasmodium falciparum

<400> SEQUENCE: 476

Lys Glu Asp Lys Lys Asn Pro Asn Asp Asn Lys Leu Lys Lys Ile Glu
1               5                   10                  15

Tyr Thr Asn Lys Ile Thr His
            20

<210> SEQ ID NO 477
<211> LENGTH: 20
<212> TYPE: PRT
<213> ORGANISM: Plasmodium falciparum

<400> SEQUENCE: 477

Lys Lys Asn Pro Asn Asp Asn Lys Leu Lys Lys Ile Glu Tyr Thr Asn
1               5                   10                  15

Lys Ile Thr His
            20

<210> SEQ ID NO 478
<211> LENGTH: 19
<212> TYPE: PRT
<213> ORGANISM: Plasmodium falciparum -continued

```
<400> SEQUENCE: 478

Lys Asn Pro Asn Asp Asn Lys Leu Lys Lys Ile Glu Tyr Thr Asn Lys
1               5                   10                  15

Ile Thr His

<210> SEQ ID NO 479
<211> LENGTH: 13
<212> TYPE: PRT
<213> ORGANISM: Plasmodium falciparum

<400> SEQUENCE: 479

Lys Leu Lys Lys Ile Glu Tyr Thr Asn Lys Ile Thr His
1               5                   10

<210> SEQ ID NO 480
<211> LENGTH: 11
<212> TYPE: PRT
<213> ORGANISM: Plasmodium falciparum

<400> SEQUENCE: 480

Lys Lys Ile Glu Tyr Thr Asn Lys Ile Thr His
1               5                   10

<210> SEQ ID NO 481
<211> LENGTH: 10
<212> TYPE: PRT
<213> ORGANISM: Plasmodium falciparum

<400> SEQUENCE: 481

Lys Ile Glu Tyr Thr Asn Lys Ile Thr His
1               5                   10

<210> SEQ ID NO 482
<211> LENGTH: 44
<212> TYPE: PRT
<213> ORGANISM: Plasmodium falciparum

<400> SEQUENCE: 482

His Gly Gln Ile Lys Ile Glu Asp Val Asn Asn Glu Asn Phe Asn Asn
1               5                   10                  15

Glu Gln Met Lys Asn Lys Tyr Asn Asp Glu Glu Lys Met Asp Ile Ser
            20                  25                  30

Lys Ser Lys Ser Leu Lys Ser Asp Phe Leu Glu Lys
        35                  40

<210> SEQ ID NO 483
<211> LENGTH: 38
<212> TYPE: PRT
<213> ORGANISM: Plasmodium falciparum

<400> SEQUENCE: 483

His Gly Gln Ile Lys Ile Glu Asp Val Asn Asn Glu Asn Phe Asn Asn
1               5                   10                  15

Glu Gln Met Lys Asn Lys Tyr Asn Asp Glu Glu Lys Met Asp Ile Ser
            20                  25                  30

Lys Ser Lys Ser Leu Lys
        35

<210> SEQ ID NO 484
<211> LENGTH: 35
<212> TYPE: PRT
```

<213> ORGANISM: Plasmodium falciparum

<400> SEQUENCE: 484

His Gly Gln Ile Lys Ile Glu Asp Val Asn Asn Glu Asn Phe Asn Asn
1               5                   10                  15

Glu Gln Met Lys Asn Lys Tyr Asn Asp Glu Glu Lys Met Asp Ile Ser
            20                  25                  30

Lys Ser Lys
        35

<210> SEQ ID NO 485
<211> LENGTH: 33
<212> TYPE: PRT
<213> ORGANISM: Plasmodium falciparum

<400> SEQUENCE: 485

His Gly Gln Ile Lys Ile Glu Asp Val Asn Asn Glu Asn Phe Asn Asn
1               5                   10                  15

Glu Gln Met Lys Asn Lys Tyr Asn Asp Glu Glu Lys Met Asp Ile Ser
            20                  25                  30

Lys

<210> SEQ ID NO 486
<211> LENGTH: 31
<212> TYPE: PRT
<213> ORGANISM: Plasmodium falciparum

<400> SEQUENCE: 486

Lys Lys Tyr Asp Asp Leu Gln Asn Lys Tyr Asn Ile Leu Asn Lys Leu
1               5                   10                  15

Lys Asn Ser Leu Glu Glu Lys Asn Glu Glu Leu Lys Lys Tyr His
            20                  25                  30

<210> SEQ ID NO 487
<211> LENGTH: 30
<212> TYPE: PRT
<213> ORGANISM: Plasmodium falciparum

<400> SEQUENCE: 487

Lys Tyr Asp Asp Leu Gln Asn Lys Tyr Asn Ile Leu Asn Lys Leu Lys
1               5                   10                  15

Asn Ser Leu Glu Glu Lys Asn Glu Glu Leu Lys Lys Tyr His
            20                  25                  30

<210> SEQ ID NO 488
<211> LENGTH: 23
<212> TYPE: PRT
<213> ORGANISM: Plasmodium falciparum

<400> SEQUENCE: 488

Lys Tyr Asn Ile Leu Asn Lys Leu Lys Asn Ser Leu Glu Glu Lys Asn
1               5                   10                  15

Glu Glu Leu Lys Lys Tyr His
            20

<210> SEQ ID NO 489
<211> LENGTH: 17
<212> TYPE: PRT
<213> ORGANISM: Plasmodium falciparum

<400> SEQUENCE: 489

```
Lys Leu Lys Asn Ser Leu Glu Glu Lys Asn Glu Glu Leu Lys Lys Tyr
1               5                   10                  15

His
```

<210> SEQ ID NO 490
<211> LENGTH: 15
<212> TYPE: PRT
<213> ORGANISM: Plasmodium falciparum

<400> SEQUENCE: 490

```
Lys Asn Ser Leu Glu Glu Lys Asn Glu Glu Leu Lys Lys Tyr His
1               5                   10                  15
```

<210> SEQ ID NO 491
<211> LENGTH: 9
<212> TYPE: PRT
<213> ORGANISM: Plasmodium falciparum

<400> SEQUENCE: 491

```
Lys Asn Glu Glu Leu Lys Lys Tyr His
1               5
```

<210> SEQ ID NO 492
<211> LENGTH: 44
<212> TYPE: PRT
<213> ORGANISM: Plasmodium falciparum

<400> SEQUENCE: 492

```
His Met Gly Asn Asn Gln Asp Ile Asn Glu Asn Val Tyr Asn Ile Lys
1               5                   10                  15

Pro Gln Glu Phe Lys Glu Glu Glu Glu Asp Ile Ser Met Val Asn
            20                  25                  30

Thr Lys Lys Cys Asp Asp Ile Gln Glu Asn Ile Lys
        35                  40
```

<210> SEQ ID NO 493
<211> LENGTH: 50
<212> TYPE: PRT
<213> ORGANISM: Plasmodium falciparum

<400> SEQUENCE: 493

```
Lys Thr Asn Leu Tyr Asn Ile Tyr Asn Asn Lys Asn Asp Asp Lys Asp
1               5                   10                  15

Asn Ile Leu Asp Asn Glu Asn Arg Glu Gly Leu Tyr Leu Cys Asp Val
            20                  25                  30

Met Lys Asn Ser Asn Glu Leu Lys Arg Ile Asn Asp Asn Phe Phe Lys
        35                  40                  45

Leu His
    50
```

<210> SEQ ID NO 494
<211> LENGTH: 17
<212> TYPE: PRT
<213> ORGANISM: Plasmodium falciparum

<400> SEQUENCE: 494

```
Lys Asn Ser Asn Glu Leu Lys Arg Ile Asn Asp Asn Phe Phe Lys Leu
1               5                   10                  15

His
```

<210> SEQ ID NO 495

```
<211> LENGTH: 11
<212> TYPE: PRT
<213> ORGANISM: Plasmodium falciparum

<400> SEQUENCE: 495

Lys Arg Ile Asn Asp Asn Phe Phe Lys Leu His
 1               5                  10

<210> SEQ ID NO 496
<211> LENGTH: 40
<212> TYPE: PRT
<213> ORGANISM: Plasmodium falciparum

<400> SEQUENCE: 496

His Ile Asn Asn Glu Tyr Thr Asn Lys Asn Pro Lys Asn Cys Leu Leu
 1               5                  10                  15

Tyr Lys Asn Glu Glu Arg Asn Tyr Asn Asp Asn Asn Ile Lys Asp Tyr
            20                  25                  30

Ile Asn Ser Met Asn Phe Lys Lys
        35                  40

<210> SEQ ID NO 497
<211> LENGTH: 39
<212> TYPE: PRT
<213> ORGANISM: Plasmodium falciparum

<400> SEQUENCE: 497

His Ile Asn Asn Glu Tyr Thr Asn Lys Asn Pro Lys Asn Cys Leu Leu
 1               5                  10                  15

Tyr Lys Asn Glu Glu Arg Asn Tyr Asn Asp Asn Asn Ile Lys Asp Tyr
            20                  25                  30

Ile Asn Ser Met Asn Phe Lys
        35

<210> SEQ ID NO 498
<211> LENGTH: 18
<212> TYPE: PRT
<213> ORGANISM: Plasmodium falciparum

<400> SEQUENCE: 498

His Ile Asn Asn Glu Tyr Thr Asn Lys Asn Pro Lys Asn Cys Leu Leu
 1               5                  10                  15

Tyr Lys

<210> SEQ ID NO 499
<211> LENGTH: 45
<212> TYPE: PRT
<213> ORGANISM: Plasmodium falciparum

<400> SEQUENCE: 499

Lys Pro Cys Leu Tyr Lys Lys Cys Lys Ile Ser Gln Val Trp Trp Cys
 1               5                  10                  15

Met Pro Val Lys Asp Thr Phe Asn Thr Tyr Glu Arg Asn Asn Val Leu
            20                  25                  30

Asn Ser Lys Ile Glu Asn Asn Ile Glu Lys Ile Pro His
        35                  40                  45

<210> SEQ ID NO 500
<211> LENGTH: 39
<212> TYPE: PRT
<213> ORGANISM: Plasmodium falciparum
```

```
<400> SEQUENCE: 500

Lys Cys Lys Ile Ser Gln Val Trp Trp Cys Met Pro Val Lys Asp Thr
1               5                   10                  15

Phe Asn Thr Tyr Glu Arg Asn Asn Val Leu Asn Ser Lys Ile Glu Asn
            20                  25                  30

Asn Ile Glu Lys Ile Pro His
        35

<210> SEQ ID NO 501
<211> LENGTH: 11
<212> TYPE: PRT
<213> ORGANISM: Plasmodium falciparum

<400> SEQUENCE: 501

Lys Ile Glu Asn Asn Ile Glu Lys Ile Pro His
1               5                   10

<210> SEQ ID NO 502
<211> LENGTH: 23
<212> TYPE: PRT
<213> ORGANISM: Plasmodium falciparum

<400> SEQUENCE: 502

Lys Asn Lys Thr Asn Gly Ser Lys Gly Val Lys Gly Glu Tyr Glu Lys
1               5                   10                  15

Lys Lys Glu Thr Asn Gly His
            20

<210> SEQ ID NO 503
<211> LENGTH: 21
<212> TYPE: PRT
<213> ORGANISM: Plasmodium falciparum

<400> SEQUENCE: 503

Lys Thr Asn Gly Ser Lys Gly Val Lys Gly Glu Tyr Glu Lys Lys Lys
1               5                   10                  15

Glu Thr Asn Gly His
            20

<210> SEQ ID NO 504
<211> LENGTH: 16
<212> TYPE: PRT
<213> ORGANISM: Plasmodium falciparum

<400> SEQUENCE: 504

Lys Gly Val Lys Gly Glu Tyr Glu Lys Lys Lys Glu Thr Asn Gly His
1               5                   10                  15

<210> SEQ ID NO 505
<211> LENGTH: 13
<212> TYPE: PRT
<213> ORGANISM: Plasmodium falciparum

<400> SEQUENCE: 505

Lys Gly Glu Tyr Glu Lys Lys Lys Glu Thr Asn Gly His
1               5                   10

<210> SEQ ID NO 506
<211> LENGTH: 60
<212> TYPE: PRT
<213> ORGANISM: Plasmodium falciparum

<400> SEQUENCE: 506
```

-continued

Lys Thr Ile Glu Lys Ile Asn Lys Ser Lys Ser Trp Phe Phe Glu Glu
1               5                   10                  15

Leu Asp Glu Ile Asp Lys Pro Leu Ala Lys Leu Arg Lys Arg Glu Lys
            20                  25                  30

Thr Gln Ile Asn Lys Thr Lys Tyr Glu Arg Gly Asp Val Ile Ile Asp
        35                  40                  45

Asn Thr Glu Ile Gln Lys Ile Ile Arg Asp Tyr His
    50                  55                  60

<210> SEQ ID NO 507
<211> LENGTH: 56
<212> TYPE: PRT
<213> ORGANISM: Plasmodium falciparum

<400> SEQUENCE: 507

Lys Ile Asn Lys Ser Lys Ser Trp Phe Phe Glu Glu Leu Asp Glu Ile
1               5                   10                  15

Asp Lys Pro Leu Ala Lys Leu Arg Lys Arg Glu Lys Thr Gln Ile Asn
            20                  25                  30

Lys Thr Lys Tyr Glu Arg Gly Asp Val Ile Ile Asp Asn Thr Glu Ile
        35                  40                  45

Gln Lys Ile Ile Arg Asp Tyr His
    50                  55

<210> SEQ ID NO 508
<211> LENGTH: 39
<212> TYPE: PRT
<213> ORGANISM: Plasmodium falciparum

<400> SEQUENCE: 508

Lys Pro Leu Ala Lys Leu Arg Lys Arg Glu Lys Thr Gln Ile Asn Lys
1               5                   10                  15

Thr Lys Tyr Glu Arg Gly Asp Val Ile Ile Asp Asn Thr Glu Ile Gln
            20                  25                  30

Lys Ile Ile Arg Asp Tyr His
        35

<210> SEQ ID NO 509
<211> LENGTH: 32
<212> TYPE: PRT
<213> ORGANISM: Plasmodium falciparum

<400> SEQUENCE: 509

His Ile Met Leu Lys Ser Gln Met Tyr Thr Asn Glu Gly Asn Lys Ser
1               5                   10                  15

Cys Glu Cys Ser Tyr Lys Lys Lys Ser Ser Ser Ser Asn Lys Val His
            20                  25                  30

<210> SEQ ID NO 510
<211> LENGTH: 35
<212> TYPE: PRT
<213> ORGANISM: Plasmodium falciparum

<400> SEQUENCE: 510

Lys Leu Arg Lys Arg Glu Lys Thr Gln Ile Asn Lys Thr Lys Tyr Glu
1               5                   10                  15

Arg Gly Asp Val Ile Ile Asp Asn Thr Glu Ile Gln Lys Ile Ile Arg
            20                  25                  30

Asp Tyr His

```
<210> SEQ ID NO 511
<211> LENGTH: 32
<212> TYPE: PRT
<213> ORGANISM: Plasmodium falciparum

<400> SEQUENCE: 511

Lys Arg Glu Lys Thr Gln Ile Asn Lys Thr Lys Tyr Glu Arg Gly Asp
 1               5                  10                  15

Val Ile Ile Asp Asn Thr Glu Ile Gln Lys Ile Ile Arg Asp Tyr His
             20                  25                  30

<210> SEQ ID NO 512
<211> LENGTH: 29
<212> TYPE: PRT
<213> ORGANISM: Plasmodium falciparum

<400> SEQUENCE: 512

Lys Thr Gln Ile Asn Lys Thr Lys Tyr Glu Arg Gly Asp Val Ile Ile
 1               5                  10                  15

Asp Asn Thr Glu Ile Gln Lys Ile Ile Arg Asp Tyr His
             20                  25

<210> SEQ ID NO 513
<211> LENGTH: 48
<212> TYPE: PRT
<213> ORGANISM: Plasmodium falciparum

<400> SEQUENCE: 513

Lys Pro Leu Ala Lys Leu Arg Lys Arg Glu Lys Thr Gln Ile Asn Lys
 1               5                  10                  15

Thr Lys Tyr Glu Arg Gly Asp Val Ile Ile Asp Asn Thr Glu Ile Gln
             20                  25                  30

Lys Ile Ile Arg Asp Tyr His Thr Leu Asn Val His Lys Leu Asp His
         35                  40                  45

<210> SEQ ID NO 514
<211> LENGTH: 44
<212> TYPE: PRT
<213> ORGANISM: Plasmodium falciparum

<400> SEQUENCE: 514

Lys Leu Arg Lys Arg Glu Lys Thr Gln Ile Asn Lys Thr Lys Tyr Glu
 1               5                  10                  15

Arg Gly Asp Val Ile Ile Asp Asn Thr Glu Ile Gln Lys Ile Ile Arg
             20                  25                  30

Asp Tyr His Thr Leu Asn Val His Lys Leu Asp His
         35                  40

<210> SEQ ID NO 515
<211> LENGTH: 41
<212> TYPE: PRT
<213> ORGANISM: Plasmodium falciparum

<400> SEQUENCE: 515

Lys Arg Glu Lys Thr Gln Ile Asn Lys Thr Lys Tyr Glu Arg Gly Asp
 1               5                  10                  15

Val Ile Ile Asp Asn Thr Glu Ile Gln Lys Ile Ile Arg Asp Tyr His
             20                  25                  30

Thr Leu Asn Val His Lys Leu Asp His
```

<210> SEQ ID NO 516
<211> LENGTH: 38
<212> TYPE: PRT
<213> ORGANISM: Plasmodium falciparum

<400> SEQUENCE: 516

Lys Thr Gln Ile Asn Lys Thr Lys Tyr Glu Arg Gly Asp Val Ile Ile
1               5                   10                  15

Asp Asn Thr Glu Ile Gln Lys Ile Ile Arg Asp Tyr His Thr Leu Asn
            20                  25                  30

Val His Lys Leu Asp His
        35

<210> SEQ ID NO 517
<211> LENGTH: 44
<212> TYPE: PRT
<213> ORGANISM: Plasmodium falciparum

<400> SEQUENCE: 517

Lys Pro Leu Ala Lys Leu Arg Lys Arg Glu Lys Thr Gln Ile Asn Lys
1               5                   10                  15

Thr Lys Tyr Glu Arg Gly Asp Val Ile Ile Asp Asn Thr Glu Ile Gln
            20                  25                  30

Lys Ile Ile Arg Asp Tyr His Thr Leu Asn Val His
        35                  40

<210> SEQ ID NO 518
<211> LENGTH: 40
<212> TYPE: PRT
<213> ORGANISM: Plasmodium falciparum

<400> SEQUENCE: 518

Lys Leu Arg Lys Arg Glu Lys Thr Gln Ile Asn Lys Thr Lys Tyr Glu
1               5                   10                  15

Arg Gly Asp Val Ile Ile Asp Asn Thr Glu Ile Gln Lys Ile Ile Arg
            20                  25                  30

Asp Tyr His Thr Leu Asn Val His
        35                  40

<210> SEQ ID NO 519
<211> LENGTH: 37
<212> TYPE: PRT
<213> ORGANISM: Plasmodium falciparum

<400> SEQUENCE: 519

Lys Arg Glu Lys Thr Gln Ile Asn Lys Thr Lys Tyr Glu Arg Gly Asp
1               5                   10                  15

Val Ile Ile Asp Asn Thr Glu Ile Gln Lys Ile Ile Arg Asp Tyr His
            20                  25                  30

Thr Leu Asn Val His
        35

<210> SEQ ID NO 520
<211> LENGTH: 34
<212> TYPE: PRT
<213> ORGANISM: Plasmodium falciparum

<400> SEQUENCE: 520

Lys Thr Gln Ile Asn Lys Thr Lys Tyr Glu Arg Gly Asp Val Ile Ile

```
                 1               5                  10                 15
Asp Asn Thr Glu Ile Gln Lys Ile Ile Arg Asp Tyr His Thr Leu Asn
                20                  25                 30

Val His

<210> SEQ ID NO 521
<211> LENGTH: 32
<212> TYPE: PRT
<213> ORGANISM: Plasmodium falciparum

<400> SEQUENCE: 521

His Ile Met Leu Lys Ser Gln Met Tyr Thr Asn Glu Gly Asn Lys Ser
 1               5                  10                 15

Cys Glu Cys Ser Tyr Lys Lys Lys Ser Ser Ser Asn Lys Val His
                20                  25                 30

<210> SEQ ID NO 522
<211> LENGTH: 28
<212> TYPE: PRT
<213> ORGANISM: Plasmodium falciparum

<400> SEQUENCE: 522

Lys Ser Gln Met Tyr Thr Asn Glu Gly Asn Lys Ser Cys Glu Cys Ser
 1               5                  10                 15

Tyr Lys Lys Lys Ser Ser Ser Asn Lys Val His
                20                  25

<210> SEQ ID NO 523
<211> LENGTH: 18
<212> TYPE: PRT
<213> ORGANISM: Plasmodium falciparum

<400> SEQUENCE: 523

Lys Ser Cys Glu Cys Ser Tyr Lys Lys Lys Ser Ser Ser Asn Lys
 1               5                  10                 15

Val His

<210> SEQ ID NO 524
<211> LENGTH: 11
<212> TYPE: PRT
<213> ORGANISM: Plasmodium falciparum

<400> SEQUENCE: 524

Lys Lys Lys Ser Ser Ser Asn Lys Val His
 1               5                  10

<210> SEQ ID NO 525
<211> LENGTH: 10
<212> TYPE: PRT
<213> ORGANISM: Plasmodium falciparum

<400> SEQUENCE: 525

Lys Lys Ser Ser Ser Asn Lys Val His
 1               5                  10

<210> SEQ ID NO 526
<211> LENGTH: 9
<212> TYPE: PRT
<213> ORGANISM: Plasmodium falciparum

<400> SEQUENCE: 526

Lys Ser Ser Ser Ser Asn Lys Val His
```

```
1               5

<210> SEQ ID NO 527
<211> LENGTH: 30
<212> TYPE: PRT
<213> ORGANISM: Plasmodium falciparum

<400> SEQUENCE: 527

His Ile Met Leu Lys Ser Gln Met Tyr Thr Asn Glu Gly Asn Lys Ser
1               5                   10                  15

Cys Glu Cys Ser Tyr Lys Lys Lys Ser Ser Ser Asn Lys
            20                  25                  30

<210> SEQ ID NO 528
<211> LENGTH: 24
<212> TYPE: PRT
<213> ORGANISM: Plasmodium falciparum

<400> SEQUENCE: 528

His Ile Met Leu Lys Ser Gln Met Tyr Thr Asn Glu Gly Asn Lys Ser
1               5                   10                  15

Cys Glu Cys Ser Tyr Lys Lys Lys
            20

<210> SEQ ID NO 529
<211> LENGTH: 23
<212> TYPE: PRT
<213> ORGANISM: Plasmodium falciparum

<400> SEQUENCE: 529

His Ile Met Leu Lys Ser Gln Met Tyr Thr Asn Glu Gly Asn Lys Ser
1               5                   10                  15

Cys Glu Cys Ser Tyr Lys Lys
            20

<210> SEQ ID NO 530
<211> LENGTH: 22
<212> TYPE: PRT
<213> ORGANISM: Plasmodium falciparum

<400> SEQUENCE: 530

His Ile Met Leu Lys Ser Gln Met Tyr Thr Asn Glu Gly Asn Lys Ser
1               5                   10                  15

Cys Glu Cys Ser Tyr Lys
            20

<210> SEQ ID NO 531
<211> LENGTH: 36
<212> TYPE: PRT
<213> ORGANISM: Plasmodium falciparum

<400> SEQUENCE: 531

His Asn Asn His Asn Ile Gln Ile Tyr Lys Asp Lys Arg Ile Asn Phe
1               5                   10                  15

Met Asn Pro His Lys Val Met Tyr His Asp Asn Met Ser Lys Asn Glu
            20                  25                  30

Arg Thr Glu Lys
        35

<210> SEQ ID NO 532
<211> LENGTH: 30
<212> TYPE: PRT
```

-continued

```
<213> ORGANISM: Plasmodium falciparum

<400> SEQUENCE: 532

His Asn Asn His Asn Ile Gln Ile Tyr Lys Asp Lys Arg Ile Asn Phe
1               5                   10                  15

Met Asn Pro His Lys Val Met Tyr His Asp Asn Met Ser Lys
            20                  25                  30

<210> SEQ ID NO 533
<211> LENGTH: 21
<212> TYPE: PRT
<213> ORGANISM: Plasmodium falciparum

<400> SEQUENCE: 533

His Asn Asn His Asn Ile Gln Ile Tyr Lys Asp Lys Arg Ile Asn Phe
1               5                   10                  15

Met Asn Pro His Lys
            20

<210> SEQ ID NO 534
<211> LENGTH: 17
<212> TYPE: PRT
<213> ORGANISM: Plasmodium falciparum

<400> SEQUENCE: 534

His Lys Val Met Tyr His Asp Asn Met Ser Lys Asn Glu Arg Thr Glu
1               5                   10                  15

Lys

<210> SEQ ID NO 535
<211> LENGTH: 11
<212> TYPE: PRT
<213> ORGANISM: Plasmodium falciparum

<400> SEQUENCE: 535

His Lys Val Met Tyr His Asp Asn Met Ser Lys
1               5                   10
```

REPLIKIN PEPTIDES IN RAPID REPLICATION OF GLIOMA CELLS AND IN INFLUENZA EPIDEMICS

CROSS REFERENCE TO OTHER APPLICATIONS

This application is a divisional application of U.S. Ser. No. 11/590,852, filed Nov. 1, 2006, which is a continuation application of U.S. Ser. No. 10/105,232 (now U.S. Pat. No. 7,189,800), filed Mar. 26, 2002, which is a Continuation-In-Part Application of U.S. Ser. No. 09/984,057 (now U.S. Pat. No. 7,420,028), filed Oct. 26, 2001, which claims priority from Provisional Application 60/303,396, filed Jul. 9, 2001 and Provisional Application US 60/278,761 filed Mar. 27, 2001, the subject matter of which is incorporated by reference hereto.

FIELD OF THE INVENTION

This invention relates to the identification and use of Replikins, a class of peptides that share structural characteristics. In particular, this invention relates to Replikins which have been identified in influenza viruses and their use in designing influenza virus vaccines.

BACKGROUND OF THE INVENTION

Influenza is an acute respiratory illness of global importance. Despite international attempts to control influenza virus-outbreaks through vaccination influenza infections remain an important cause of morbidity and mortality. Worldwide influenza pandemics have occurred at irregular and previously unpredictable intervals throughout history and it is expected that they will continue to occur in the future. The impact of pandemic influenza is substantial in terms of morbidity, mortality and economic cost.

Influenza vaccines remain the most effective defense against influenza virus, but because of the ability of the virus to mutate and the availability of non-human host reservoirs it is expected that influenza will remain an emergent or re-emergent infection. Global influenza surveillance indicates that influenza viruses may vary within a country and between countries and continents during an influenza season. Virologic surveillance is of importance in monitoring antigenic shift and drift. Disease surveillance is also important in assessing the impact of epidemics. Both types of information have provided the basis of vaccine composition and the correct use of antivirals. However, to date there has been only annual post hoc hematological classification of the increasing number of emerging influenza virus strains, and no specific chemical structure of the viruses has been identified as an indicator of approaching influenza epidemic or pandemic. Currently, the only basis for annual classification of influenza virus as active, inactive or prevalent in a given year is the activities of the virus hemagglutinin and neuraminidase proteins. No influenza viral chemical structure has been identified that can be used for quantitative warning of epidemics or pandemics or to design more effective and safer vaccines.

Because of the annual administration of influenza vaccines and the short period of time when a vaccine can be administered, strategies directed at improving vaccine coverage are of critical importance.

Another disease which has proved difficult to treat and for which there is no effective vaccine is malaria. Malaria causes much physical and economic hardship in tropical regions. Malaria is caused by *Plasmodium falciparum*, which has proved to be extremely resistant to treatment and to date, a vaccine for malaria remains elusive. Thus, there is a need for effective malaria vaccines and methods of treating or preventing the disease.

SUMMARY OF THE INVENTION

In one aspect of the invention there are provided isolated influenza virus peptides containing a Replikin sequence. The influenza virus peptides comprise from 7 to about 50 amino acids including (1) at least one lysine residue located six to ten amino acid residues from a second lysine residue; (2) at least one histidine residue; and (3) at least 6% lysine residues.

In another aspect of the invention there is provided a process for stimulating the immune system of a subject to produce antibodies that bind specifically to an influenza virus Replikin sequence, said process comprising administering to the subject an effective amount of a dosage of a composition comprising at least one influenza virus replikin peptide. In a preferred embodiment the composition comprises at least one peptide that is present in an emerging strain of influenza virus.

The present invention also provides antibodies that bind specifically to an influenza virus Replikin, as defined herein, as well as antibody cocktails containing a plurality of antibodies that specifically bind to influenza virus Replikins. In one embodiment of the invention, there are provided compositions comprising an antibody or antibodies that specifically bind to an influenza Replikin and a pharmaceutically acceptable carrier.

The present invention also provides therapeutic compositions comprising one or more of isolated influenza virus peptides having from 7 to about 50 amino acids comprising 1) at least one lysine residue located six to ten residues from a second lysine residue; (2) at least one histidine residue; and (3) at least 6% lysine residues, and a pharmaceutically acceptable carrier.

In another aspect of the invention there is provided an antisense nucleic acid molecule complementary to an influenza virus hemagglutinin Replikin mRNA sequence, said Replikin mRNA sequence having from 7 to about 50 amino acids comprising (1) at least one lysine residue located six to ten residues from a second lysine residue; (2) at least one histidine residue; and (3) at least 6% lysine residues.

In yet another aspect of the invention, there is provided a method of stimulating the immune system of a subject to produce antibodies to influenza virus comprising administering an effective amount of at least one influenza virus Replikin peptide having from 7 to about 50 amino acids comprising (1) at least one lysine residue located six to ten amino acid residues from a second lysine residue; (2) at least one histidine residue; and (3) at least 6% lysine residues.

In another aspect, there is provided a method of selecting an influenza virus peptide for inclusion in an influenza virus vaccine comprising (1) obtaining at least one isolate of each strain of a plurality of strains of influenza virus, (2) analyzing the hemagglutinin amino acid sequence of the at least one isolate of each strain of the plurality of strains of influenza virus for the presence and concentration of Replikin sequences, (3) comparing the concentration of Replikin sequences in the hemagglutinin amino acid sequence of the at least one isolate of each strain of the plurality of strains of influenza virus to the concentration of Replikin sequences observed in the hemagglutinin amino acid sequence of each of the strains at least one earlier time period to provide the concentration of Replikins for at least two time periods, said at least one earlier time period being within about six months to about three years prior to step (1), (4) identifying the strain of influenza virus having the highest increase in concentration of Replikin sequences during the at least two time periods, (5) selecting at least one Replikin sequence present in the strain of influenza virus peptide identified in step (4) as a peptide for inclusion in an influenza virus vaccine.

The present invention also provides a method of making an influenza virus vaccine comprising (1) identifying a strain of influenza virus as an emerging strain, (2) selecting at least one Replikin sequence present in the emerging strain as a peptide template for influenza virus vaccine manufacture, (3) synthesizing peptides having the amino acid sequence of the at least one Replikin sequence selected in step (2), and (4) combining a therapeutically effective amount of the peptides of step (4) with a pharmaceutically acceptable carrier and/or adjuvant.

In another aspect, the invention is directed to a method of identifying an emerging strain of influenza virus for diagnostic or therapeutic purposes comprising (1) obtaining at least one isolate of each strain of a plurality of strains of influenza virus, (2) analyzing the hemagglutinin amino acid sequence of the at least one isolate of each strain of the plurality of strains of influenza virus for the presence and concentration of Replikin sequences, (3) comparing the concentration of Replikin sequences in the hemagglutinin amino acid sequence of the at least one isolate of each strain of the plurality of strains of influenza virus to the concentration of Replikin sequences observed in the hemagglutinin amino acid sequence of each of the strains at least one earlier time period to provide the concentration of Replikins for at least two time periods, said at least one earlier time period being within about six months to about three years prior to step (1), and (4) identifying the strain of influenza virus having the highest increase in concentration of Replikin sequences during the at least two time periods.

In yet another aspect of the invention, there is provided an influenza virus vaccine comprising at least one isolated Replikin present in the hemagglutinin protein of an emerging strain of influenza virus and a pharmaceutically acceptable carrier and/or adjuvant.

Also provided by the present invention is a method of preventing or treating influenza virus infection comprising administering to a patient in need thereof a vaccine comprising at least one isolated Replikin present in the hemagglutinin protein of an emerging strain of influenza virus and a pharmaceutically acceptable carrier and/or adjuvant.

In another aspect of the invention, there are provided vaccines and methods for preventing or treating malaria. The malaria vaccines comprise at least one isolated *Plasmodium falciparum* Replikin. The present invention also provides methods for treating or preventing malaria comprising administering to a patient an effective amount of a vaccine comprising at least one isolated *Plasmodium falciparum* Replikin.

Also provided by the present invention are antibodies, antibody cocktails and compositions that comprise antibodies that specifically bind to a Replikin or Replikins present in a malaria antigen of *Plasmodium falciparum*.

As used herein, the term "peptide" refers to a compound of two or more amino acids in which the carboxyl group of one is united with an amino group of another, forming a peptide bond. The term peptide is also used to denote the amino acid sequence encoding such a compound. Thus, a peptide sequence may be a subsequence of a larger polypeptide sequence. As used herein, a Replikin peptide is a peptide having 7 to about 50 amino acids comprising (1) at least one lysine residue located six to ten amino acid residues from a second lysine residue; (2) at least one histidine residue; and (3) at least 6% lysine residues. Similarly, a replikin sequence is the amino acid sequence encoding such a peptide.

The phrase "emerging strain" as used herein refers to a strain of influenza virus identified as having an increasing concentration of Replikin sequences in its hemagglutinin and/or neuraminidase protein sequence, relative to the concentration of replikins in other strains of influenza virus. The increase in concentration occurs over a period of at least about six months, and preferably over a period of at least about one year, most preferably over a period of at least about three years or more.

BRIEF DESCRIPTION OF THE DRAWINGS

FIG. 7 is a graph showing the concentration of Replikins observed in hemagglutinin of influenza B and influenza A strain, H1N1, on a year by year basis from 1918 through 2001.

DETAILED DESCRIPTION OF THE INVENTION

Figure 1:
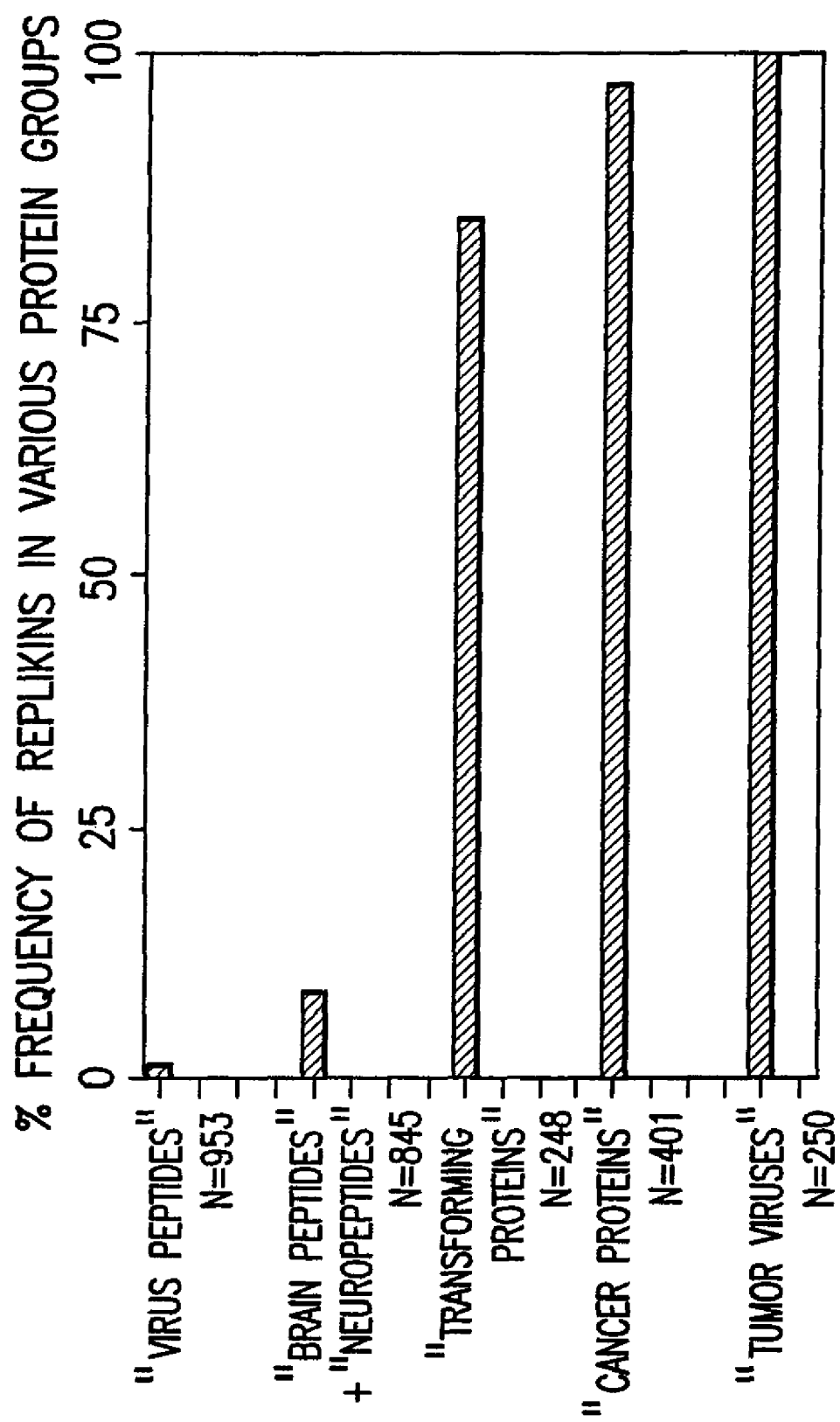
FIG. 1 is a bar graph depicting the frequency of occurrence of replikins in various protein groups.

The present invention provides methods for predicting future epidemics or pandemics of influenza virus, and vaccines and methods of designing effective vaccines against influenza virus. Identification of a new family of small peptides related to the phenomenon of rapid replication, referred to herein as Replikins, provides new targets for influenza virus detection and influenza vaccine development. Identification of this new family of peptides also provides for the detection of malaria and provides new targets for malaria vaccine development.

The first Replikin sequence to be identified was the cancer cell Replikin found in a brain cancer protein, malignin, which was demonstrated to be enriched ten-fold during rapid anaerobic replication of glioblastoma multiforme (glioma) cells. (FIG. 2) Malignin is a 10 KDa portion of the 250 KDa glycoprotein 10B, which was isolated in vivo and in vitro from membranes of glioblastoma multiforme (glioma) cells. Hydrolysis and mass spectroscopy of malignin revealed a 16-mer peptide sequence, ykagvaflhkndide (SEQ ID NO.: 4), which is referred to herein as the glioma Replikin and which includes the shorter peptide, kagvaflhkk (SEQ ID NO.: 1), both of which apparently are absent in the normal human genome.

Table 1 illustrates how the sequence of the glioma Replikin, the 16-mer peptide sequence, ykagvaflhkkndide (SEQ ID NO.: 4) was determined.

TABLE 1

16-mer peptide sequence ykagvaflhkkndide obtained from malignin by hydrolysis and mass spectrometry

| Seq ID NO. | Fragment Identified | MH+ (mass) | Sequence | Auto-hydrolysis of malignin free in solution | Auto-hydrolysis of malignin immobilized on bromoacetyl cellulose | Micro-waved 5 seconds | Micro-waved 30 seconds |
|---|---|---|---|---|---|---|---|
| 19 | 1-3 | 381.21 | ( )yka(g) | | | | + |
| 20 | 1-5 | 537.30 | ( )ykagv(a) | | + | | |
| 21 | 2-6 | 445.28 | (y)kagva(f) | | + | | |
| 22 | 2-7 | 592.35 | (Y)kagyaf(l) | | | + | |
| 23 | 4-11 | 899.55 | (a)gvaflhkk(n) | | | | + |
| 24 | 5-7 | 336.19 | (g)vaf(l) | | | | + |
| 25 | 6-7 | 237.12 | (v)af(l) | + | | | |
| 26 | 6-10 | 615.36 | (v)aflhk(k) | | | | + |
| 27 | 6-10 | 615.36 | (v)aflhk(k) | + | | | |
| 28 | 6-12 | 857.50 | (v)aflhkkn(d) | | + | | |
| 29 | 6-12 | 857.50 | (v)afhkkn(d) | + | | | |
| 30 | 7-8 | 279.17 | (a)fl(h) | | | + | |
| 31 | 10-16 | 861.43 | (h)kkndide( ) | | + | | |
| 32 | 11-14 | 489.27 | (k)kndi(d) | | + | | |
| 33 | 12-15 | 476.2- | (k)ndid(e) | + | | | |

When the 16-mer glioma Replikin was synthesized and injected as a synthetic vaccine into rabbits, abundant antimalignin antibody was produced. (Bogoch et al., Cancer Detection and Prevention, 26(Supp. 1): 402 (2002). The concentration of antimalignin antibody in serum in vivo has been shown to relate quantitatively to the survival of cancer patients. (Bogoch et al., Protides of Biological Fluids, 31:739-747 (1984). In vitro antimalignin antibodies have been shown to be cytotoxic to cancer cells at a concentration of picograms (femtomolar) per cancer cell. (Bogoch et al., Cancer Detection and Prevention, 26(Supp. 1): 402 (2002).

Studies carried out by the inventors showed that the glioma Replikin is not represented in the normal healthy human genome. Consequently, a search for the origin and possible homologues of the Replikin sequence was undertaken by analysis of published sequences of various organisms.

By using the 16-mer glioma Replikin sequence as a template and constructing a recognition proteomic system to visually scan the amino acid sequences of proteins of several different organisms, a new class of peptides, the Replikins, was identified. The present invention provides a method for identifying nucleotide or amino acid sequences that include a Replikin sequence. The method is referred to herein as a 3-point-recognition method. By use of the "3-point recognition" method, described herein below, a new class of peptides was revealed in algae, yeast, fungi, amoebae, bacteria, plant and virus proteins having replication, transformation, or redox functions. Surprisingly, the Replikin peptides were found to be concentrated in larger 'replicating' and 'transforming' proteins (so designated by their investigators, See Table 2). No sequences were found to be identical to the malignin 16-mer peptide.

Table 2 illustrates several Replikin sequences that were identified by the 3-point recognition method of the invention.

TABLE 2

Examples of replikins in various organisms—prototype: Glioma replikin* kagvaflhkk (SEQ ID No.:1)

| | SEQ ID NO. | | |
|---|---|---|---|
| Algae: | 34 | Caldophera prolifera | kaskftkh |
| | 35 | Isolepisprolifera | kaqaetgeikgh |
| Yeast: | 36 | Schizosaccharomyces pombe | ksfkypkkhk |
| | 37 | Oryza sativa | kkaygnelhk |
| | 2 | Sacch. cerevisiae replication binding protein | hsikrelgiifdk |
| Fungi: | | Isocitrate lyase ICI 1, Penicillium marneffei | kvdivthqk |
| | 38 | DNA-dependent RNA polymerase 11, Discula destructiva | kleedaayhrkk |
| | 39 | Ophiostoma novo-ulm 1, RNA in Dutch elm disease | kvilplrgnikgiffkh |
| | 40 | fungus | |
| Amoeba: | 41 | Entamoeba invadens, histone H2B | klilkgdlnkh |
| Bacteria: | 42 | Pribosomal protein replication factor, Helicobacter pylori | ksvhaflk |
| | | Replication-associated protein Staph. aureus | |
| | 10 | Mycoplasma pulmonic, chromosome replication | kkektthnk |
| | 43 | Macrophage infectivity potentiator, L. legionella | kvhffqlkk |
| | 90 | Bacillus anthracis | kihlisvkk |
| | 91 | Bacillus anthracis | hvkkekeknk |

TABLE 2-continued

Examples of replikins in various organisms—prototype: Glioma replikin* kagvaflhkk
(SEQ ID No.:1)

|  | SEQ ID NO. |  |  |
| --- | --- | --- | --- |
|  | 92 | *Bacillus anthracis* | khivkievk |
|  | 93 | *Bacillus anthracis* | kkkkikdiygkdallh |
|  | 94 | *Bacillus anthracis* | kwekikqh |
|  | 95 | *Bacillus anthracis* | kklqipppiepkkddiih |
|  | 96 | *Bacillus anthracis* | hnryasnivesayllilnew-knniqsdlikk |
|  | 97 | *Bacillus anthracis* | havddyagylldknqsdlv-tnskk |
|  | 98 | *Bacillus anthracis* | haerlkvqknapk |
| Plants: | 44 | *Arabidopsis thaliana*, prolifera | kdhdfdgdk |
|  | 45 | *Arabidopsis thaliana*, cytoplasmic ribosomal | krnkglkqkkah |
|  | 46 | *Arabidopsis thaliana*, DNA binding protein | kelssttqeksh |
| Viruses: | 9 | Replication associated protein A [Maize streak virus] | kekkpskdeimrdiish |
|  | 11 | Bovine herpes virus 4, DNA replication protein | hkinitngqk |
|  | 12 | Meleagrid herpesvirus 1, replication binding protein | hkdlyrllmk |
|  | 47 | Feline immunodeficiency | hlkdyklvk |
|  | 3 | Foot and Mouth Disease (O) | hkqkivapvk |
|  | 5 | HIV Type 1 | kcfncgkegh |
|  | 7 | HIV Type 2 | kcwncgkegh |
|  | 99 | Small Pox Virus (*Variola*) | khynnitwyk |
|  | 100 | Small Pox Virus (*Variola*) | kysqtgkeliih |
|  | 101 | Small Pox Virus (*Variola*) | hyddvrikndivvsrck |
|  | 102 | Small Pox Virus (*Variola*) | hrfklildski |
|  | 103 | Small Pox Virus (*Variola*) | kerghnyyfek |
| Tumor Viruses: | 48 | Rous sarcoma virus tyrosine-protein kinase | kkkhek |
|  | 49 | v-yes, avian sarcoma | kklrhdk |
|  | 50 | c-yes, colon cancer, malignant melanoma | kklrhdk |
|  | 51 | v-srcC, avian sarcoma | kklrhek |
|  | 52 | c-src, colon, mammary, pancreatic cancer | kkkhek |
|  | 53 | Neuroblastoma RAS viral (v-ras) oncogene | kqahelak |
|  | 54 | VPl (major capsid protein) [Polyamavirus sp.] | kthrfskh |
|  | 55 | Sindbis | knlhekik |
|  | 56 | El [Human papilloamavirus type 71] | khrpllqlk |
|  | 57 | v-erbB from AEV and c-erb | kspnhvk |
|  | 58 | v-fms (feline sarcoma) | knihlekk |
|  | 59 | c-fms (acute and chronic myelomonocytic tumors) | knihlekk |
|  | 60 | large t-antigen I [Polyomavirus sp.] | kphlaqslek |
|  | 61 | middle t-antigen [Polyomavirus sp,]- | kqhrelkdk |
|  | 62 | small t-antigen [Polyomavirus sp], | kqhrelkdk |
|  | 63 | v-abl, murine acute leukemia | kvpvlisptlkh |
|  | 64 | Human T-cell lymphotropic virus type 2 | kslllevdkdish |
|  | 65 | c-kit, GI tumors, small cell lung carcinoma | kagitimvkreyh |
|  | 18 | Hepatitis C | hyppkpgcivpak |
| Trans-forming Proteins: | 66 | Transforming protein myb | ksgkhlgk |
|  | 67 | Transforming protein myc, Burkitt lymphoma | krreqlkhk |
|  | 68 | Ras-related GTP-binding protein | ksfevikvih |
|  | 69 | Transforming protein ras (teratocarcinoma) | kkkhtvkk |
|  | 70 | TRAF-associated NF•kB activator TANK | kaqkdhlsk |
|  | 71 | RFP transforming protein | hlkrvkdlkk |
|  | 72 | Transforming protein D (S.C.) | kygspkhrlik |
|  | 73 | Papilloma virus type 11, transforming protein | klkhilgkarfik |
|  | 74 | Protein tryosine kinase (EC 2.7.1.112slk | kgdhvkhykirk |
|  | 75 | Transforming protein (axl(−)) | keklrdvmvdrhk |
|  | 76 | Transforming protein (N-myc) | klqarqqqllkkieh |
|  | 77 | Fibroblast growth factor 4 (Kaposi sarcoma) | kkgnrvsptmkvth |
| Cancer Cell Proteins: | 78 | Matrix metaloproteinase 7 (uterine) | keiplhfrk |
|  | 79 | Transcription factor 7-like | kkkphikk |
|  | 80 | Breast cancer antigen NY-BR-87 | ktrhdplak |
|  | 81 | BRCA-1-Associated Ring Domain Protein (breast) | khhpkdnlik |
|  | 82 | 'Autoantigen from a breast tumor' | khkrkkfrqk |
|  | 83 | Glioma Replikin (this study) | kagvaflhkk |
|  | 84 | Ovarian cancer antigen | khkrkkfrqk |
|  | 85 | EE L leukemia | kkkskkhkdk |
|  | 86 | Proto-oncogene tyrosine-protein kinase C-ABLE | hksekpalprk |
|  | 87 | Adenomatosis polyposis coli | kkkkpsrlkgdnek |
|  | 88 | Gastric cancer transforming protein | ktkkgnrvsptmkvth |
|  | 89 | Transforming protein (K-RAS 2B), lung | khkekmskdgkkkkkksk |

Identification of an amino acid sequence as a Replikin or as containing a Replikin, i.e., a homologue of the glioma peptide, kagvaflhkk, requires that the three following requirements be met. The peptide sequence must have (1) at least one lysine residue located six to ten residues from another lysine residue; (2) at least one histidine residue; and (3) a composition of at least 6% lysine within an amino acid sequence of 7 to about 50 residues.

Databases were searched using the National Library of Medicine keyword "PubMed" descriptor for protein sequences containing Replikin sequences. Over 4,000 protein sequences were visually examined for homologues. Sequences of all individual proteins within each group of PubMed-classified proteins were visually scanned for peptides meeting the three above-listed requirements. An infrequent occurrence of homologues was observed in "virus peptides" as a whole (1.5%) (N=953), and in other peptides not designated as associated with malignant transformation or replication such as "brain peptides" and "neuropeptides" (together 8.5%) (N=845). However, surprisingly, homologues were significantly more frequently identified in large "replicating proteins," which were identified as having an established function in replication in bacteria, algae, and viruses. Even more surprising was the finding that Replikin homologues occurred in 100% of "tumor viruses" (N=250), in 97% of "cancer proteins" (N=401), and in 85% of "transforming viruses" (N=248). These results suggest that there are shared properties of cancer pathogenesis regardless of cell type and suggest a role of viruses in carcinogenesis, i.e., conversion of cells from a transformed albeit dormant state to a more virulent actively replicating state.

To permit classification of subtypes of Replikins, additional or "auxiliary specifications" to the basic "3-point-recognition" requirements may be added: (a) on a structural basis, such as the common occurrence of adjacent di- and polylysines in cancer cell proteins (e.g., transforming protein P21B(K-RAS 2B), lung, Table 2, SEQ ID NO.: 89), and other adjacent di-amino acids in TOLL-like receptors, or b) on a functional basis, such as exhibiting ATPase, tyrosine kinase or redox activity as seen in Table 2.

Whether Replikin structures are conserved or are subject to extensive natural mutation was examined by scanning the protein sequences of various isolates of foot and mouth disease virus (FMDV), where mutations in proteins of these viruses have been well documented worldwide for decades. Protein sequences of FMDV isolates were visually examined for the presence of both the entire Replikin and each of the component Replikin amino acid residues observed in a particular Replikin. For example, in the protein VP1 of FMDV type O, the Replikin (SEQ ID NO.: 3) "hkqkivapvk" was found to be conserved in 78% of the 236 isolates reported in PubMed, and each amino acid was found to be conserved in individual isolates as follows: his, 95.6%; lys, 91.8%; gln, 92.3%; lys, 84.1%; ile, 90.7%; val, 91.8%; ala, 97.3%; pro, 96.2%; ala val, 75.4%; and lys, 88.4%. The high rate of conservation suggests structural and functional stability of the Replikin structure. Similarly, sequence conservation was observed in different isolates of HIV for its Replikins, such as (SEQ ID NO.: 5) "kcfncgkegh" or (SEQ ID NO.: 6) "kvylawvpahk" in HIV Type 1 and (SEQ ID NO.: 7) "kcwncgkegh" in HIV Type 2 (Table 2). Other examples of conservation are seen in the constant presence of malignin in successive generations, over ten years of tissue culture of glioma cells, and by the constancy of affinity of the glioma Replikin for antimalignin antibody isolated by immunoadsorption from 8,090 human sera from the U.S., U.K., Europe and Asia (e.g., FIG. 5 and U.S. Pat. No. 6,242,578 B1).

Figure 2:
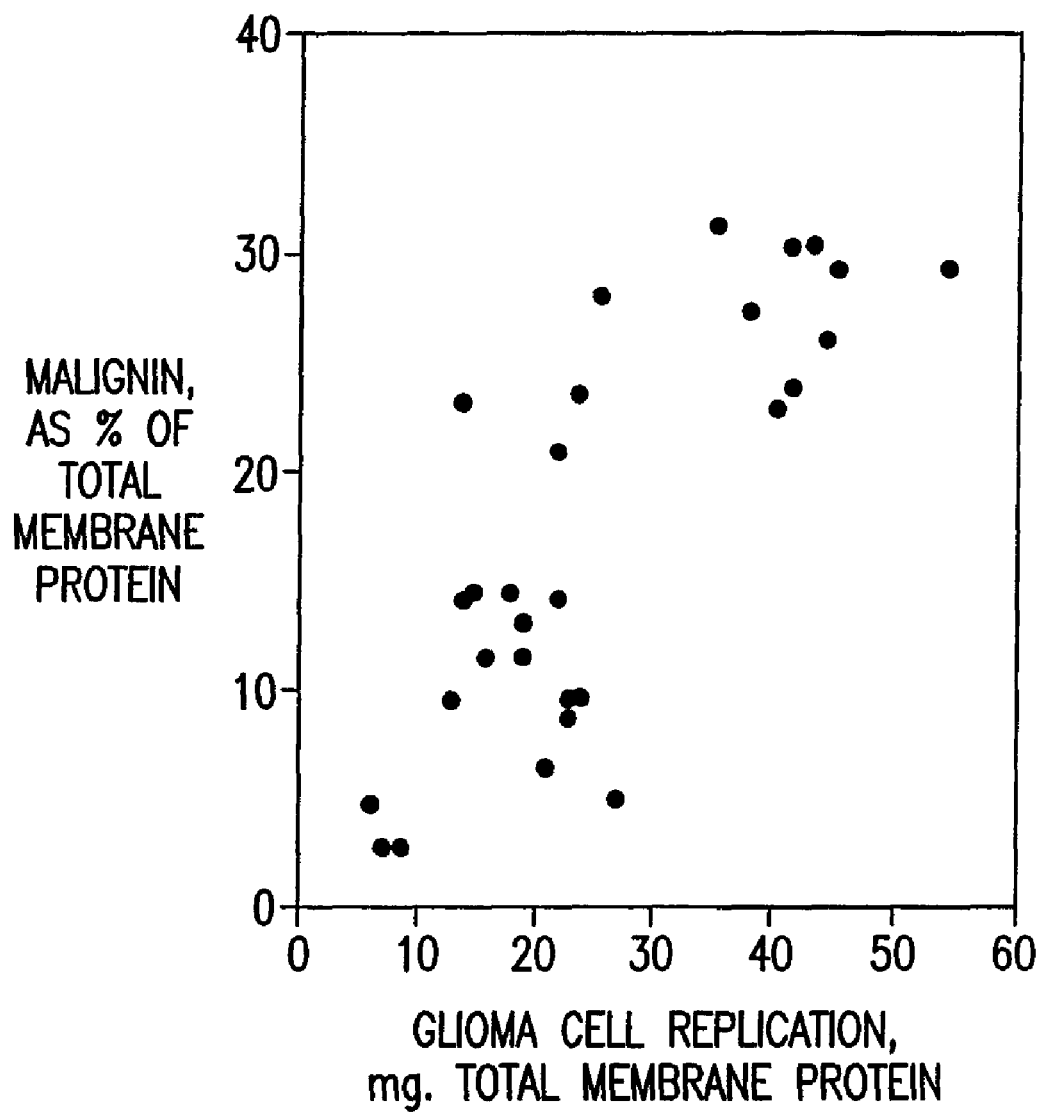
FIG. 2 is a graph depicting the percentage of malignin per milligram total membrane protein during anaerobic replication of glioblastoma cells.

As seen in FIG. 2, during anaerobic respiration when the rate of cell replication is increased, malignin is enriched. That is, malignin is found to increase not simply in proportion to the increase in cell number and total membrane proteins, but is enriched as much as tenfold in concentration, starting with 3% at rest and reaching 30% of total membrane protein. This clear demonstration of a marked increase in Replikin concentration with glioma cell replication points to and is consistent with the presence of Replikins here sought by the 3-point recognition method and found in the proteins of various organisms which were found by mutation studies and other previous studies to be critical to replication. For example, Replikins were identified in such proteins as "*Saccharomyces cerevisiae* replication binding protein" (SEQ ID NO.: 2) (hsikrelgiifdk); the "replication associated protein A of maize streak virus" (SEQ ID NO.: 8) (kyivcareahk) and (SEQ ID NO.: 9) (kekkpskdeimrdiish); the "replication-associated protein of *Staphylococcus aureus*" (SEQ ID NO.: 10) (kkektthnk); the "DNA replication protein of bovine herpes virus 4" (SEQ ID NO.: 11) (hkinitngqk); and the "Mealigrid herpes virus 1 replication binding protein" (SEQ ID NO.: 12) (hkdlyrllmk). Previous studies of tomato leaf curl gemini virus show that the regulation of virus accumulation appears to involve binding of amino acids 1-160 of the "replicating protein" of that virus to leaf DNA and to other replication protein molecules during virus replication. Analysis of this sequence showed that amino acids 1-163 of this "replicating protein" contain five Replikins, namely: (SEQ ID NO.: 13) kfrinaknyfltyph, (SEQ ID NO.: 14) knletpvnklfiricrefh, (SEQ ID NO.: 15) hpniqaaksstdvk, (SEQ ID NO.: 16) ksstdvkaymdkdgdvldh, and (SEQ ID NO.: 17) kasalnilrekapkdfvlqfh.

Table 2 shows that Replikin-containing proteins also are associated frequently with redox functions, and protein synthesis or elongation, as well as with cell replication. The association with metal-based redox functions, the enrichment of the Replikin-containing glioma malignin concentration during anaerobic replication, and the cytotoxicity of antimalignin at low concentrations (picograms/cell) (FIG. 4c-f), all suggest that the Replikins are related to central respiratory functions, which are perhaps less often subjected to the mutations characteristic of proteins of more superficial location or less central survival function.

Of particular interest, it was observed that at least one Replikin per 100 amino acids was found to be present in the hemagglutinin proteins of almost all of the individual strains of influenza viruses examined. The replikin sequences that were observed to occur in the hemagglutinin proteins of isolates of each of the four prevalent strains of influenza virus, influenza B, H1N1, H2N2, and H3N2, for each year that amino acid sequence data are available (1902-2001) are shown in Tables 3, 4, 5 and 6, below.

TABLE 3

Replikin Sequences present in hemagglutinins of Influenza B viruses in each year for which amino acid sequences were available (1902-2001).

| Influenza B Replikins | Year Detected in Influenza B strain (Peak in FIG. 7: EB1 EB2) |
|---|---|
| kshfanlk (SEQ ID NO. 104) | 1902, 19, 24, 38, 40, 43, <u>51</u>, 59, 75, 76, <u>77</u>, 89, 90, 93, 97, 98, 99, 00, 01 |
| kshfanlkgtk (SEQ ID NO. 105) | 1902, 19, 24, 38, 40, 43, <u>51</u>, 59, 75, 76, <u>77</u>, 89, 90, 93, 97, 98, 99, 00, 01 |
| kshfanlkgtktrgklcpk (SEQ ID NO. 106) | 1902, 19, 24, 38, 40, 43, <u>51</u>, 59, 75, 76, <u>77</u>, 89, 90, 93, 97, 98, 99, 00, 01 |
| hekygglnk (SEQ ID NO. 107) | 1902, 19, 24, 38, 40, 43, <u>51</u>, 59, 75, 76, <u>77</u>, 89, 90, 93, 97, 98, 99, 00, 01 |
| hekygglnksk (SEQ ID NO. 108) | 1902, 19, 24, 38, 40, 43, <u>51</u>, 59, 75, 76, <u>77</u>, 89, 90, 93, 97, 98, 99, 00, 01 |
| hekygglnkskpyytgehak (SEQ ID NO. 109) | 1902, 19, 24, 38, 40, 43, <u>51</u>, 59, 75, 76, <u>77</u>, 89, 90, 93, 97, 98, 99, 00, 01 |
| hakaigncpiwvk (SEQ ID NO. 110) | 1902, 19, 24, 38, 40, 43, <u>51</u>, 59, 75, 76, <u>77</u>, 89, 90, 93, 97, 98, 99, 00, 01 |
| hakaigncpiwvktplklangtk (SEQ ID NO. 111) | 1902, 19, 24, 38, 40, 43, <u>51</u>, 59, 75, 76, <u>77</u>, 89, 90, 93, 97, 98, 99, 00, 01 |
| hakaigncpiwvktplklangtkyrppak (SEQ ID NO. 112) | 1902, 19, 24, 38, 40, 43, <u>51</u>, 59, 75, 76, <u>77</u>, 89, 90, 93, 97, 98, 99, 00, 01 |
| hakaigncpiwvktplklangtkyrppakllk (SEQ ID NO. 113) | 1902, 19, 24, 38, 40, 43, <u>51</u>, 59, 75, 76, <u>77</u>, 89, 90, 93, 97, 98, 99, 00, 01 |
| hfanlkgtktrgk (SEQ ID NO. 114) | 1919, 76, 89, 90, 99, 00, 01 |
| hfanlkgtktrgklcpk (SEQ ID NO. 115) | 1919, 76, 90 00, 01 |
| hsdneiqmvklygdsk (SEQ ID NO. 116) | 1919 |
| hsdneiqdkmvklygdskpqk (SEQ ID NO. 117) | 1919 |
| hsdneiqmvklygdskpqk (SEQ ID NO. 118) | 1919, 24, 97, 98, 00 |
| k(a/v)silhevk (SEQ ID NO. 119) | 1919, 40, 59, 90, 93 |
| kctgtipsakasilh (SEQ ID NO. 120) | 1919, 00 |
| kctgtipsakasilhevk (SEQ ID NO. 121) | 1919, 93 |
| kygglnkskpyytgeh (SEQ ID NO. 122) | 1919 |
| kvwcasgrskvikgslptigeadclh (SEQ ID NO. 123) | 1919, 38, 40, 43, 59, 75, 76, <u>77</u>, 89, 90, 98, 99, 00 |
| kpyytgehak (SEQ ID NO. 124) | 1919, 38, 40, 59, 89, 90, 93, 97, 98, 01 |
| kcmgtipsakasilhevk (SEQ ID NO. 125) | 1924, 43, 75, 76, <u>77</u>, 93 |
| hnvinaekapggpyk (SEQ ID NO. 126) | 1938, 93, 97, 00 |
| hsdnetqmaklygdsk (SEQ ID NO. 127) | 1938, 93, 97, 00 |

TABLE 3-continued

Replikin Sequences present in hemagglutinins of Influenza B viruses in each year for which amino acid sequences were available (1902-2001).

| Influenza B Replikins | Year Detected in Influenza B strain (Peak in FIG. 7: EB1 EB2) |
|---|---|
| hgvavaadlkstqeaink (SEQ ID NO. 128) | 1940, 59, 00 |
| hgvavaadlkstqeainkdtistqeaink (SEQ ID NO. 129) | 1940 |
| klygdskpqkftssangvtth (SEQ ID NO. 130) | 1943, 75, 76, 77, 93, 97, 00 |
| hsdnetqmaklygdskpqk (SEQ ID NO. 131) | 1943, 75, 76, 77, 93 |
| hfanlkgtqtrgk (SEQ ID NO. 132) | 1959 |
| kprsalkckgfh (SEQ ID NO. 133) | 1988 |
| kskpyytgehakai(g/a)ncpiwvk (SEQ ID NO. 134) | 2000 |

1. Influenza B has not been responsible for any human pandemic (global distribution).
2. Abbreviation for years: eg. "19" = 1919, "01" = 2001.
3. The first year that a given replikin appears is indicated at the beginning of the series of years in which that replikin has been found.
4. Overlapping replikin sequences are listed separately.
5. Increase in number of new replikin structures occurs in years of epidemics (underlined): eg. 1951 and 1977 and correlates with increased total replikin concentration (number of replikins per 100 amino acid residues). See FIG. 7.

TABLE 4

H1N1 Replikin Sequences present in H1N1 hemagglutinins of Influenza viruses in each year for which amino acid sequences were available (1918-2000)

| H1N1 Replikin H1N1 Strain | Year Detected in Influenza (Peak in FIG. 7: P1 E1 E1.1, 1.2, 1.3 E1.4) |
|---|---|
| hp(v/i)tigecpkyv(r/k)(s/t)(t/a)k (SEQ ID NO. 135) | 1918, 25, 28, 30, 31, 35, 47, 48, 51, 52, 55, 56, 57, 59, 63, 77, 79, 80, 81, 85, 87, 88, 89, 91, 92, 95, 96, 97, 98, 99, 00 |
| hdsnvknly(e/g)kv(k/r)(n/s)ql(k/r)nnak (SEQ ID NO. 136) | 1918, 28, 30, 31, 77, 79, 80, 88, 91, 95, 98 |
| hdsnvknly(e/g)kv(k/r)(n/s)qlk (SEQ ID NO. 137) | 1918, 28, 30, 31, 77, 79, 80, 88, 91, 95, 98 |
| hkc(nn/dd)(a/t/e)cmesv(r/k)ngtydypkyseesklnre(e/k)idgvk (SEQ ID NO. 138) | 1918, 30, 35, 77, 80, 98 |
| hkc(nn/dd)(a/t/e)cmesv(r/k)ngtydypkyseesk (SEQ ID NO. 139) | 1918, 30, 35, 77, 80, 98 |
| hqn(e/g)qgsgyaadqkstqnai(d/n)gitnkvnsviekmntqftavgkefnklek (SEQ ID NO. 140) | 1918, 28, 30, 31, 35, 59, 79, 95 |
| hqn(e/g)qgsgyaadqkstqnai(d/n)gitnkvnsviek (SEQ ID NO. 141) | 1918, 28, 30, 31, 35, 59, 79, 95 |
| hqn(e/g)qgsgyaadqkstqnai(d/n)gitnk (SEQ ID NO. 142) | 1918, 28, 30, 31, 35, 59, 79, 95 |
| kfeifpktsswpnh (SEQ ID NO. 143) | 1918, 77 |
| kg(n/s/t)sypkl(n/s)ksy(v/t)nnkgkevlvlwgvh (SEQ ID NO. 144) | 1918, 35, 77, 96 |

TABLE 4-continued

H1N1 Replikin Sequences present in H1N1 hemagglutinins of Influenza viruses in each year for which amino acid sequences were available (1918-2000)

| H1N1 Replikin<br>H1N1 Strain | Year Detected in Influenza<br>(Peak in FIG. 7: P1 E1 E1.1, 1.2, 1.3 E1.4) |
|---|---|
| ksy(v/t)nnkgkevlvlwgvh<br>(SEQ ID NO. 145) | <u>1918</u>, 35, <u>77</u>, <u>96</u> |
| hkcnnecmesvkngtydypkyseesklnrekidgvk<br>(SEQ ID NO. 146) | 1928, <u>31</u>, 95 |
| hkcnnecmesvkngtydypkyseesk<br>(SEQ ID NO. 147) | 1928, <u>31</u>, 95 |
| hkcnnecmesvkngtydypk<br>(SEQ ID NO. 148) | 1928, <u>31</u>, 95 |
| hkcnnecmesvk<br>(SEQ ID NO. 149) | 1928, <u>31</u>, 95 |
| hngkssfy(k/r)nllwlt(e/g)knglypnlsksyvnnkek<br>(SEQ ID NO. 150) | 1928, 95, 00 |
| hngkssfy(k/r)nllwlt(e/g)knglypnsksyvnnk<br>(SEQ ID NO. 151) | 1928, <u>31</u>, 95, 00 |
| hngkssfy(k/r)nllwlt(e/g)knglypnlsk<br>(SEQ ID NO. 152) | 1928, <u>31</u>, 95, 00 |
| hngkssfy(k/r)nllwlt(e/g)k<br>(SEQ ID NO. 153) | 1928, <u>31</u>, 95, 00 |
| kssfyknllwlteknglypnlsksyvnnkekevlvlwgvh<br>(SEQ ID NO. 154) | 1928, <u>31</u>, 95 |
| knllwlteknglypnlsksyvnnkekevlvlwgvh<br>(SEQ ID NO. 155) | 1928, <u>31</u>, 95 |
| knglypnlsksyvnnkekevlvlwgvh<br>(SEQ ID NO. 156) | 1928, <u>31</u>, 95, <u>96</u>, 00 |
| ksy(v/a)nnkekev(l/-)(v/-)lwgvh<br>(SEQ ID NO. 157) | 1928, <u>31</u>, 51, 95, <u>96</u>, 98, 00 |
| kesswpnhtvtk<br>(SEQ ID NO. 158) | 1928, <u>31</u>, 95 |
| het(t/n)kgvtaacpyagassfyrnllwlvkkensypklsksyvnnk<br>(SEQ ID NO. 159) | 1930, 35 |
| het(t/n)kgvtaacpyagassfyrnllwlvkkensypklsk<br>(SEQ ID NO. 160) | 1930, 35 |
| kfeifpktsswpnevlvlwgvh<br>(SEQ ID NO. 161) | 1930 |
| kerswpkh<br>(SEQ ID NO. 162) | 1947, 51, 52, 55, 56, <u>79</u>, 82 |
| klsksyvnnkekevlvlwqvh<br>(SEQ ID NO. 163) | 1947, 51 |
| knnkekevlvlwqvh<br>(SEQ ID NO. 164) | 1947 |
| h(k/n)(g/q)kssfy(r/k)nllwltekng(l/s)yp(n/t)lsksyannkek<br>(SEQ ID NO. 165) | 1948 <u>79</u>, 89, <u>96</u> |
| h(k/n)(g/q)kssfy(r/k)nllwltek<br>(SEQ ID NO. 166) | 1948 <u>79</u>, 89, <u>96</u> |
| hakkssfyk<br>(SEQ ID NO. 167) | <u>1951</u>, 57, 59 |
| hngklcrlkgk<br>(SEQ ID NO. 168) | <u>1951</u>, 52, 55, 56, 57, 59, <u>79</u>, |

TABLE 4-continued

H1N1 Replikin Sequences present in H1N1 hemagglutinins of Influenza viruses in each year for which amino acid sequences were available (1918-2000)

| H1N1 Replikin H1N1 Strain | Year Detected in Influenza (Peak in FIG. 7: P1 E1 E1.1, 1.2, 1.3 E1.4) |
|---|---|
| hyklnn(q/g)kk (SEQ ID NO. 169) | 1956, 00 |
| hdiyrdeainnrfqiqgvkltqgyk (SEQ ID NO. 170) | 1956 |
| kgngcfeifhk (SEQ ID NO. 171) | 1956 |
| klnrliektndkyhqiek (SEQ ID NO. 172) | 1956 |
| klnrliektndkyh (SEQ ID NO. 173) | 1956 |
| kchtdkgslsttk (SEQ ID NO. 174) | 1956 |
| kinngdyaklyiwgvh (SEQ ID NO. 175) | 1956 |
| hngklcrkgiaplqlgk (SEQ ID NO. 176) | 1959, 82 |
| hetnrqvtaacpyagansffrnliwlvkkessypklsk (SEQ ID NO. 177) | <u>1963</u>, 81 |
| hetnrqvtaacpyagansffrnliwlvkkessypk (SEQ ID NO. 178) | <u>1963</u>, 81 |
| hpptstdqqslyqnadayifvgsskynrkfk (SEQ ID NO. 179) | <u>1963</u>, 81 |
| hpptstdqqslyqnadayifvgsskynrkfkpeia (SEQ ID NO. 180) | <u>1963</u>, 81 |
| hdiyrdeainnrfqiqgvkitqgyk (SEQ ID NO. 181) | <u>1977</u>, <u>79</u>, 91 |
| hqneqgsgyaadqkstqnaidgitnkvnsviekmntqftavgk (SEQ ID NO. 182) | <u>1977</u> |
| hqneqgsgyaadqkstqnaidgitnkvnsviek (SEQ ID NO. 183) | <u>1977</u> |
| hqneqgsgyaadqkstqnaingitnkvnsviekmntqftavgkefnklek (SEQ ID NO. 184) | <u>1979</u>, 91 |
| hngklcrlkgiaplqlgk (SEQ ID NO. 185) | <u>1979</u> |
| hkcnnecmesvk (SEQ ID NO. 186) | <u>1979</u> |
| kfeifpkasswpnh (SEQ ID NO. 187) | 1981 |
| hdsnvknlyekvrsqlrnnak (SEQ ID .NO. 188) | 1981 |
| kvnsvikkmntqfaavgkefnh (SEQ ID NO. 189) | 1981 |
| khngklck (SEQ ID NO. 190) | 1981 |
| kkgtsypklsksythnkgkevlvlwgvh (SEQ ID NO. 191) | 1981 |
| kgtsypklsksythnkgkevlvlwgvh (SEQ ID NO. 192) | 1981 |

TABLE 4-continued

H1N1 Replikin Sequences present in H1N1 hemagglutinins of Influenza viruses in each year for which amino acid sequences were available (1918-2000)

| H1N1 Replikin<br>H1N1 Strain | Year Detected in Influenza<br>(Peak in FIG. 7: P1 E1 E1.1, 1.2, 1.3 E1.4) |
|---|---|
| klsksythnkgkevlvlwgvh<br>(SEQ ID NO. 193) | 1981 |
| ksythnkgkevlvlwgvh<br>(SEQ ID NO. 194) | 1981 |
| kgvtascshk<br>(SEQ ID NO. 195) | 1985, 87 |
| kgvtascshkgrssfyrnllwlteknglypnlsk<br>(SEQ ID NO. 196) | 1985, 87 |
| kgnsypklsksyvnnkekevlvlwgih<br>(SEQ ID NO. 197) | 1988 |
| kefnhlek<br>(SEQ ID NO. 198) | 1988 |
| hpptstdqqslyqnadayvfvgssynkkfkpeiatrpk<br>(SEQ ID NO. 199) | 1988 |
| hpptstdqqslyqnadayvfvgssynkkfk<br>(SEQ ID NO. 200) | 1988 |
| hegkssfyrnllwltekegsypklknsyvnk<br>(SEQ ID NO. 201) | 1991 |
| hegkssfyrnllwitekegsypk<br>(SEQ ID NO. 202) | 1991 |
| hkcdnecmesvrngtydypkyseesk<br>(SEQ ID NO. 203) | 1991 |
| kesswpnhtvtk<br>(SEQ ID NO. 204) | 1991, 92 |
| knllwlteknglypnlsksyvnnkekeilvlwgvh<br>(SEQ ID NO. 205) | 1991, 92, <u>96</u> |
| hngkssfy(k/m)(n/-)llwlt(e/g)(-/k)knglypnlsk<br>(SEQ ID NO. 206) | 1991, 92, <u>96</u>, 00 |
| hngkssfyknllwltek<br>(SEQ ID NO. 207) | 1991, 92, <u>96</u> |
| htvtkgvtascshngkssfyknllwlteknglypnlsksyvnnkekevlvlwgvh<br>(SEQ ID NO. 208) | 1995 |
| htvt(k/g)gv(t/s)ascshngkssfy(k/m)(n/-)llwlt(e/g)k(-n/k)glypnlsk<br>(SEQ ID NO. 209) | 1995, 00 |
| htvtkgvtascshngkssfyknllwltek<br>(SEQ ID NO. 210) | 1995 |
| kyvrstklrmvtglrnipsiqsrglfgaiagfieggwtgmidgwygyh<br>(SEQ ID NO. 211) | 1995 |
| hqneqgsgyaadkstqnaingitnkvnsiiekmntqftavgk<br>(SEQ ID NO. 212) | 1995 |
| hqneqgsgyaadkstqnaingitnkvnsiiek<br>(SEQ ID NO. 213) | 1995 |
| hqneqgsgyaadkstqnaingitnk<br>(SEQ ID NO. 214) | 1995 |
| hsgarsfyrnllwivkkgnsypk<br>(SEQ ID NO. 215) | <u>1996</u> |
| hsgarsfyrnllwivkkgnsypklnk<br>(SEQ ID NO. 216) | <u>1996</u> |

TABLE 4-continued

H1N1 Replikin Sequences present in H1N1 hemagglutinins of Influenza viruses in each year for which amino acid sequences were available (1918-2000)

| H1N1 Replikin<br>H1N1 Strain | Year Detected in Influenza<br>(Peak in FIG. 7: P1 E1 E1.1, 1.2, 1.3 E1.4) |
|---|---|
| hsgarsfyrnllwivkkgnsypklnksytndk<br>(SEQ ID NO. 217) | <u>1996</u> |
| hsgarsfyrnllwivkkgnsypklnksytndkgk<br>(SEQ ID NO. 218) | <u>1996</u> |
| htvskgvttscshngk<br>(SEQ ID NO. 219) | <u>1996</u> |
| katswpnhettk<br>(SEQ ID NO. 220) | <u>1996</u> |
| kqvttscshnqk<br>(SEQ ID NO. 221) | <u>1996</u> |
| kgnsypklnksytndkgkevlviwgvh<br>(SEQ ID NO. 222) | <u>1996</u> |
| klnksytndkgkevlviwgvh<br>(SEQ ID NO. 223) | <u>1996</u> |
| ksytndkgkevlviwgvh<br>(SEQ ID NO. 224) | <u>1996</u> |
| hnqkssfyrnllwlt(e/q)knglypnlsksy(v/a)annkek<br>(SEQ ID NO. 225) | 1997, 98, 99 |
| hpitigecpkyvrsak<br>(SEQ ID NO. 226) | 1997 |
| hqneqgsgyaadqkstqnaingitnkvnsviekmntqftavgk<br>(SEQ ID NO. 227) | 1998 |
| hqneqgsgyaadqkstqnaingitnkvnsviek<br>(SEQ ID NO. 228) | 1998 |
| hngkssfyrnllwlteknglypnlsksyvnnkek<br>(SEQ ID NO. 229) | 1998 |

1. Influenza H1N1 was responsible for the human pandemic (global distribution) of 1918.
2. Abbreviation for years: eg. "96" = 1996.
3. The first year that a given replikin appears is indicated at the beginning of the series of years in which that replikin has been found in this work.
4. Overlapping replikin sequences are listed separately.
5. Increase in number of new replikin structures occurs in years of epidemics (underlined): eg. 1918 and 1977 and correlates with increased total replikin concentration (number of replikins per 100 amino acid residues). See FIG. 7.

TABLE 5

Replikin Sequences present in hemagglutinins of Influenza H2N2 viruses in years 1957-2000

Figure 8:
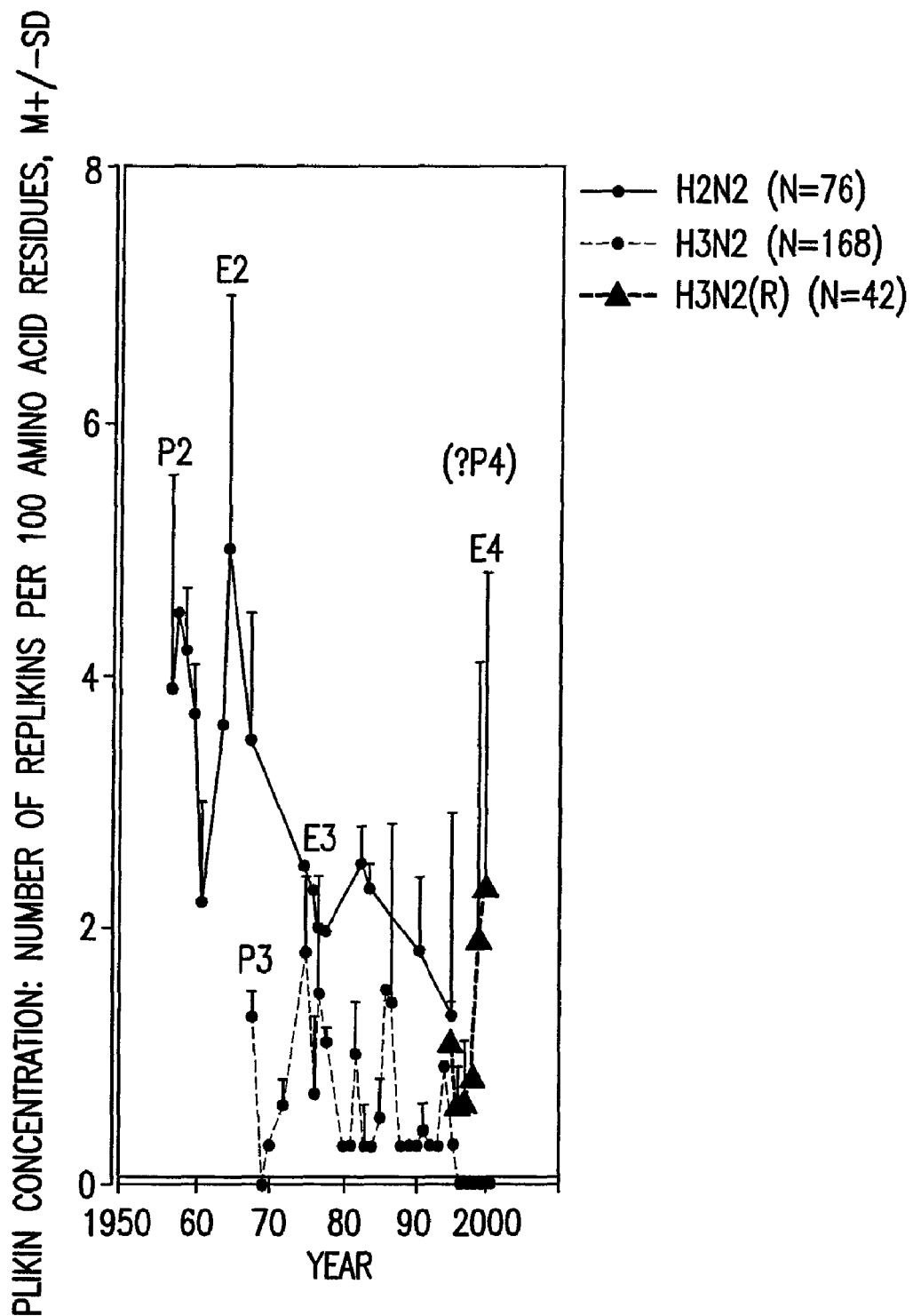
FIG. 8 is a graph of the replikin concentration observed in hemagglutinin of influenza A strains, H2N2 and H3N2, as well as an emerging strain defined by its constituent Replikins, designated H3N2(R), on a year by year basis from 1950 to 2001.

| Influenza H2N2 Replikins | Year Detected in Influenza H2N2 strain<br>(Peak in FIG. 8: P2 E2) |
|---|---|
| khfekvkilpk<br>(SEQ ID NO. 230) | <u>1957</u>, 58, 59, 60, 61, 64, <u>65</u>, 68, 78, 83, 84, 91 |
| khllssvkhfekvk<br>(SEQ ID NO. 231) | <u>1957</u>, 58, 59, 60, 61, 83, 84, 91 |
| ha(k/q/m)(d/n)ilekthngk<br>(SEQ ID NO. 232) | <u>1957</u>, 58, 59, 60, 61, 64, <u>65</u>, 68, 78, 83, 84, 91, 95 |
| ha(k/q/m)(d/n)ilekthngklc(k/r)<br>(SEQ ID NO. 233) | <u>1957</u>, 58, 59, 60, 61, 64, <u>65</u>, 68, 78, 83, 84, 91, 95 |
| hnvhpltigecpkyvksek<br>(SEQ ID NO. 234) | <u>1957</u>, 58, 59, <u>65</u>, 68 |

TABLE 5-continued

Replikin Sequences present in hemagglutinins of Influenza H2N2 viruses in years 1957-2000

| Influenza H2N2 Replikins | Year Detected in Influenza H2N2 strain (Peak in FIG. 8: P2 E2) |
|---|---|
| hpltigecpkyvksek (SEQ ID NO. 235) | <u>1957</u>, 58, 59, <u>65</u>, 68, 64, 65, 68, 78, 83, 84, 91 |
| khllssvkhfekvkilpk (SEQ ID NO. 236) | <u>1957</u>, 58, 59, 60, 61, 64, <u>65</u>, 68, 78 |
| krqssgimktegtlencetkcqtplgainttlpfhnvh (SEQ ID NO. 237) | <u>1957</u>, 59, 83 |
| kgsnyp(v/i)ak(g/r)synntsgeqmliiwq(v/i)h (SEQ ID NO. 238) | <u>1957</u>, 58, 59, 61, 83, 91, 95 |
| httlgqsracavsgnpsffrnmvwltekgsnypvak (SEQ ID NO. 239) | <u>1957</u> |
| khfekvk (SEQ ID NO. 240) | <u>1957</u>, 59, <u>65</u> |
| kiskrgssgimktegtlencetkcqtplgainttlpfh (SEQ ID NO. 241) | <u>1957</u>, 59, <u>65</u>, 91 |
| krgssgimktegtlencetkcqtplgainttlpfh (SEQ ID NO. 242) | <u>1957</u>, 59, <u>65</u>, 91 |
| ktegtlencetkcqtplgainttlpfh (SEQ ID NO. 243) | <u>1957</u>, 59, <u>65</u>, 91 |
| kiskrgssgimktegtlencetkcqtplgainttlpfh (SEQ ID NO. 244) | <u>1957</u>, 59, <u>65</u>, 91 |
| ktegtlencetkcqtplgainttlpfhn(v/i)h (SEQ ID NO. 245) | <u>1957</u>, 59, <u>65</u>, 91 |
| kiskrgssgimktegtlencetkcqtplgainttlpfh (SEQ ID NO. 246) | <u>1957</u>, 59, <u>65</u>, 91 |
| k(e/g)snypvakgsynntsgeqmliiwgvh (SEQ ID NO. 247) | <u>1957</u>, 60, <u>65</u> |
| hpltigecpkyvksek (SEQ ID NO. 248) | <u>1957</u>, 60, <u>65</u> |
| kcqtplgaikttlpfh (SEQ ID NO. 249) | <u>1957</u>, <u>65</u> |
| hhsndqgsgyaadkestqka(f/i)dgitnkvnsviek mntqfeavgklf(n/s)nleklenlnkk (SEQ ID NO. 250) | 1961, <u>65</u>, 68, 83, 84 |
| hsndqgsgyaadkestqka(f/i)dgitnkvnsviek mntqfeavgklf(n/s)nleklenlnkk (SEQ ID NO. 251) | 1961, <u>65</u>, 68, 83, 84 |
| hsndqgsgyaadkestqka(f/i)dgitnk (SEQ ID NO. 252) | 1961, <u>65</u>, 68, 83, 84 |
| hdsnvrnlydkvrmqlrdnak (SEQ ID NO. 253) | 1964, 68, 76, 84, 91 |
| hkcddecmnsvkngtydypklnrneikgvk (SEQ ID NO. 254) | 1964, <u>65</u>, 68, 76, 83, 84, 91 |
| hkcddecmnsvkngtydypklnmeik (SEQ ID NO. 255) | 1964, <u>65</u>, 68, 76, 83, 84, 91 |
| hkcddecmnsvkngtydypk (SEQ ID NO. 256) | 1964, <u>65</u>, 68, 76, 83, 84, 91 |
| hkcddecmnsvk (SEQ ID NO. 257) | 1964, <u>65</u>, 68, 76, 83, 84, 91 |
| kgsnypvakgsynntngeqiliiwgvh (SEQ ID NO. 258) | 1976, 78 |

TABLE 5-continued

Replikin Sequences present in hemagglutinins of Influenza H2N2 viruses in years 1957-2000

| Influenza H2N2 Replikins | Year Detected in Influenza H2N2 strain (Peak in FIG. 8: P2 E2) |
|---|---|
| hsndqgsgyaadkestqkavdgitnkvnsviekmntqfeavgk (SEQ ID NO. 259) | 1976, 91 |
| krgssgimktegtlencetkcqtplgainttlpfh (SEQ ID NO. 260) | 1976, 78, 83, 84 |
| hpltigecpkyvksek (SEQ ID NO. 261) | 1976 |
| hakdilekthngklck (SEQ ID NO. 262) | 1976 |

1. Influenza H2N2 was responsible for the human pandemic (global distribution) of 1957.
2. Abbreviation for years: eg. "58" = 1958.
3. The first year that a given replikin appears is indicated at the beginning of the series of years in which that replikin has been found in this work.
4. Overlapping replikin sequences are listed separately.
5. Increase in number of new replikin structures occurs in years of epidemics (underlined): eg. 1957 and 1965 and correlates with increased total replikin concentration (number of replikins per 100 amino acid residues). See FIG. 8.

TABLE 6

H3N2 Replikin Sequences present in H3N2 hemagglutinins of Influenza viruses in each year for which amino acid sequences were available (1968-2000)

| Influenza H3N2 Replikins | Year Detected in Influenza H3N2 strain Influenza Replikins (Peak in FIG. 8: P3 E3 E4) |
|---|---|
| hdvyrdealnnrfqikgvelksgyk (SEQ ID NO. 263) | 1968, 72, 75 96, 97, 98 |
| htidltdsemnklfertrk (SEQ ID NO. 264) | 1968 |
| kfhqiek (SEQ ID NO. 265) | 1968, 72, 77 96, 97, 98 |
| ktnekfh(g/q)iek (SEQ ID NO. 266) | 1968 86 98 |
| klnr(v/l)iektnekfh (SEQ ID NO. 267) | 1968, 72, 75, 77 97, 98 |
| hqiekefsevegriqdlekyvedtk (SEQ ID NO. 268) | 1968, 72, 98 |
| kicnnphk (SEQ ID NO. 269) | 1975 |
| klnrvikktnekfh (SEQ ID NO. 270) | 1975 |
| hd(I,v)yrdealnnrfqik(g/q)ve(r/k)s(q/g)yk (SEQ ID NO. 271) | 1975, 76, 77, 86 |
| hqiekefsevegriqdlekyvedtk (SEQ ID NO. 272) | 1975 |
| kyvedtkidlwsynaellvalenqh (SEQ ID NO. 273) | 1975 |
| kyvkqnslklatgmrnvpekqtrglfgaiagfiengwegmidgwygfrh (SEQ ID NO. 274) | 1975 |
| kefsevegriqdlekyvedtkidlwsynaellvalenqh (SEQ ID NO. 275) | 1975 2000 |
| hqn(s/e)(e/q)g(t/s)g(q/y)aad(l/q)k--stq(a/n)a(i/l)d(q/g)I(n/t)(g/n)k(l/v)n(r/s)vi(e/c)k (SEQ ID NO. 276) | 1975 2000 |

TABLE 6-continued

H3N2 Replikin Sequences present in H3N2 hemagglutinins of Influenza viruses in each year for which amino acid sequences were available (1968-2000)

| Influenza H3N2 Replikins | Year Detected in Influenza H3N2 strain Influenza Replikins (Peak in FIG. 8: P3 E3 E4) |
|---|---|
| hcd(g/q)f(q,r)nekwdlf(v,/i)er(s/t)k (SEQ ID NO. 277) | <u>1975</u>, 76, <u>77</u>, 78, 80, 81, 82, 83, 84, 85, 86, 88, 89, 90, 91, 92, 93, 94, 95, 96, 97, 98 |
| htidltdsemnkklfertrk (SEQ ID NO. 278) | <u>1977</u>, |
| ksgstypvlkvtmpnndnfdklyiwgvh (SEQ ID NO. 279) | <u>1977</u> |
| klnwltksgntypvlnvtmpnndnfdklviwgvh (SEQ ID NO. 280) | 1982 |
| htidltdsemnklfektrk (SEQ ID NO. 281) | 1986 |
| klnrliektnekfhqtek (SEQ ID NO. 282) | <u>1987</u> |
| htgkssvmrsdapidfcnsecitpnqsipndkpfqnvnkitygacpk (SEQ ID NO. 283) | 1994 |
| htgkssvmrsdapidfcnsecitpnqsipndkpfqnvnk (SEQ ID NO. 284) | 1994 |
| hpstdsdqtslyvrasgrvtvstkrsqqtvipk (SEQ ID NO. 285) | 1994 |
| kyvedtkidlwsynaellvalenqh (SEQ ID NO. 286) | 1997, 98 |
| klfertrkqlrenaedmgngcfkiyh (SEQ ID NO. 287) | 1998 |
| krrsiksffsrlnwlh (SEQ ID NO. 288) | 1998 |
| hpvtigecpky(v/r)kstk (SEQ ID NO. 289) | 2000 |
| kgnsypklsklsksyiinkkkevlviwgih (SEQ ID NO. 290) | 2000 |
| klsklsks(v/y)iinkkkevlviwgih (SEQ ID NO. 291) | 2000 |
| klsks(v/y)iinkkkevlviwgih (SEQ ID NO. 292) | 2000 |

1. Influenza H3N2 was responsible for the human pandemic (global distribution) of 1968.
2. Abbreviation for years: eg. "77" = 1977.
3. The first year that a given replikin appears is indicated at the beginning of the series of years in which that replikin has been found.
4. Overlapping replikin sequences are listed separately.
5. Increase in number of new replikin structures occurs in years of epidemics (underlined): eg. 1975 and correlates with increased total replikin concentration (number of replikins per 100 amino acid residues): See FIG. 8.

Both the concentration and type, i.e., composition of Replikins observed were found to relate to the occurrence of influenza pandemics and epidemics. The concentration of Replikins in influenza viruses was examined by visually scanning the hemagglutinin amino acid sequences published in the National Library of Medicine "PubMed" data base for influenza strains isolated world wide from human and animal reservoirs year by year over the past century, i.e., 1900 to 2001. These Replikin concentrations (number of Replikins per 100 amino acids, mean+/−SD) were then plotted for each strain.

The concentration of Replikins was found to directly relate to the occurrence of influenza pandemics and epidemics. The concentration of Replikins found in influenza B hemagglutinin and influnza A strain, H1N1, is shown in FIG. 7, and the concentration of Replikins found in the two other common influenza virus A strains, H2N2 and H3N2 is shown in FIG. 8 (H2N2, H3N2). The data in FIG. 8 also demonstrate an emerging new strain of influenza virus as defined by its constituent Replikins (H3N2(R)).

Each influenza A strain has been responsible for one pandemic: in 1918, 1957, and 1968, respectively. The data in FIGS. 7 and 8 show that at least one replikin per 100 amino acids is present in each of the influenza hemagglutinin proteins of all isolates of the four common influenza viruses examined, suggesting a function for Replikins in the maintenance of survival levels of replication. In the 1990s, during the decline of the H3N2 strain there were no Replikins present in many isolates of H3N2, but a high concentration of new replikins appeared in H3N2 isolates, which define the emergence of the H3N2(R) strain.

Several properties of Replikin concentration are seen in FIG. 7 and FIG. 8 to be common to all four influenza virus strains: (1) Concentration is cyclic over the years, with a single cycle of rise and fall occurring over a period of two to thirty years. This rise and fall is consistent with the known waxing and waning of individual influenza virus strain predominance by hemagglutinin and neuraminidase classification. (2) Peak Replikin concentrations of each influenza virus strain previously shown to be responsible for a pandemic were observed to relate specifically and individually to each of the three years of the pandemics. For example, for the pandemic of 1918, where the influenza virus strain, H1N1, was shown to be responsible, a peak concentration of the Replikins in H1N1 independently occurred (P1); for the pandemic of 1957, where H2N2 emerged and was shown to be responsible, a peak concentration of the Replikins in H2N2 occurred (P2); and for the pandemic of 1968, where H3N2 emerged and was shown to be the cause of the pandemic, a peak concentration of the Replikins in H3N2 occurred (P3). (3) In the years immediately following each of the above three pandemics, the specific Replikin concentration decreased markedly, perhaps reflecting the broadly distributed immunity generated in each case. Thus, this post-pandemic decline is specific for H1N1 immediately following the pandemic (P1) for which it was responsible, and is not a general property of all strains at the time. An increase of Replikin concentration in influenza B repeatedly occurred simultaneously with the decrease in Replikin concentration in H1N1, e.g., EB1 in 1951 and EB2 in 1976, both associated with influenza B epidemics having the highest mortality. (Stuart-Harris, et al., Edward Arnold Ltd. (1985). (4) A secondary peak concentration, which exceeded the primary peak increase in concentration, occurred 15 years after each of the three pandemics, and this secondary peak was accompanied by an epidemic: 15 years after the 1918 pandemic in an H1N1 'epidemic' year (E1); eight years after the 1957 pandemic in an H2N2 'epidemic' year (E2); and occurred seven years after the 1968 pandemic in an H3N2 'epidemic' year (E3). These secondary peak concentrations of specific Replikins may reflect recovery of the strain. (5) Peaks of each strain's specific Replikin concentration frequently appear to be associated with declines in Replikin concentration of one or both other strains, suggesting competition between strains for host sites. (6) There is an apparent overall tendency for the Replikin concentration of each strain to decline over a period of 35 years (H2N2) to 60 years (influenza B). This decline cannot be ascribed to the influence of vaccines because it was evident in the case of influenza B from 1901 to 1964, prior to common use of influenza vaccines. In the case of influenza B, Replikin recovery from the decline is seen to occur after 1965, but Replikin concentration declined again between 1997 and 2000 (FIG. 7), and this correlates with the low occurrence of influenza B in recent case isolates. H1N1 Replikin concentration peaked in 1978-1979 (FIG. 7) together with the reappearance and prevalence of the H1N1 strain, and then peaked in 1996 coincident with an H1N1 epidemic. (FIG. 7). H1N1 Replikin concentration also declined between 1997 and 2000, and the presence of H1N1 strains decreased in isolates obtained during these years. For H2N2 Replikins, recovery from a 35 year decline has not occurred (FIG. 8), and this correlates with the absence of H2N2 from recent isolates. For H3N2, the Replikin concentration of many isolates fell to zero during the period from 1996 to 2000, but other H3N2 isolates showed a significant, sharp increase in Replikin concentration. This indicates the emergence of a sub-strain of H3N2, which is designated herein as H3N2(R).

FIGS. 7 and 8 demonstrate that frequently a one to three year stepwise increase is observed before Replikin concentration reaches a peak. This stepwise increase proceeds the occurrence of an epidemic, which occurs concurrently with the Replikin peak. Thus, the stepwise increase in concentration of a particular strain is a signal that that particular strain is the most likely candidate to cause an epidemic or pandemic.

Currently, Replikin concentration in the H3N2(R) strain of influenza virus is increasing (FIG. 8, 1997 to 2000). Three similar previous peak increases in H3N2 Replikin concentration are seen to have occurred in the H3N2-based pandemic of 1968 (FIG. 8), when the strain first emerged, and in the H3N2-based epidemics of 1972 and 1975 (FIG. 8). Each of these pandemic and epidemics was associated with excess mortality. (Ailing, et al., Am J. Epidemiol., 113(1):30-43 (1981). The rapid ascent in concentration of the H3N2(R) subspecies of the H3N2 Replikins in 1997-2000, therefore, statistically represents an early warning of an approaching severe epidemic or pandemic. An H3N2 epidemic occurred in Russia in 2000 (FIG. 8, E4); and the CDC report of December 2001 states that currently, H3N2 is the most frequently isolated strain of influenza virus world wide. (Morbidity and Mortality Weekly Reports (MMWR), Center for Disease Control; 50(48):1084-68 (Dec. 7, 2001).

In each case of influenza virus pandemic or epidemic new Replikins emerge. There has been no observation of two of the same Replikins in a given hemagglutinin in a given isolate. To what degree the emergence of a new Replikin represents mutations versus transfer from another animal or avian pool is unknown. In some cases, each year one or more of the original Replikin structures is conserved, while at the same time, new Replikins emerge. For example, in influenza virus B hemagglutinin, five Replikins were constantly conserved between 1919 and 2001, whereas 26 Replikins came and went during the same period (some recurred after several years absence). The disappearance and re-emergence years later of a particular Replikin structure suggests that the Replikins return from another virus host pool rather than through de novo mutation.

In the case of H1N1 Replikins, the two Replikins present in the P1 peak associated with the 1918 pandemic were not present in the recovery E1 peak of 1933, which contains 12 new Replikins. Constantly conserved Replikins, therefore, are the best choice for vaccines, either alone or in combination. However, even recently appearing Replikins accompanying one year's increase in concentration frequently persist and increase further for an additional one or more years, culminating in a concentration peak and an epidemic, thus providing both an early warning and time to vaccinate with synthetic Replikins (see for example, H1N1 in the early 1990's, FIG. 7).

The data in FIGS. 7 and 8 demonstrate a direct relationship between the presence and concentration of a particular Replikin in influenza protein sequences and the occurrence of pandemics and epidemics of influenza. Thus, analysis of the influenza virus hemagglutinin protein sequence for the presence and concentration of Replikins provides a predictor of influenza pandemics and/or epidemics, as well as a target for influenza vaccine formulation.

Composition of Replikins in Strains of Influenza Virus B: Of a total of 26 Replikins identified in this strain (Table 3), the following ten Replikins are present in every influenza B isolate examined from 1902-2001. Overlapping Replikin sequences are listed separately. Lysines and histidines are in bold type to demonstrate homology consistent with the "3-point recognition."

```
kshfanlk                         (SEQ ID NO. 104)
kshfanlkgtk                      (SEQ ID NO. 105)
kshfanlkgtktrgklcpk              (SEQ ID NO. 106)
hekygglnk                        (SEQ ID NO. 107)
hekygglnksk                      (SEQ ID NO. 108)
hekygglnkskpyytgehak             (SEQ ID NO. 109)
hakaigncpiwvk                    (SEQ ID NO. 110)
hakaigncpiwvktplklangtk          (SEQ ID NO. 111)
hakaigncpiwvktplklangtkyrppak    (SEQ ID NO. 112)
hakaigncpiwvktplklangtkyrppakllk (SEQ ID NO. 113)
```

Tables 3 and 4 indicate that there appears to be much greater stability of the Replikin structures in influenza B hemagglutinins compared with H1N1 Replikins. Influenza B has not been responsible for any pandemic, and it appears not to have an animal or avian reservoirs. (Stuart-Harris et al., Edward Arnold Ltd., London (1985)).

Influenza H1N1 Replikins: Only one replikin "hp(v/i)tigecpkyv(r/k)(s/t)(t/a)k" is present in every H1N1 isolate for which sequences are available from 1918, when the strain first appeared and caused the pandemic of that year, through 2000. (Table 4). ("(v/i)" indicates that the amino acid v or i is present in the same position in different years.) Although H1N1 contains only one persistent replikin, H1N1 appears to be more prolific than influenza B. There are 95 different replikin structures in 82 years on H1N1 versus only 31 different Replikins in 100 years of influenza B isolates (Table 4). An increase in the number of new Replikin structures occurs in years of epidemics (Tables 3, 4, 5 and 6) and correlates with increased total Replikin concentration (FIGS. 7 and 8).

Influenza H2N2 Replikins: Influenza H2N2 was responsible for the human pandemic of 1957. Three of the 20 Replikins identified in that strain for 1957 were conserved in each of the H2N2 isolates available for examination on PubMed until 1995 (Table 5).

```
                                          (SEQ ID NO. 232)
    ha(k/q/m)(d/n)ilekthngk (SEQ ID NO. 233)
    ha(k/q/m)(d/n)ilekthngklc(k/r)

(SEQ ID No. 238)
    kgsnyp(v/i)ak(g/r)synntsgeqmliiwq(v/i)h
```

However, in contrast to H1N1, only 13 additional Replikins have been found in H2N2 beginning in 1961. This paucity of appearance of new Replikins correlates with the decline in the concentration of the H2N2 Replikins and the appearance of H2N2 in isolates over the years. (FIG. 8).

Influenza H3N2 Replikins: Influenza H3N2 was responsible for the human pandemic of 1968. Five Replikins which appeared in 1968 disappeared after 1977, but reappeared in the 1990s (Table 6). The only Replikin structure which persisted for 22 years was hcd(g/q)f(q/r)nekwdlf(v/i)er(s/t)k, which appeared first in 1977 and persisted through 1998. The emergence of twelve new H3N2 replikins in the mid 1990s (Table 6) correlates with the increase in Replikin concentration at the same time (FIG. 8), and with the prevalence of the H3N2 strain in recent isolates together with the concurrent disappearance of all Replikins from some of these isolates (FIG. 8), this suggests the emergence of the new substrain H3N2(R).

FIGS. 1 and 2 show that influenza epidemics and pandemics correlate with the increased concentration of replikins in influenza virus, which is due to the reappearance of at least one replikin from one to 59 years after its disappearance. Also, in the A strain only, there is an emergence of new strain-specific Replikin compositions (Tables 4-6). Increase in Replikin concentration by repetition of individual replikins within a single protein appears not to occur in influenza virus, but is seen in other organisms.

It has been believed that changes in the activity of different influenza strains are related to sequence changes in influenza hemagglutinins, which in turn are the products of substitutions effected by one of two poorly understood processes: i) antigenic drift, thought to be due to the accumulation of a series of point mutations in the hemagglutinin molecule, or ii) antigenic shift, in which the changes are so great that genetic reassortment is postulated to occur between the viruses of human and non-human hosts. First, the present data suggests that the change in activity of different influenza strains, rather than being related to non-specific sequence changes, are based upon, or relate to the increased concentration of strain-specific replikins and strain-specific increases in the replication associated with epidemics. In addition, the data were examined for a possible insight into which sequence changes are due to "drift" or "shift", and which due to conservation, storage in reservoirs, then reappearance. The data show that the epidemic-related increase in replikin concentration is not due to the duplication of existing replikins per hemagglutinin, but is due to the reappearance of at least one replikin composition from 1 to up to 59 years after its disappearance, plus in the A strains only, the emergence of new strain-specific replikin compositions (Tables 3-6). Thus the increase in replikin concentration in the influenza B epidemics of 1951 and 1977 are not associated with the emergence of new replikin compositions in the year of the epidemic but only with the reappearance of replikin compositions which had appeared in previous years then disappeared (Table 3). In contrast, for the A strains, in addition to the reappearance of previously disappeared virus replikins, new compositions appear (e.g. in H1N1 in the year of the epidemic of 1996, in addition to the reappearance of 6 earlier replikins, 10 new compositions emerged). Since the A strains only, not influenza B, have access to non-human animal and avian reservoirs, totally new compositions probably derive from non-human host reservoirs rather than from mutations of existing human replikins which appear to bear no resemblance to the new compositions other than the basic requirements of "3-point recognition" (Tables 2-5). The more prolific nature of H1N1 compared with B, and the fact that pandemics have been produced by the three A strains only, but not by the B strain, both may also be a function of the ability of the human A strains to receive new replikin compositions from non-human viral reservoirs.

Some replikins have appeared in only one year, disappeared, and not reappeared to date (Tables 3-6). Other replikins disappear for from one to up to 81 years, when the identical replikin sequence reappears. Key replikin 'k' and 'h' amino acids, and the spaces between them, are conserved during the constant presence of particular replikins over many years, as shown in Tables 2-6 for the following strain-specific replikins: ten of influenza B, the single replikin of H1N1, and the single replikin of H2N3, as well as for the reappearance of identical replikins after an absence. Despite the marked replacement or substitution activity of other amino acids both inside the replikin structure and outside it in the rest of the hemagglutinin sequences, influenza replikin histidine (h) appears never to be, and lysine (k) is rarely replaced. Examples of this conservation are seen in the H1N1 replikin "hp(v/i)tigecpkyv(r/k)(s/t)(t/a)k," (SEQ ID NO. 135) constant between 1918 and 2000, in the H3N2 replikin "hcd(g/q)f(q,r)nekwdlf(v/i)er(s/t)k" (SEQ ID NO. 277) constant between 1975 and 1998 and in the H3N2 replikin "hqn(s/e)(e/q)g(t/s)g(q/y)aad(l/q)kstq(a/n)a(i/l)d(q/g)l(n/t)(g/n)k, (l/v)-n(r/s)vi(e/c)k" (SEQ ID NO. 276) which first appeared in 1975, disappeared for 25 years, and then reappeared in 2000. While many amino acids were substituted, the basic replikin structure of 2 lysines, 6 to 10 residues apart, one histidine, a minimum of 6% lysine in not more than approximately 50 amino acids, was conserved.

Totally random substitution would not permit the persistence of these H1N1 and H3N2 replikins, nor from 1902 to 2001 in influenza B the persistence of 10 replikin structures, nor the reappearance in 1993 of a 1919 18mer replikin after an absence of 74 years. Rather than a random type of substitution, the constancy suggests an orderly controlled process, or in the least, protection of the key replikin residues so that they are fixed or bound in some way: lysines, perhaps bound to nucleic acids, and histidines, perhaps bound to respiratory redox enzymes. The mechanisms which control this conservation are at present unknown.

Whether the conservation of replikin structures is unique to influenza or occurs in other virus replikins was examined in foot and mouth disease virus (FMDV) isolates, where extensive mutations in proteins of this virus have been well-documented worldwide over decades. In the protein VP1 of FMDV type 0, the replikin "hkqkivapvk" (SEQ ID NO. 3) was found to be conserved in 78% of the 236 isolates reported in PubMed, and each amino acid was found to be conserved in individual isolates as follows: h, 95.6%; k, 91.8%; q, 92.3%; k, 84.1%; i, 90.7%; v, 91.8%; a. 97.3%; p, 96.2%; v, 75.4%; k, 88.4%. Similarly, conservation was observed in different isolates of HIV for its replikins such as "kcfncgkegh" (SEQ ID NO. 5) or "kvylawvpahk" (SEQ ID NO. 6) in HIV Type 1 and "kcwncgkegh" (SEQ ID NO. 7) in HIV Type 2[16]. The high rate of conservation observed in FMVD and HIV replikins suggests that conservation observed in influenza replikins is a general property of viral replikins.

Figure 3:
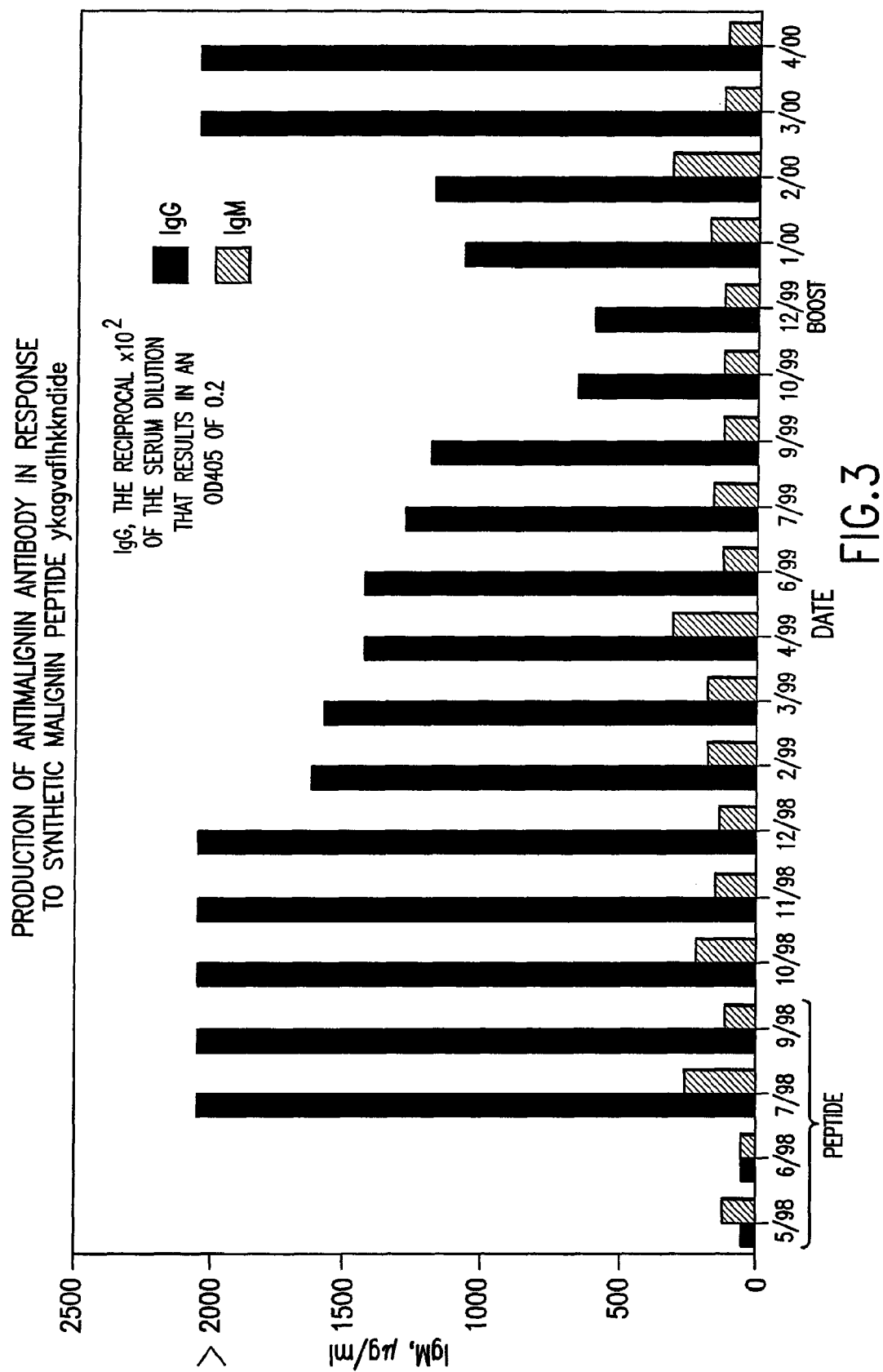
FIG. 3 is a bar graph showing amount of antimalignin antibody produced in response to exposure to the recognin 16-mer.
Figure 4A:
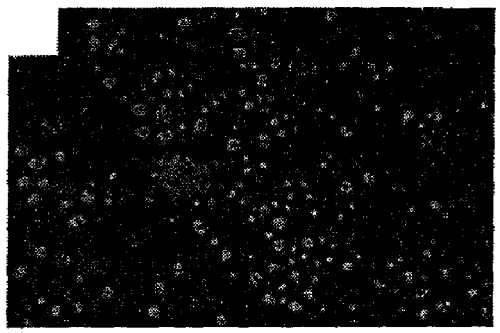
FIG. 4A is a photograph of a blood smear taken with ordinary and fluorescent light.
Figure 4B:
FIG. 4B is a photograph of a blood smear taken with ordinary and fluorescent light illustrating the presence of two leukemic cells.
Figure 4C:
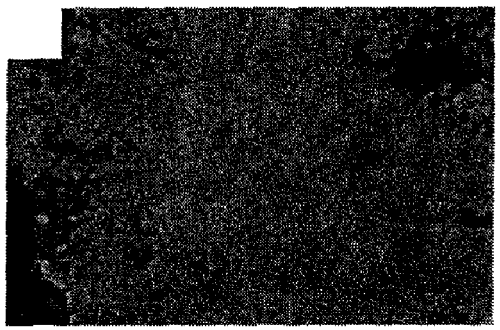
FIG. 4C is a photograph of a dense layer of glioma cells in the presence of antimalignin antibody.
Figure 4D:
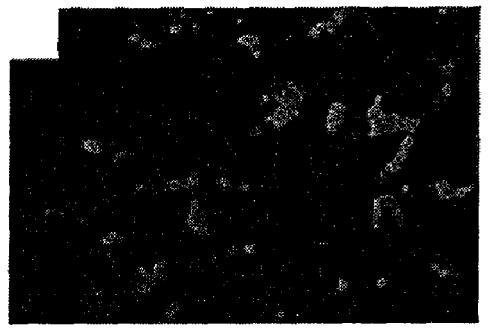
FIG. 4D and FIG. 4E are photographs of the layer of cells in FIG. 4C taken at 30 and 45 minutes following addition of antimalignin antibody.
Figure 4E:
Figure 4F:
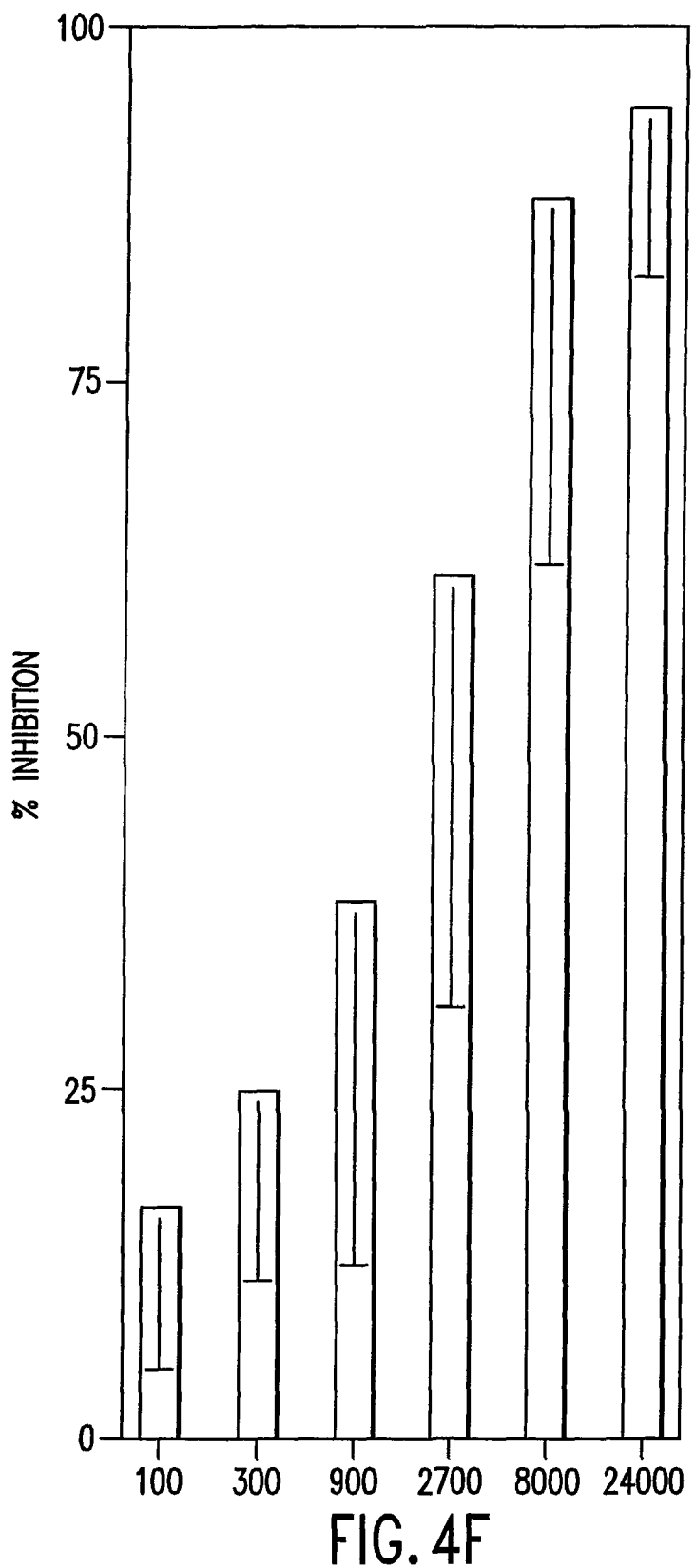
FIG. 4F is a bar graph showing the inhibition of growth of small cell lung carcinoma cells in vitro by antimalignin antibody.

Data on anti-Replikin antibodies also support Replikin class unity. An anti-Replikin antibody response has been quantified by immunoadsorption of serum antimalignin antibody to immobilized malignin (see Methods in U.S. Pat. No. 5,866,690). The abundant production of antimalignin antibody by administration to rabbits of the synthetic version of the 16-mer peptide whose sequence was derived from malignin, absent carbohydrate or other groups, has established rigorously that this peptide alone is an epitope, that is, it is a sufficient basis for this immune response (FIG. 3). The 16-mer peptide produced both IgM and IgG forms of the antibody. Antimalignin antibody was found to be increased in concentration in serum in 37% of 79 cases in the U.S. and Asia of hepatitis B and C, early, in the first five years of infection, long before the usual observance of liver cancer, which develops about fifteen to twenty-five years after infection. Relevant to both infectious hepatitis and HIV infections, transformed cells may be one form of safe haven for the virus: prolonging cell life and avoiding virus eviction, so that the virus remains inaccessible to anti-viral treatment.

Because administration of Replikins stimulates the immune system to produce antibodies having a cytotoxic effect, peptide vaccines based on the particular influenza virus Replikin or group of Replikins observed to be most concentrated over a given time period provide protection against the particular strain of influenza most likely to cause an outbreak in a given influenza season, e.g., an emerging strain or re-emerging strain For example, analysis of the influenza virus hemagglutinin amino acid sequence on a yearly or bi-yearly basis, provides data which are useful in formulating a specifically targeted influenza vaccine for that year. It is understood that such analysis may be conducted on a region-by-region basis or at any desired time period, so that strains emerging in different areas throughout the world can be detected and specifically targeted vaccines for each region can be formulated.

Currently, vaccine formulations are changed twice yearly at international WHO and CDC meetings. Vaccine formulations are based on serological evidence of the most current preponderance of influenza virus strain in a given region of the world. However, prior to the present invention there has been no correlation of influenza virus strain specific amino acid sequence changes with occurrence of influenza epidemics or pandemics.

The observations of specific Replikins and their concentration in influenza virus proteins provides the first specific quantitative early chemical correlates of influenza pandemics and epidemics and provides for production and timely administration of influenza vaccines tailored specifically to treat the prevalent emerging or re-emerging strain of influenza virus in a particular region of the world. By analyzing the protein sequences of isolates of strains of influenza virus, such as the hemagglutinin protein sequence, for the presence, concentration and/or conservation of Replikins, influenza virus pandemics and epidemics can be predicted. Furthermore, the severity of such outbreaks of influenza can be significantly lessened by administering an influenza peptide vaccine based on the Replikin sequences found to be most abundant or shown to be on the rise in virus isolates over a given time period, such as about one to about three years.

An influenza peptide vaccine of the invention may include a single Replikin peptide sequence or may include a plurality of Replikin sequences observed in influenza virus strains. Preferably, the peptide vaccine is based on Replikin sequence(s) shown to be increasing in concentration over a given time period and conserved for at least that period of time. However, a vaccine may include a conserved Replikin peptide(s) in combination with a new Replikin(s) peptide or may be based on new Replikin peptide sequences. The Replikin peptides can be synthesized by any method, including chemical synthesis or recombinant gene technology, and may include non-Replikin sequences, although vaccines based on peptides containing only Replikin sequences are preferred. Preferably, vaccine compositions of the invention also contain a pharmaceutically acceptable carrier and/or adjuvant.

The influenza vaccines of the present invention can be administered alone or in combination with antiviral drugs, such as ganciclovir; interferon; interleukin; M2 inhibitors, such as, amantadine, rimantadine; neuraminidase inhibitors, such as zanamivir and oseltamivir; and the like, as well as with combinations of antiviral drugs.

Analysis of the primary structure of a *Plasmodium farciparum* malaria antigen located at the merozoite surface and/or within the parasitophorous vacuole revealed that this organism, like influenza virus, also contains numerous Replikins. However, there are several differences between the observation of Replikins in *Plasmodium falciparum* and influenza virus isolates. For example, *Plasmodium falciparum* contains several partial Replikins, referred to herein as "Replikin decoys." These decoy structures contain an abundance of lysine residues, but lack the histidine required of Replikin structures. It is believed that the decoy structure maximizes the chances that an anti-malarial antibody or other agent will bind to the relatively less important structure containing the lysines, i.e., the Replikin decoys, rather than binding to histidine, which is present in Replikin structure, such as replikins in respiratory enzymes, which could result in destruction of the trypanosome.

Another difference seen in *Plasmodium falciparum* is a frequent repetition of individual Replikin structures within a single protein, which was not observed with influenza virus. Repetition may occur by (a) sharing of lysine residues between Replikins, and (b) by repetition of a portion of a Replikin sequence within another Replikin sequence.

A third significant difference between Replikin structures observed in influenza virus isolates and *Plasmodium falciparum* is a marked overlapping of Replikin structures throughout malarial proteins, e.g., there are nine overlapping replikins in the 39 amino acid sequence of SEQ ID NO. 393 (Replikin concentration=23.1/100 amino acids); and 15 overlapping replikins in the 41 amino acids of SEQ ID NO. 467 (Replikin concentration=36.6/100 amino acids). Both of these overlapping Replikin structures occur in blood stage trophozoites and schizonts. In contrast, influenza virus Replikins are more scattered throughout the protein and the maximum Replikin concentration is about 7.5/100 amino acids (FIG. 7); and tomato-leaf curl gemini virus, which was also observed to have overlapping replikins has only about 3.1/100 amino acids.

This mechanism of lysine multiples is also seen in the Replikins of cancer proteins such as in gastric cancer transforming protein, ktkkgnrvsptmkvth (SEQ ID NO. 88), and in transforming protein P21B (K-RAS 2B) of lung, khkekmskdgkkkkkks (SEQ ID NO. 89).

The relationship of higher Replikin concentration to rapid replication is also confirmed by analysis of HIV isolates. It was found that the slow-growing low titer strain of HIV (NSI, "Bru", which is prevalent in early stage HIV infection has a Replikin concentration of 1.1 (+/−1.6) Replikins per 100 amino acids, Whereas the rapidly-growing high titer strain of HIV (S1, "Lai"), which is prevalent in late stage HIV infection has a Replikin concentration of 6.8 (+/−2.7) Replikins per 100 amino acid residues.

The high concentration of overlapping Replikins in malaria, influenza virus and cancer cells is consistent with the legendary high and rapid replicating ability of malaria organisms. The multitude of overlapping Replikins in malaria also provides an opportunity for the organism to flood and confuse the immune system of its host and thereby maximize the chance that the wrong antibody will be made and perpetuated, leaving key malaria antigens unharmed.

As in the case of influenza virus, for example, peptide vaccines based on the Replikin structure(s) found in the malaria organism can provide an effective means of preventing and/or treating malaria. Vaccination against malaria can be achieved by administering a composition containing one or a mixture of Replikin structures observed in *Plasmodium falciparum*. Furthermore, antibodies to malaria Replikins can be generated and administered for passive immunity or malaria detection purposes.

Table 7 provides a list of several *Plasmodium falciparum* Replikin sequences. It should be noted that this list is not meant to be complete. Different isolates of the organism may contain other Replikin structures.

TABLE 7

| Malaria replikins | |
|---|---|
| a) Primary structure of a Plasmodium falciparum malaria antigen located at the merozoite surface and within the parasitophorous vacuole<br>a) i) DECOYS:<br>(C-Terminal) | |
| keeeekekekekekeekekeekekeekekekeekekekekeekeeekk,<br>or | (SEQ ID NO. 293) |
| keeeekekekekekeekekeekekeekekekeekekekekeekeeekkek,<br>or | (SEQ ID NO. 294) |
| keeeekekekekekeekekeekekekeekekeekekeekeekeeekk,<br>or | (SEQ ID NO. 295) |
| keeeekekek | (SEQ ID NO. 296) |
| ii) REPLIKINS: | |
| Hkklikalkkniesiqnkk | (SEQ ID NO. 297) |
| hkklikalkkniesiqnkm | (SEQ ID NO. 298) |
| hkklikalkk | (SEQ ID NO. 299) |
| hkklikalk | (SEQ ID NO. 300) |
| katysfvntkkkiislksqghkk | (SEQ ID NO. 301) |
| katysfvntkkkiislksqghk | (SEQ ID NO. 302) |
| katysfvntkkkiislksqgh | (SEQ ID NO. 303) |
| htyvkgkkapsdpqca dikeeckellkek | (SEQ ID NO. 304) |

TABLE 7-continued

| Malaria replikins | |
|---|---|
| kiislksqghk | (SEQ ID NO. 305) |
| kkkkfeplkngnvsetiklih | (SEQ ID NO. 306) |
| kkkfeplkngnvsetiklih | (SEQ ID NO. 307) |
| kkfeplkngnvsetiklih | (SEQ ID NO. 308) |
| kngnvsetiklih | (SEQ ID NO. 309) |
| klihlgnkdkk | (SEQ ID NO. 310) |
| kvkkigvtlkkfeplkngnvsetiklihlgnkdkkh | (SEQ ID NO. 311) |
| hliyknksynplllscvkkmnmlkenvdyiqnqnlfkelmnqkatysfvntkkkiislk | (SEQ ID NO. 312) |
| hliyknksynplllscvkkmnmlkenvdyiqnqnlfkelmnqkatysfvntk | (SEQ ID NO. 313) |
| hliyknksynplllscvkkmnmlkenvdyiqnqnlfkelmnqk | (SEQ ID NO. 314) |
| hliyknksynplllscvkkmnmlkenvdyiqknqnlfk | (SEQ ID NO. 315) |
| hliyknksynplllscvkkmnmlk | (SEQ ID NO. 316) |
| ksannsanngkknnaeemknlvnflqshkklikalkkniesiqnkkh | (SEQ ID NO. 317) |
| kknnaeemknlvnflqshkklikalkkniesiqnkkh | (SEQ ID NO. 318) |
| knlvnflqshkklikalkkniesiqnkkh | (SEQ ID NO. 319) |
| kklikalkkniesiqnkkh | (SEQ ID NO. 320) |
| klikalkkniesiqnkkh | (SEQ ID NO. 321) |
| kkniesiqnkkh | (SEQ ID NO. 322) |
| kniesiqnkkh | (SEQ ID NO. 323) |
| knnaeemknlvnflqsh | (SEQ ID NO. 324) |
| kklikalkkniesiqnkkqghkk | (SEQ ID NO. 325) |
| kknnaeemknlvnflqshk | (SEQ ID NO. 326) |
| knnaeemknlvnflqsh | (SEQ ID NO. 327) |
| klikalkkniesiqnkkqghkk | (SEQ ID NO. 328) |
| kvkkigvtlkkfeplkngnvsetiklih | (SEQ ID NO. 329) |
| kngnvsetiklih | (SEQ ID NO. 330) |
| klihlgnkdkk | (SEQ ID NO. 331) |
| ksannsanngkknnaeemknlvnflqsh | (SEQ ID NO. 332) |
| kknnaeemknlvnflqsh | (SEQ ID NO. 333) |
| kklikalkkniesiqnkkh | (SEQ ID NO. 334) |
| kalkkniesiqnkkh | (SEQ ID NO. 335) |
| kkniesiqnkkh | (SEQ ID NO. 336) |
| kelmnqkatysfvntkkkiislksqgh | (SEQ ID NO. 337) |
| ksqghkk | (SEQ ID NO. 338) |
| kkkiislksqgh | (SEQ ID NO. 339) |
| kkiislksqgh | (SEQ ID NO. 340) |
| kkniesiqnkkh | (SEQ ID NO. 341) |
| kniesiqnkkh | (SEQ ID NO. 342) |

TABLE 7-continued

Malaria replikins

| | |
|---|---|
| htyvkgkkapsdpqcadikeeckellkek | (SEQ ID NO. 343) |
| htyvkgkkapsdpqcadlkeeckellk | (SEQ ID NO. 344) | b) "liver stage antigen-3" gene = "LSA-3" Replikins

| | |
|---|---|
| henvlsaalentqseeekkevidVieevk | (SEQ ID NO. 345) |
| kenvvttilekveettaesvttfsnileeiqentitndtieekleelh | (SEQ ID NO. 346) |
| hylqqmkekfskek | (SEQ ID NO. 347) |
| hylqqmkekfskeknnnvievtnkaekkgnvqvtnktekttk | (SEQ ID NO. 348) |
| hylqqmkekfskeknnnvievtnkaekkgnvqvtnktekttkvdknnk | (SEQ ID NO. 349) |
| hylqqmkekfskeknnnvievtnkaekkgnvqvtnktekttkvdknnkvpkkrrtqk | (SEQ ID NO. 350) |
| hylqqmkekfskeknnnvievtnkaekkgnvqvtnktekttkvdknnkvpkkrrtqksk | (SEQ ID NO. 351) |
| hvdevmkyvqkidkevdkevskaleskndvtnvlkqnqdffskvknfvkkyk | (SEQ ID NO. 352) |
| hvdevmkyvqkidkevdkevskaleskndvtnvlkqnqdffskvknfvkk | (SEQ ID NO. 353) |
| hvdevmkyvqkidkevdkevskaleskndvtnvlkqnqdffsk | (SEQ ID NO. 354) |
| hvdevmkyvqkidkeVdkevskaleskndvtnvlk | (SEQ ID NO. 355) |
| hvdevmkyvqkidkevdkevskalesk | (SEQ ID NO. 356) |
| hvdevmkyvqkidkevdkevsk | (SEQ ID NO. 357) |
| hvdevmkyvqkidkevdk | (SEQ ID NO. 358) |
| hvdevmkyvqkidk | (SEQ ID NO. 359) |
| kdevidlivqkekriekvkakkkklekkveegvsglkkh | (SEQ ID NO. 360) |
| kvkakkkklekkveegvsglkkh | (SEQ ID NO. 361) |
| kakkkklekkveegvsglkkh | (SEQ ID NO. 362) |
| kkkkekkveegvsglkkh | (SEQ ID NO. 363) |
| kkklekkveegvsglkkh | (SEQ ID NO. 364) |
| kklekkveegvsglkkh | (SEQ ID NO. 365) |
| klekkveegvsglkkh | (SEQ ID NO. 366) |
| kkveegvsglkkh | (SEQ ID NO. 367) |
| kveegvsglkkh | (SEQ ID NO. 368) |
| hveqnvyvdvdvpamkdqflgilneagglkemffnledvfksesdvitveeikdepvqk | (SEQ ID NO. 369) |
| hikgleeddleevddlkgsildmlkgdmelgdmdkesledvttklgerveslk | (SEQ ID NO. 370) |
| hikgleeddleevddlkgsildmlkgdmelgdmdkesledvttk | (SEQ ID NO. 371) |
| hikgleeddleevddlkgsildmlkgdmelgdmdk | (SEQ ID NO. 372) |
| hikgleeddleevddlkgsildmlk | (SEQ ID NO. 373) |
| hiisgdadvlssalgmdeeqmktrkkaqrpk | (SEQ ID NO. 374) |
| hditttldevvelkdveedkiek | (SEQ ID NO. 375) |
| kkleevhelk | (SEQ ID NO. 376) |
| kleevhelk | (SEQ ID NO. 377) |
| ktietdileekkeiekdh | (SEQ ID NO. 378) |
| kkeiekdhfek | (SEQ ID NO. 379) |

TABLE 7-continued

| Malaria replikins | |
|---|---|
| kdhfek | (SEQ ID NO. 380) |
| kfeeeaeeikh | (SEQ ID NO. 381) |
| c) 28 KDA ookinete surface antigen precursor Replikins: | |
| kdgdtkctlecaqgkkcikhksdhnhksdhnhksdpnhkkknnnnnk | (SEQ ID NO. 382) |
| kdgdtkctlecaqgkkcikhksdhnhksdlnhksdpnhkk | (SEQ ID NO. 383) |
| kdgdtkctlecaqgkkcikhksdhnhksdhnhksdpnhk | (SEQ ID NO. 384) |
| kdgdtkctlecaqgkkcikhksdhnhksdhnhk | (SEQ ID NO. 385) |
| kdgdtkctlecaqgkkcikhksdhnhk | (SEQ ID NO. 386) |
| kdgdtkctlecaqgkkcikhk | (SEQ ID NO. 387) |
| kdgdtkctlecaqgkk | (SEQ ID NO. 388) |
| kdgdtkctlecaqgk | (SEQ ID NO. 389) |
| kciqaecnykecgeqkcvwdgih | (SEQ ID NO. 390) |
| kecgeqkcvwdgih | (SEQ ID NO. 391) |
| hieckcnndyvltnryecepknkctsledtnk | (SEQ ID NO. 392) |
| d) Blood stage trophozoites and schizonts Replikins: | |
| ksdhnhksdhnhksdhnhksdhnhksdpnhkkknnnnnk | (SEQ ID NO. 393) |
| ksdhnhksdhnhksdhnhksdpnhkkknnnnnk | (SEQ ID NO. 394) |
| ksdhnhksdbnhksdpnhkkknnnnnk | (SEQ ID NO. 395) |
| ksdhnhksdpnhkkknnnnnk | (SEQ ID NO. 396) |
| kkknnnnnkdnksdpnhk | (SEQ ID NO. 397) |
| kknnnnnkdnksdpnhk | (SEQ ID NO. 398) |
| knnnnnkdnksdpnhk | (SEQ ID NO. 399) |
| kdnksdpnhk | (SEQ ID NO. 400) |
| ksdpnhk | (SEQ ID NO. 401) |
| hslyalqqneeyqkvknekdqneikkikqlieknk | (SEQ ID NO. 402) |
| hslyalqqneeyqkvknekdqneikkik | (SEQ ID NO. 403) |
| hslyalqqneeyqkvknekdqneikk | (SEQ ID NO. 404) |
| hslyalqqneeyqkvknekdqneik | (SEQ ID NO. 405) |
| hklenleemdk | (SEQ ID NO. 406) |
| khfddntneqk | (SEQ ID NO. 407) |
| kkeddekh | (SEQ ID NO. 408) |
| keennkkeddekh | (SEQ ID NO. 409) |
| ktsssgilnkeennkkeddekh | (SEQ ID NO. 410) |
| knihikk | (SEQ ID NO. 411) |
| hikkkegidigyk | (SEQ ID NO. 412) |
| kkmwtcklwdnkgneitknih | (SEQ ID NO. 413) |
| kkgiqwnllkkmwtcklwdnkgneitknih | (SEQ ID NO. 414) |
| kekkdsnenrkkkqkedkknpnklkkieytnkithffkaknnkqqnnvth | (SEQ ID NO. 415) |
| kkdsnenrkkkqkedkknpnklkkieytnkithffkaknnkqqnnvth | (SEQ ID NO. 416) |

TABLE 7-continued

| Malaria replikins | |
|---|---|
| kdsnenrkkkqkedkknpnklkkieytnkithffkaknnkqqnnvth | (SEQ ID NO. 417) |
| kkqkedkknpnklkkieytnkithffkaknnkqqnnvth | (SEQ ID NO. 418) |
| kqkedkknpnklkkieytnkithffkaknnkqqnnvth | (SEQ ID NO. 419) |
| kedkknpnklkkieytnkithffkaknnkqqnnvth | (SEQ ID NO. 420) |
| knpnklkkieytnkithffkaknnkqqnnvth | (SEQ ID NO. 421) |
| kkieytnkithffkaknnkqqnnvth | (SEQ ID NO. 422) |
| kieytnkithffkaknnkqqnnvth | (SEQ ID NO. 423) |
| kithffkaknnkqqnnvth | (SEQ ID NO. 424) |
| hknnediknndnskdikndnskdikndnskdikndnnedikndnskdik | (SEQ ID NO. 425) |
| hknedikndnskdikndnskdikndnskdikndnnedikndnsk | (SEQ ID NO. 426) |
| hknnedikndnskdikndnskdikndnskdikndnnedik | (SEQ ID NO. 427) |
| hknnedikndnskdikndnskdikndnskdik | (SEQ ID NO. 428) |
| hknnedikndnskdikndnskdikndnsk | (SEQ ID NO. 429) |
| hknnedikndnskdikndnskdik | (SEQ ID NO. 430) |
| hknnedikndnskdikndnsk | (SEQ ID NO. 431) |
| hknnedikndnskdik | (SEQ ID NO. 432) |
| hknnedik | (SEQ ID NO. 433) |
| kkyddlqnkynilnklknsleekneelkkyh | (SEQ ID NO. 434) |
| kyddlqnkynilnklknsleekneelkkyh | (SEQ ID NO. 435) |
| kynilnklknsleekneelkkyh | (SEQ ID NO. 436) |
| klknsleekneelkkyh | (SEQ ID NO. 437) |
| knsleekneelkkyh | (SEQ ID NO. 438) |
| kneelkkyh | (SEQ ID NO. 439) |
| hmgnnqdinenvynikpqefkeeeeedismvntkk | (SEQ ID NO. 440) |
| knsnelkrindnffklh | (SEQ ID NO. 441) |
| kpclykkckisqclykkckisqvwwcmpvkdtfntyernnvlnskienniekiph | (SEQ ID NO. 442) |
| hinneytnknpkncllykneernyndnnikdyinsmnfkk | (SEQ ID NO. 443) |
| hinneytnknpkncllykneernyndnnikdyinsmnfk | (SEQ ID NO. 444) |
| hinneytnknpkncllyk | (SEQ ID NO. 445) |
| knktnqskgvkgeyekkketngh | (SEQ ID NO. 446) |
| ktnqskgvkgeyekkketngh | (SEQ ID NO. 447) |
| kgvkgeyekkketngh | (SEQ ID NO. 448) |
| kgeyekkketngh | (SEQ ID NO. 449) |
| ksgmytnegnkscecsykkkssssnkvh | (SEQ ID NO. 450) |
| kscecsykkkssssnkvh | (SEQ ID NO. 451) |
| kkkssssnkvh | (SEQ ID NO. 452) |
| kkssssnkvh | (SEQ ID NO. 453) |
| kssssnkvh | (SEQ ID NO. 454) |

TABLE 7-continued

| Malaria replikins | |
|---|---|
| himlksgmytnegnkscecsykkkssssnk | (SEQ ID NO. 455) |
| himlksgmytnegnkscecsykkk | (SEQ ID NO. 456) |
| himlksgmytnegnkscecsykk | (SEQ ID NO. 457) |
| himlksgmytnegnkscecsyk | (SEQ ID NO. 458) |
| kplaklrkrektqinktkyergdviidnteiqkiiirdyhetlnvhkldh | (SEQ ID NO. 459) |
| krektqinktkyergdviidnteiqkiiirdyhetlnvhkldh | (SEQ ID NO. 460) |
| ktqinktkyergdviidnteiqkiiirdyhetlnvhkldh | (SEQ ID NO. 461) |
| kplaklrkrektqinktkyergdviidnteiqkiiirdyhetlnvh | (SEQ ID NO. 462) |
| kplaklrkrektqinktkyergdviidnteiqkiiirdyh | (SEQ ID NO. 463) |
| klrkrektqinktkyergdviidnteiqkiiirdyh | (SEQ ID NO. 464) |
| krektqinktkyergdviidnteiqkiiirdyh | (SEQ ID NO. 465) |
| ktqinktkyergdviidnteiqkiiirdyh | (SEQ ID NO. 466) |
| kkdkekkkdsnenrkkkqkedkknpndnklkkieytnkith | (SEQ ID NO. 467) |
| kdkekkkdsnenrkkkqkedkknpndnklkkieytnkith | (SEQ ID NO. 468) |
| kekkkdsnenrkkkqkedkknpndnklkkieytnkith | (SEQ ID NO. 469) |
| kkkdsnenrkkkqkedkknpndnklkkieytnkith | (SEQ ID NO. 470) |
| kkdsnenrkkkqkedkknpndnklkkieytnkith | (SEQ ID NO. 471) |
| kdsnenrkkkqkedkknpndnklkkieytnkith | (SEQ ID NO. 472) |
| kkkqkedkknpndnklkieytnkith | (SEQ ID NO. 473) |
| kkqkedkknpndnklkkieytnkith | (SEQ ID NO. 474) |
| kqkedkknpndnklkkieytnkith | (SEQ ID NO. 475) |
| kedkknpndnklkkieytnkith | (SEQ ID NO. 476) |
| kknpndnklkkieytnkith | (SEQ ID NO. 477) |
| knpndnklkkieytnkith | (SEQ ID NO. 478) |
| klkkieytnkith | (SEQ ID NO. 479) |
| kkieytnkith | (SEQ ID NO. 480) |
| kieytnkith | (SEQ ID NO. 481) |
| hgqikiedvnnenfnneqmknkyndeekmdiskskslksdflek | (SEQ ID NO. 482) |
| hgqikiedvnnenfnneqmknkyndeekmdiskskslk | (SEQ ID NO. 483) |
| hgqikiedvnnenfnneqmknkyndeekmdisksk | (SEQ ID NO. 484) |
| hgqikiedvnnenfnneqmknkyndeekmdisk | (SEQ ID NO. 485) |
| kkyddlqnkynilnklknsleekneelkkyh | (SEQ ID NO. 486) |
| kyddlqnkynilnklknsleekneelkkyh | (SEQ ID NO. 487) |
| kynilnklknsleekneelkkyh | (SEQ ID NO. 488) |
| klknsleekneelkkyh | (SEQ ID NO. 489) |
| knsleekneelkkyh | (SEQ ID NO. 490) |
| kneelkkyh | (SEQ ID NO. 491) |
| hmgnnqdinenvynikpqefkeeeeedismvntkkcddiqenik | (SEQ ID NO. 492) |
| ktnlyniynnknddkdnildnenreglylcdvmknsnelkrindnffklh | (SEQ ID NO. 493) |

TABLE 7-continued

Malaria replikins

| | |
|---|---|
| knsnelkrindnffklh | (SEQ ID NO. 494) |
| krindnffklh | (SEQ ID NO. 495) |
| hinneytnknpkncllykneernyndnnikdyinsmnfkk | (SEQ ID NO. 496) |
| hinneytnknpkncllykneernyndnnikdyinsmnfk | (SEQ ID NO. 497) |
| hinneytnknpkncllyk | (SEQ ID NO. 498) |
| kpclykkckisqvwwcmpvkdtfntyernnvlnskienniekiph | (SEQ ID NO. 499) |
| kckisqvwwcmpvkdtfntyernnvlnskienniekiph | (SEQ ID NO. 500) |
| kienniekiph | (SEQ ID NO. 501) |
| knktngskgvkgeyekkketngh | (SEQ ID NO. 502) |
| ktngskgvkgeyekkketngh | (SEQ ID NO. 503) |
| kgvkgeyekkketngh | (SEQ ID NO. 504) |
| kgeyekkketngh | (SEQ ID NO. 505) |
| ktiekinkskswffeeldeidkplaklrkrektqinktkyergdviidnteiqkiirdyh | (SEQ ID NO. 506) |
| kinkskswffeeldeidkplaklrkrektqinktkyergdviidnteiqkiirdyh | (SEQ ID NO. 507) |
| kplaklrkrektqinktkyergdviidnteiqkiirdyh | (SEQ ID NO. 508) |
| himlksqmytnegnkscecsykkkssssnkvh | (SEQ ID NO. 509) |
| klrkrektqinktkyergdviidnteiqkiirdyh | (SEQ ID NO. 510) |
| krektqinktkyergdviidnteiqkiirdyh | (SEQ ID NO. 511) |
| ktqinktkyergdviidnteiqkiirdyh | (SEQ ID NO. 512) |
| kplaklrkrektqinktkyergdviidnteiqkiirdyhtlnvhkldh | (SEQ ID NO. 513) |
| klrkrektqinktkyergdviidnteiqkiirdyhtlnvhkldh | (SEQ ID NO. 514) |
| krektqinktkyergdviidnteiqkiirdyhtlnvbkldh | (SEQ ID NO. 515) |
| ktqinktkyergdviidnteiqkiirdyhtlnvhkldh | (SEQ ID NO. 516) |
| kplaklrkrektqinktkyergdviidnteiqkiirdyhtlnvh | (SEQ ID NO. 517) |
| klrkrektqinktkyergdviidnteiqkiirdyhtlnvh | (SEQ ID NO. 518) |
| krektqinktkyergdviidnteiqkiirdyhtlnvh | (SEQ ID NO. 519) |
| ktqinktkyergdviidnteiqkiirdyhtlnvh | (SEQ ID NO. 520) |
| himlksqmytnegnkscecsykkkssssnkvh | (SEQ ID NO. 521) |
| ksqmytnegnkscecsykkksssnkvh | (SEQ ID NO. 522) |
| kscecsykkksssnkvh | (SEQ ID NO. 523) |
| kkksssnkvh | (SEQ ID NO. 524) |
| kksssnkvh | (SEQ ID NO. 525) |
| kssssnkvh | (SEQ ID NO. 526) |
| himlksqmytnegnkscecsykkksssnk | (SEQ ID NO. 527) |
| himlksqmytnegnkscecsykkk | (SEQ ID NO. 528) |
| himlksqmytnegnkscecsykk | (SEQ ID NO. 529) |
| himlksqmytnegnkscecsyk | (SEQ ID NO. 530) |
| hnnhniqiykdkrinfmnphkvmyhdnmsknertek | (SEQ ID NO. 531) |

TABLE 7-continued

Malaria replikins

| | |
|---|---|
| hnnhniqiykdkrinfmnphkvmyhdnmsk | (SEQ ID NO. 532) |
| hnnhniqiykdkrinfmnphk | (SEQ ID NO. 533) |
| hkvmyhdnmsknertek | (SEQ ID NO. 534) |
| hkvmyhdnmsk | (SEQ ID NO. 535) |

Synthetic Replikin vaccines, based on Replikins such as the glioma Replikin (SEQ ID NO.: 1) "kagvaflhkk" or the hepatitis C Replikin (SEQ ID NO.: 18) "hyppkpgcivpak", or HIV Replikins such as (SEQ ID NO.: 5) "kcfncgkegh" or (SEQ ID NO.: 6) "kvylawvpahk" or preferably, an influenza vaccine based on conserved and/or emerging or re-emerging Replikin(s) over a given time period may be used to augment antibody concentration in order to lyse the respective virus infected cells and release virus extracellularly where chemical treatment can then be effective. Similarly, a malaria vaccine, based on Replikins observed in *Plasmodium falciparum* malaria antigens on the merozoite surface or within the parasitophorous vacuole, for example, can be used to generate cytotoxic antibodies to malaria. Recognin and/or Replikin peptides may be administered to a subject to induce the immune system of the subject to produce anti-Replikin antibodies. Generally, a 0.5 to about 2 mg dosage, preferably a 1 mg dosage of each peptide is administered to the subject to induce an immune response. Subsequent dosages may be administered if desired.

In another embodiment of the invention, isolated Replikin peptides may be used to generate antibodies, which may be used, for example to provide passive immunity in an individual. Passive immunity to the strain of influenza identified by the method of the invention to be the most likely cause of future influenza infections may be obtained by administering antibodies to Replikin sequences of the identified strain of influenza virus to patients in need. Similarly, passive immunity to malaria may be obtained by administering antibodies to *Plasmodium falciparum* Replikin(s).

Various procedures known in the art may be used for the production of antibodies to Replikin sequences. Such antibodies include but are not limited to polyclonal, monoclonal, chimeric, humanized, single chain, Fab fragments and fragments produced by an Fab expression library. Antibodies that are linked to a cytotoxic agent may also be generated. Antibodies may also be administered in combination with an antiviral agent. Furthermore, combinations of antibodies to different Replikins may be administered as an antibody cocktail.

For the production of antibodies various host animals may be immunized by injection with a Replikin peptide or a combination of Replikin peptides, including but not limited to rabbits, mice, rats, and larger mammals. Various adjuvants may be used to enhance the immunological response, depending on the host species, including but not limited to Freund's (complete and incomplete), mineral gels, such as aluminum hydroxide, surface active substances such as lysolecithin, pluronic polyols, polyanions, peptides, oil emulsions, key limpet hemocyanin, dinitrophenol, and potentially useful human adjuvants such as BCG and *Corynebacterium parvum*.

Monoclonal antibodies to Replikins may be prepared by using any technique that provides for the production of antibody molecules. These include but are not limited to the hybridoma technique originally described by Kohler and Milstein, (Nature, 1975, 256:495-497), the human B-cell hybridoma technique (Kosbor et al., 1983, Immunology Today, 4:72), and the EBV hybridoma technique (Cole et al., Monoclonal Antibodies and Cancer Therapy, Alan R. Liss, Inc., pp. 77-96). In addition, techniques developed for the production of chimeric antibodies (Morrison et al., 1984, Proc. Nat. Acad. Sci USA, 81:6851-6855) or other techniques may be used. Alternatively, techniques described for the production of single chain antibodies (U.S. Pat. No. 4,946,778) can be adapted to produce Replikin-specific single chain antibodies.

Particularly useful antibodies of the invention are those that specifically bind to Replikin sequences contained in peptides and/or polypeptides of influenza virus. For example, antibodies to any of peptides observed to be present in an emerging or re-emerging strain of influenza virus and combinations of such antibodies are useful in the treatment and/or prevention of influenza. Similarly, antibodies to any replikins present on malaria antigens and combinations of such antibodies are useful in the prevention and treatment of malaria.

Antibody fragments which contain binding sites for a Replikin may be generated by known techniques. For example, such fragments include but are not limited to F(ab')$_2$ fragments which can be produced by pepsin digestion of the antibody molecules and the Fab fragments that can be generated by reducing the disulfide bridges of the F(ab')$_2$ fragments. Alternatively, Fab expression libraries can be generated (Huse et al., 1989, Science, 246:1275-1281) to allow rapid and easy identification of monoclonal Fab fragments with the desired specificity.

The fact that antimalignin antibody is increased in concentration in human malignancy regardless of cancer cell type (FIG. 5), and that this antibody binds to malignant cells regardless of cell type now may be explained by the presence of the Replikin structures herein found to be present in most malignancies (FIG. 1 and Table 2). Population studies have shown that antimalignin antibody increases in concentration in healthy adults with age, and more so in high-risk families, as the frequency of cancer increases. An additional two-fold or greater antibody increase which occurs in early malignancy has been independently confirmed with a sensitivity of 97% in breast cancers 1-10 mm in size; Shown to localize preferentially in malignant cells in vivo, histochemically the antibody does not bind to normal cells but selectively binds to (FIG. 4$a,b$) and is highly cytotoxic to transformed cells in vitro (FIG. 4$c$-$f$). Since in these examples the same antibody is bound by several cell types, that is, brain glioma, hematopoietic cells (leukemia), and small cell carcinoma of lung, malignant Replikin class unity is again demonstrated.

Figure 5:
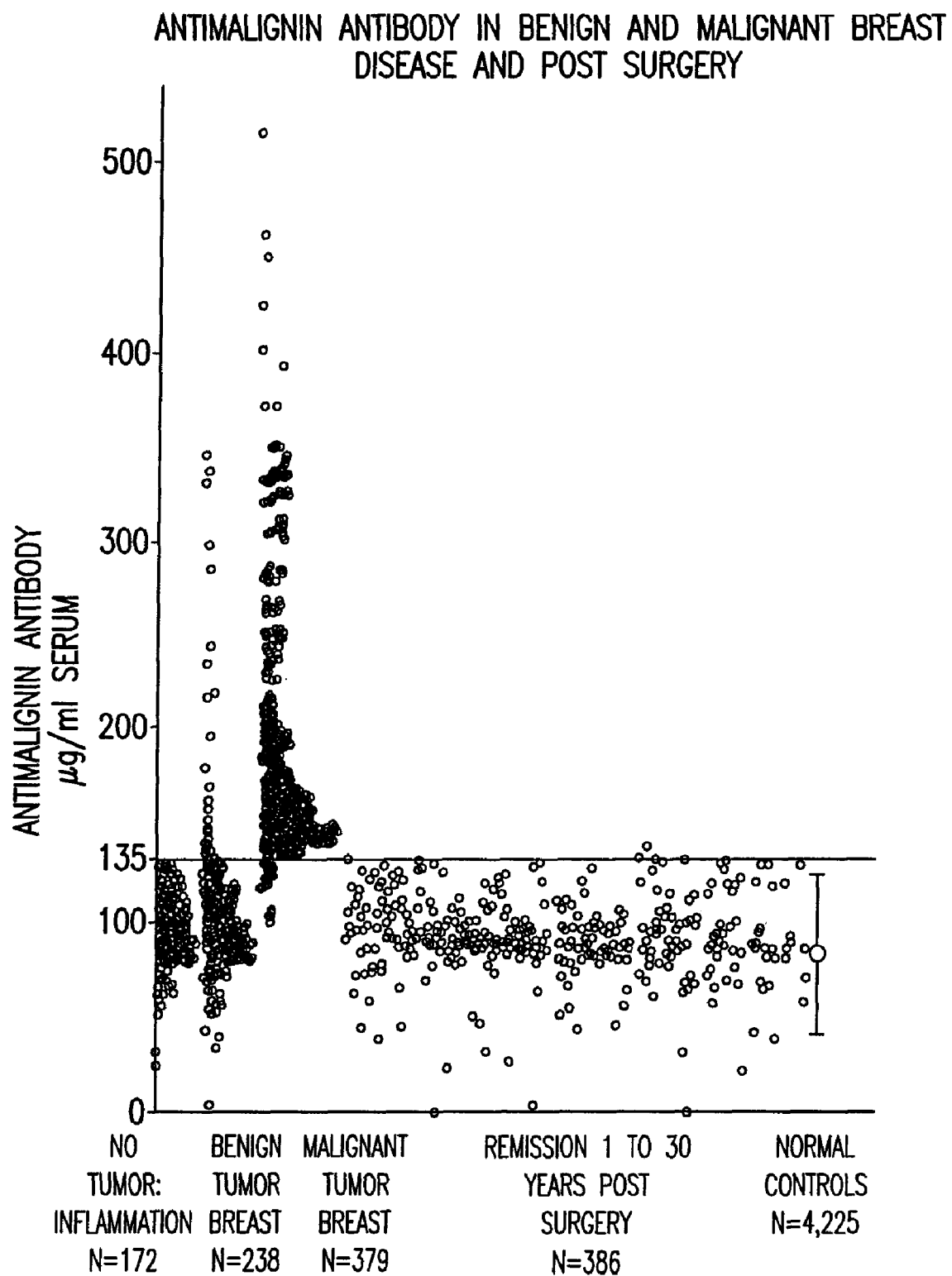
FIG. 5 is a plot of the amount of antimalignin antibody present in the serum of patients with benign or malignant breast disease pre- and post surgery.

Antimalignin does not increase with benign proliferation, but specifically increases only with malignant transformation and replication in breast in vivo and returns from elevated to normal values upon elimination of malignant cells (FIG. 5).

Antimalignin antibody concentration has been shown to relate quantitatively to the survival of cancer patients, that is, the more antibody, the longer the survival. Taken together, these results suggest that anti-Replikin antibodies may be a part of a mechanism of control of cell transformation and replication. Augmentation of this immune response may be useful in the control of replication, either actively with synthetic Replikins as vaccines, or passively by the administration of anti-Replikin antibodies, or by the introduction of non-immune based organic agents, such as for example, carbohydrates, lipids and the like, which are similarly designed to target the Replikin specifically. For organisms such as diatom plankton, foot and mouth disease virus, tomato leaf curl gemini virus, hepatitis B and C, HIV, influenza virus and malignant cells, identified constituent Replikins are useful as vaccines, and also may be usefully targeted for diagnostic purposes. Blood collected for transfusions, for example, may be screened for contamination of organisms, such as HIV, by screening for the presence of Replikins shown to be specific for the contamination organism. Also, screening for Replikin structures specific for a particular pathological organism, e.g., anthrax, leads to diagnostic detection of the organism in body tissue or in the environment.

The Replikin sequence structure is associated with the function of replication. Thus, whether the Replikins of this invention are used for targeting sequences that contain Replikins for the purpose of diagnostic identification, promoting replication, or inhibiting or attacking replication, for example, the structure-function relationship of the Replikin is fundamental. Thus, while the structure of the Replikin may be a part of a larger protein sequence, which may have been previously identified, it is preferable to utilize only the specific Replikin structure when seeking to induce antibodies that will recognize and attach to the Replikin fragment and thereby cause destruction of the cell. Even though the larger protein sequence may be known in the art as having a "replication associated function," vaccines using the larger protein often have failed or proven ineffective, even though they contain one or more Replikin sequences.

Although the present inventors do not wish to be held to a single theory, the studies herein suggest that the prior art vaccines are ineffective because they are based on the use of the larger protein sequence. The larger protein sequence invariably has one or more epitopes (independent antigenic sequences that can induce specific antibody formation); Replikin structures usually comprise one of these potential epitopes. The presence of other epitopes within the larger protein may interfere with adequate formation of antibodies to the Replikin, by "flooding" the immune system with irrelevant antigenic stimuli which may preempt the Replikin antigens, See, e.g., Webster, R. G., J. Immunol., 97(2):177-183 (1966); and Webster et al., J. Infect. Dis., 134:48-58, 1976; Klenerman et al, Nature 394:421-422 (1998) for a discussion of the well-known phenomenon "original antigenic sin"). The formation of an antibody to a non-Replikin epitope may allow binding to the cell, but not necessarily lead to cell destruction. The presence of structural "decoys" on the C-termini of malaria proteins is another aspect of this ability of other epitopes to interfere with binding of effective anti-Replikin antibodies, since the decoy epitopes have many lysine residues, but no histidine residues. Thus, decoy epitopes may bind anti-Replikin antibodies, but keep the antibodies away from histidine-bound respiratory enzymes.

It is well known in the art that in the course of antibody production against a "foreign" protein, the protein is first hydrolyzed into smaller fragments. Usually fragments containing from about six to ten amino acids are selected for antibody formation. Thus, if hydrolysis of a protein does not result in Replikin-containing fragments, anti-Replikin antibodies will not be produced. In this regard, it is interesting that Replikins contain lysine residues located six to ten amino acids apart, since lysine residues are known to bind to membranes.

Furthermore, Replikin sequences contain at least one histidine residue. Histidine is frequently involved in binding to redox centers. Thus, an antibody that specifically recognizes a Replikin sequence has a better chance of inactivating or destroying the cell in which the Replikin is located, as seen with anti-malignin antibody, which is perhaps the most cytotoxic antibody yet described, being active at picograms per cell.

One of the reasons that vaccines directed towards a particular protein antigen of a disease causing agent have not been fully effective in providing protection against the disease (such as foot and mouth vaccine which has been developed against the VP1 protein or large segments of the VP1 protein) is that antibody to the Replikins have not been produced. That is, either epitopes other than Replikins present in the larger protein fragments may interfere according to the phenomenon of "original antigenic sin", and/or because the hydrolysis of larger protein sequences into smaller sequences for processing to produce antibodies results in loss of integrity of any Replikin structure that is present, e.g., the Replikin is cut in two and/or the histidine residue is lost in the hydrolytic processing. The present studies suggest that for an effective vaccine to be produced, the Replikin sequences, and no other epitope, should be used as the vaccine. For example, a vaccine of the invention can be generated using any one of the Replikin peptides identified by the three point recognition system. Particularly preferred peptides for an influenza vaccine include peptides that have been demonstrated to be conserved over a period of one or more years, preferably about three years or more, and/or which are present in a strain of influenza virus shown to have the highest increase in concentration of Replikins relative to Replikin concentration in other influenza virus strains, e.g., an emerging strain. The increase in Replikin concentration preferably occurs over a period of at least about six months to one year, preferably at least about two years or more, and most preferably about three years or more. Among the preferred Replikin peptides for use in an influenza virus vaccine are those replikins observed to "re-emerge" after an absence from the hemagglutinin amino acid sequence for one or more years.

The Replikin peptides of the invention, alone or in various combinations are administered to a subject, preferably by i.v. or intramuscular injection, in order to stimulate the immune system of the subject to produce antibodies to the peptide. Generally the dosage of peptides is in the range of from about 0.1 µg to about 10 mg, preferably about 10 µg to about 1 mg, and most preferably about 50 µg to about 500 ug. The skilled practitioner can readily determine the dosage and number of dosages needed to produce an effective immune response.

Replikin DNA or RNA may have a number of uses for the diagnosis of diseases resulting from infection with a virus, bacterium or other Replikin encoding agent. For example, Replikin nucleotide sequences may be used in hybridization assays of biopsied tissue or blood, e.g., Southern or Northern analysis, including in situ hybridization assays, to diagnose the presence of a particular organism.

Also within the scope of the invention are oligoribonucleotide sequences, that include antisense RNA and DNA molecules and ribozymes that function to inhibit the translation of Replikin- or recognin-containing mRNA. Both antisense RNA and DNA molecules and ribozymes may be prepared by any method known in the art. The antisense molecules can be incorporated into a wide variety of vectors for delivery to a subject. The skilled practitioner can readily determine the best route of delivery, although generally i.v. or i.m. delivery is routine. The dosage amount is also readily ascertainable.

Particularly preferred antisense nucleic acid molecules are those that are complementary to a Replikin sequence contained in a mRNA encoding an influenza virus polypeptide, wherein the Replikin sequence comprises from 7 to about 50 amino acids including (1) at least one lysine residue located six to ten residues from a second lysine residue; (2) at least one histidine residue; and (3) at least 6% lysine residues. More preferred are antisense nucleic acid molecules that are complementary to a Replikin present in the coding strand of the gene or to the mRNA encoding the influenza virus hemagglutinin protein, wherein the antisense nucleic acid molecule is complementary to a nucleotide sequence encoding a Replikin that has been demonstrated to be conserved over a period of six months to one or more years and/or which are present in a strain of influenza virus shown to have an increase in concentration of Replikins relative to Replikin concentration in other influenza virus strains. The increase in Replikin concentration preferably occurs over a period of at least six months, preferably about one year, most preferably about two or three years or more.

In another embodiment of the invention, immune serum containing antibodies to one or more Replikins obtained from an individual exposed to one or more Replikins may be used to induce passive immunity in another individual or animal. Immune serum may be administered via i.v. to a subject in need of treatment. Passive immunity also can be achieved by injecting a recipient with preformed antibodies to one or more Replikins. Passive immunization may be used to provide immediate protection to individuals who have been exposed to an infectious organism. Administration of immune serum or preformed antibodies is routine and the skilled practitioner can readily ascertain the amount of serum or antibodies needed to achieve the desired effect.

In another aspect of the invention, Replikin structures are used to increase the replication of organisms. The present invention demonstrates that in influenza virus, for example, increased replication associated with epidemics is associated with increased concentration of Replikins. The increase is due to 1) the reappearance of particular replikin structures, which were present in previous years, but which then disappeared for one or more years; and/or 2) by the appearance of new replikin compositions. In addition, in malaria Replikins, repetition of the same Replikin in a single protein occurs. Thus, the present invention provides methods and compositions for increasing the replication of organisms. For example, the production of crops which are critical to feeding large populations throughout the world, such as rice, for example, can be improved by increasing the concentration (number of Replikins/100 amino acid residues) of any particular strain of the food crop.

As an example, in the *Oryza sativa* strain of rice, catalase isolated from immature seeds was observed to contain three different Replikins within the 491 amino acid sequence of the protein. Thus, by using recombinant gene cloning techniques well known in the art, the concentration of Replikin structures in an organism, such as a food crop plant, can be increased, which will promote increased replication of the organism.

The present invention also provides methods for identifying Replikin sequences in an amino acid or nucleic acid sequence. Visual scanning of over four thousand sequences was performed in developing the present 3-point-recognition methods. However, data banks comprising nucleotide and/or amino acid sequences can also be scanned by computer for the presence of sequences meeting the 3 point recognition requirements.

The three point recognition method may also be modified to identify other useful compounds of covalently linked organic molecules, including other covalently linked amino acids, nucleotides, carbohydrates, lipids or combinations thereof. In this embodiment of the invention a sequence is screened for subsequences containing three or more desired structural characteristics. In the case of screening compounds composed of covalently linked amino acids, lipids or carbohydrates the subsequence of 7 to about 50 covalently linked units should contain (1) at least one first amino acid, carbohydrate or lipid residue located seven to ten residues from a second of the first amino acid, carbohydrate or lipid residue; (2) encoding at least one second amino acid, lipid or carbohydrate residue; and (3) at least 6% of the first amino acid, carbohydrate or lipid residue. In the case of screening nucleotide sequences, the subsequence of about 21 to about 150 nucleotides should contain (1) at least one codon encoding a first amino acid located within eighteen to thirty nucleotides from a second codon encoding the first amino acid residue; (2) at least one second amino acid residue; and (3) encodes at least 6% of said first amino acid residue.

Figure 6:
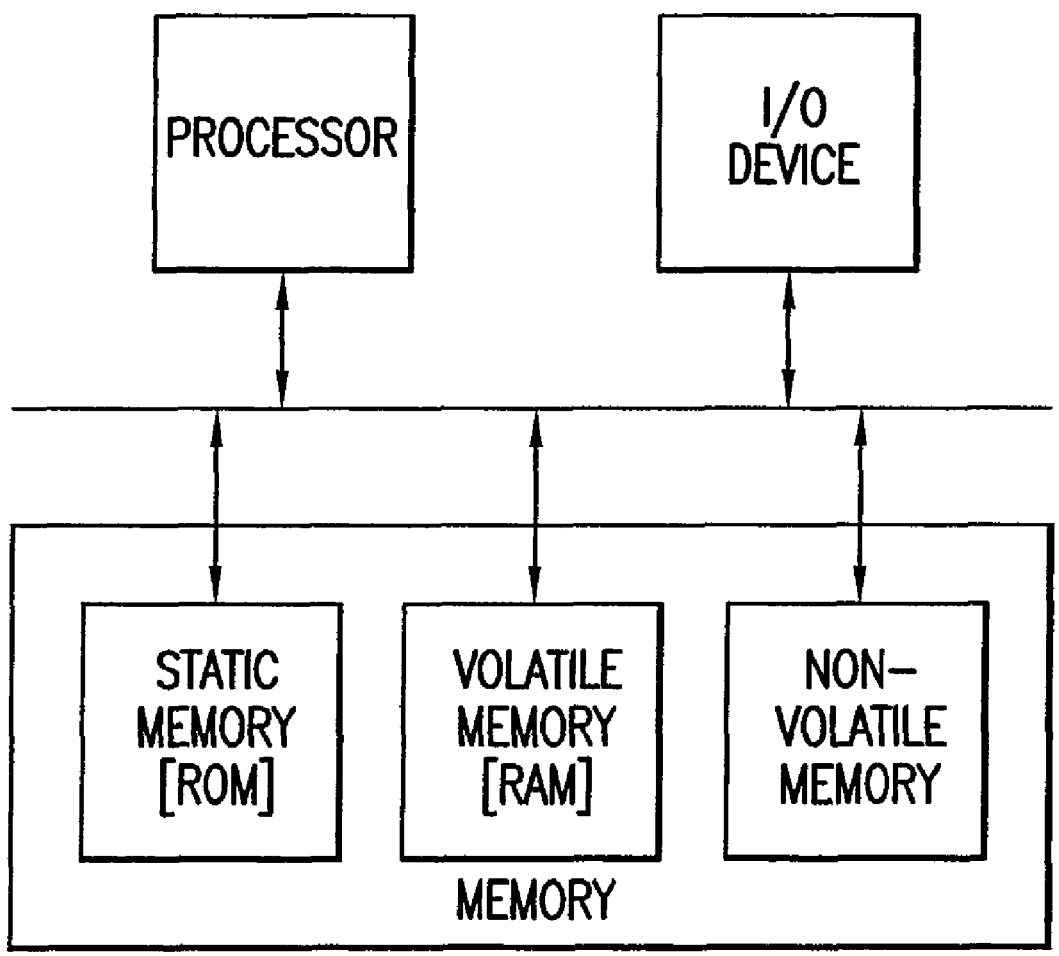
FIG. 6 is a box diagram depicting an embodiment of the invention wherein a computer is used to carry out the 3-point-recognition method of identifying replikin sequences.

According to another embodiment of the invention, the methods described herein may be performed by a computer. FIG. 6 is a block diagram of a computer available for use with the foregoing embodiments of the present invention. The computer may include a processor, an input/output device and a memory storing executable program instructions representing the 3-point-recognition methods of the foregoing embodiments. The memory may include a static memory, volatile memory and/or a nonvolatile memory. The static memory conventionally may be a read only memory ("ROM") provided on a magnetic, or an electrical or optical storage medium. The volatile memory conventionally may be a random access memory ("RAM") and may be integrated as a cache within the processor or provided externally from the processor as a separate integrated circuit. The non-volatile memory may be an electrical, magnetic or optical storage medium.

From a proteomic point of view the construction of a "3-point-recognition" template based on the new glioma peptide sequence led directly to identification of a biology-wide class of proteins having related structures and functions. The operation of the 3-point-recognition method resembles identification by the use of a "keyword" search; but instead of using the exact spelling of the keyword "kagvaflhkk" (SEQ ID NO.: 1) as in a typical sequence homology search, or in the nucleotide specification of an amino acid, an abstraction of the keyword delimited by the "3-point-recognition" parameters is used. This delimited abstraction, although derived from a single relatively short amino acid sequence leads to identification of a class of proteins with structures that are defined by the same specifications. That particular functions, in this case transformation and replication, in addition to structures, turn out also to be shared by members of the exposed class suggests that these structures and functions are related. Thus, from this newly identified short peptide sequence, a molecular recognition 'language' has been formulated, which previously has not been described. Further, the sharing of immunological specificity by diverse members of the class, as here demonstrated for the cancer Replikins, suggests that B cells and their product antibodies recognize Replikins by means of a similar recognition language. Since "3-point-recognition" is a proteomic method that specifies a particular class of proteins, using three or more different recognition points for other peptides similarly should provide useful information concerning other proteins classes. Further, the "3-point-recognition" method is applicable to other recognitions, for example to the TOLL 'innate' recognition of lipopolyssacharides of organisms.

Several embodiments of the present invention are specifically illustrated and described herein. However, it will be appreciated that modifications and variations of the present invention are encompassed by the above teachings and within the purview of the appended claims without departing from the spirit and intended scope of the invention.

Example 1

Process for Extraction, Isolation and Identification of Replikins and the Use of Replikins to Target, Label or Destroy Replikin-Containing Organisms a) Algae The following algae were collected from Bermuda water sites and either extracted on the same day or frozen at −20 degrees C. and extracted the next day. The algae were homogenized in a cold room (at 0 to 5 degrees C.) in 1 gram aliquots in neutral buffer, for example 100 cc. of 0.005M phosphate buffer solution, pH 7 ("phosphate buffer") for 15 minutes in a Waring blender, centrifuged at 3000 rpm, and the supernatant concentrated by perevaporation and dialyzed against phosphate buffer in the cold to produce a volume of approximately 15 ml. The volume of this extract solution was noted and an aliquot taken for protein analysis, and the remainder was fractionated to obtain the protein fraction having a pK range between 1 and 4. The preferred method of fractionation is chromatography as follows:

The extract solution is fractionated in the cold room (4 degrees C.) on a DEAE cellulose (Cellex-D) column 2.5× 11.0 cm, which has been equilibrated with 0.005M phosphate buffer. Stepwise eluting solvent changes are made with the following solutions:

Solution 1—4.04 g. $NaH_2PO_4$ and 0.5 g $NaH_2PO_4$ are dissolved in 15 liters of distilled water (0.005 molar, pH 7);

Solution 2—8.57 g. $NaH_2PO_4$ is dissolved in 2,480 ml. of distilled water;

Solution 3—17.1 g. of $NaH_2PO_4$ is dissolved in 2480 ml of distilled water (0.05 molar, pH 4.7);

Solution 4—59.65 g. of $NaH_2PO_4$ is dissolved in 2470 ml distilled water (0.175 molar);

Solution 5—101.6 g. of $NaH_2PO_4$ is dissolved in 2455 ml distilled water (pH 4.3);

Solution 6—0.340.2 g. of $NaH_7PO_4$ is dissolved in 2465 of distilled water (1.0 molar, pH 4.1);

Solution 7—283.63 g. of 80% phosphoric acid ($H_3PO_4$) is made up in 2460 ml of distilled water (1.0 molar, pH 1.0).

The extract solution, in 6 to 10 ml volume, is passed onto the column and overlayed with Solution 1, and a reservoir of 300 ml of Solution 1 is attached and allowed to drip by gravity onto the column. Three ml aliquots of eluant are collected and analyzed for protein content at OD 280 until all of the protein to be removed with Solution 1 has been removed from the column. Solution 2 is then applied to the column, followed in succession by Solutions 3, 4, 5, 6 and 7 until all of the protein which can, be removed with each Solution is removed from the column. The eluates from Solution 7 are combined, dialyzed against phosphate buffer, the protein content determined of both dialysand and dialyzate, and both analyzed by gel electrophoresis. One or two bands of peptide or protein of molecular weight between 3,000 and 25,000 Daltons are obtained in Solution 7. For example the algae *Caulerpa mexicana, Laurencia obtura, Cladophexa prolifera, Sargassum natans, Caulerpa verticillata, Halimeda tuna,* and *Penicillos capitatus*, after extraction and treatment as above, all demonstrated in Solution 7 eluates sharp peptide bands in this molecular weight region with no contaminants. These Solution 7 proteins or their eluted bands are hydrolyzed, and the amino acid composition determined. The peptides so obtained, which have a lysine composition of 6% or greater are Replikin precursors. These Replikin peptide precursors are then determined for amino acid sequence and the replikins are determined by hydrolysis and mass spectrometry as detailed in U.S. Pat. No. 6,242,578 B1. Those which fulfill the criteria defined by the "3-point-recognition" method are identified as Replikins. This procedure can also be applied to obtain yeast, bacterial and any plant Replikins.

b) Virus

Using the same extraction and column chromatography separation methods as above in a) for algae, Replikins in virus-infected cells are isolated and identified.

c) Tumor Cells In Vivo and In Vitro Tissue Culture

Using the same extraction and column chromatography separation methods as above in a) for algae, Replikins in tumor cells are isolated and identified. For example, Replikin precursors of Astrocytin isolated from malignant brain tumors, Malignin (Aglyco lOB) isolated from glioblastoma tumor cells in tissue culture, MCF7 mammary carcinoma cells in tissue culture, and $P_3J$ Lymphoma cells in tissue culture each treated as above in a) yielded Replikin precursors with lysine content of 9.1%, 6.7%, 6.7%, and 6.5% respectively. Hydrolysis and mass spectrometry of Aglyco lOB as described in Example 10 U.S. Pat. No. 6,242,578 B1 produced the amino acid sequence, ykagvaflhkkndiide the 16-mer Replikin.

Example 2

As an example of diagnostic use of Replikins: Aglyco lOB or the 16-mer Repliken may be used as antigen to capture and quantify the amount of its corresponding antibody present in serum for diagnostic purposes are as shown in FIGS. 2,3,4 and 7 of U.S. Pat. No. 6,242,578 B1.

As an example of the production of agents to attach to Replikins for labeling, nutritional or destructive purposes: Injection of the 16-mer Replikin into rabbits to produce the specific antibody to the 16-mer Replikin is shown in Example 6 and FIGS. 9A and 9B of U.S. Pat. No. 6,242,578 B1.

As an example of the use of agents to label Replikins: The use of antibodies to the 16-mer Replikin to label specific cells which contain this Replikin is shown in FIG. 5 and Example 6 of U.S. Pat. No. 6,242,578 B1.

As an example of the use of agents to destroy Replikins: The use of antibodies to the 16-mer Replikin to inhibit or destroy specific cells which contain this Replikin is shown in FIG. 6 of U.S. Pat. No. 6,242,578 B1.

Example 3

Analysis of sequence data of isolates of influenza virus hemagglutinin protein or neuraminidase protein for the presence and concentration of Replikins is carried out by visual scanning of sequences or through use of a computer program based on the 3-point recognition system described herein. Isolates of influenza virus are obtained and the amino acid sequence of the influenza hemagglutinin and/or neuraminidase protein is obtained by any art known method, such as by sequencing the hemagglutinin or neuraminidase gene and deriving the protein sequence therefrom. Sequences are scanned for the presence of new Replikins, conservation of Replikins over time and concentration of Replikins in each isolate. Comparison of the Replikin sequences and concentrations to the amino acid sequences obtained from isolates at an earlier time, such as about six months to about three years earlier, provides data that are used to predict the emergence of strains that are most likely to be the cause of influenza in upcoming flu seasons, and that form the basis for seasonal influenza peptide vaccines or nucleic acid based vaccines. Observation of an increase in concentration, particularly a stepwise increase in concentration of Replikins in a given strain of influenza virus for a period of about six months to about three years or more is a predictor of emergence of the strain as a likely cause of influenza epidemic or pandemic in the future.

Peptide vaccines or nucleic acid-based vaccines based on the Replikins observed in the emerging strain are generated. An emerging strain is identified as the strain of influenza virus-having the highest increase in concentration of replikin sequences within the hemagglutinin and/or neuraminidase sequence during the time period. Preferably, the peptide or nucleic acid vaccine is based on or includes any Replikin sequences that are observed to be conserved in the emerging strain. Conserved replikins are preferably those Replikin sequences which are present in the hemagglutinin or neuraminidase protein sequence for about two years and preferably longer. The vaccines may include any combination of Replikin sequences identified in the emerging strain.

For vaccine production, the Replikin peptide or peptides identified as useful for an effective vaccine are synthesized by any method, including chemical synthesis and molecular biology techniques, including cloning, expression in a host cell and purification therefrom. The peptides are preferably admixed with a pharmaceutically acceptable carrier in an amount determined to induce a therapeutic antibody reaction thereto. Generally, the dosage is about 0.1 µg to about 10 mg.

The influenza vaccine is preferably administered to a patient in need thereof prior to the onset of "flu season." Influenza flu season generally occurs in late October and lasts through late April. However, the vaccine may be administered at any time during the year. Preferably, the influenza vaccine is administered once yearly, and is based on Replikin sequences observed to be present, and preferably conserved in the emerging strain of influenza virus. Another preferred Replikin for inclusion in an influenza vaccine is a Replikin demonstrated to have re-emerged in a strain of influenza after an absence of one or more years.

Example 4

Analysis of sequence data of isolates of *Plasmodium falciparum* antigens for the presence and concentration of Replikins is carried out by visual scanning of sequences or through use of a computer program based on the 3-point recognition system described herein. Isolates of *Plasmodium falciparum* are obtained and the amino acid sequence of the protein is obtained by any art known method, such as by sequencing the gene and deriving the protein sequence therefrom. Sequences are scanned for the presence of Replikins, conservation of Replikins over time and concentration of Replikins in each isolate. This information provides data that are used to form the basis for anti-malarial peptide vaccines or nucleic acid based vaccines.

Peptide vaccines or nucleic acid-based vaccines based on the Replikins observed in the malaria causing organism are generated. Preferably, the peptide or nucleic acid vaccine is based on or includes any Replikin sequences that are observed to be present on a surface antigen of the organism. The vaccines may include any combination of Replikin sequences identified in the malaria causing strain.

For vaccine production, the Replikin peptide or peptides identified as useful for an effective vaccine are synthesized by any method, including chemical synthesis and molecular biology techniques, including cloning, expression in a host cell and purification therefrom. The peptides are preferably admixed with a pharmaceutically acceptable carrier in an amount determined to induce a therapeutic antibody reaction thereto. Generally, the dosage is about 0.1 µg to about 10 mg.

Then malaria vaccine is preferably administered to a patient in need thereof at any time during the year, and particularly prior to travel to a tropical environment.

What is claimed is:

1. An isolated or synthesized influenza virus peptide consisting of from 7 to about 50 amino acids with at least one lysine on one end of the peptide and at least one lysine or at least one histidine on the other end of the peptide comprising:
   (1) at least one lysine residue located six to ten residues from a second lysine residue;
   (2) at least one histidine residue; and
   (3) at least 6% lysine residues.

2. The peptide of claim 1 wherein the peptide is present in an emerging strain of influenza virus.

3. A therapeutic composition comprising the isolated or synthesized influenza virus peptide of claim 1 and a pharmaceutically acceptable carrier and/or adjuvant.

4. The therapeutic composition of claim 3 wherein the peptide is conserved in a strain of influenza virus for at least two consecutive years including the current year.

5. A therapeutic composition comprising a plurality of isolated or synthesized influenza virus peptides of claim 1 and a pharmaceutically acceptable carrier.

6. The therapeutic composition of claim 5 wherein at least one of the plurality of influenza virus peptides is conserved in the influenza virus hemagglutinin amino acid sequence for at least two consecutive years including the current year.

7. An influenza virus vaccine comprising at least one isolated or synthesized influenza peptide of claim 1.

8. The influenza virus vaccine of claim 7 wherein the vaccine comprises a plurality of isolated or synthesized influenza virus peptides of claim 1.

9. The vaccine of claim 7 wherein the at least one isolated or synthesized influenza peptide of claim 1 is conserved for at least two consecutive years in the emerging strain.

10. The isolated or synthesized influenza virus peptide of claim 1 wherein the n-terminus of the peptide is a lysine residue and the c-terminus of the peptide is a lysine residue.

11. The isolated or synthesized influenza virus peptide of claim 1 wherein the n-terminus of the peptide is a histidine residue and the c-terminus of the peptide is a lysine residue.

12. The isolated or synthesized influenza virus peptide of claim 1 wherein the n-terminus of the peptide is a lysine residue and the c-terminus of the peptide is a histidine residue.

13. The isolated or synthesized influenza virus peptide of claim 10 wherein the peptide comprises no more than two lysine residues.

14. The isolated or synthesized influenza virus peptide of claim 11 wherein the peptide comprises no more than one histidine residue.

15. The isolated or synthesized influenza virus peptide of claim 12 wherein the peptide comprises no more than one histidine residue.

16. An isolated or synthesized peptide consisting of an amino acid sequence defined by the formula $$AX_nB$$

wherein A is a lysine residue or a histidine residue, and when A is a lysine residue, B is a either a lysine residue or a histidine residue, and when A is a histidine residue, B is a lysine residue, wherein X is a sequence of amino acid residues having a length of n residues wherein n is an integer from 5 to 48, and wherein the amino acid sequence defined by the formula $AX_nB$ comprises (1) at least one lysine residue located six to ten residues from a second lysine residue;

(2) at least one histidine residue; and (3) at least 6% lysine residues within the total number of amino acid residues in the amino acid sequence defined by the formula $AX_nB$, and wherein said peptide is isolated from or identified within an influenza virus.

* * * * *